(12) United States Patent
Katsuta et al.

(10) Patent No.: US 6,331,634 B1
(45) Date of Patent: Dec. 18, 2001

(54) PROCESS FOR PREPARING 2-ALKYL-3-AMINOTHIOPHENE DERIVATIVE AND 3-AMINOTHIOPHENE DERIVATIVE

(75) Inventors: Hiroyuki Katsuta; Seiichi Ishii; Kanji Tomiya; Kenji Kodaka, all of Chiba-ken (JP)

(73) Assignee: Mitsui Chemicals, Inc. (JP)

( * ) Notice: Subject to any disclaimer, the term of this patent is extended or adjusted under 35 U.S.C. 154(b) by 0 days.

(21) Appl. No.: 09/694,837

(22) Filed: Oct. 24, 2000

Related U.S. Application Data

(62) Division of application No. 09/524,007, filed on Mar. 13, 2000, now Pat. No. 6,239,282.

(30) Foreign Application Priority Data

Mar. 16, 1999 (JP) ................................ 11-69387

(51) Int. Cl.$^7$ ............... C07D 333/36; C07D 333/40; C07D 409/12
(52) U.S. Cl. ............ 548/200; 544/405; 546/281.4; 548/200; 548/214; 548/365.7; 549/14; 549/59; 549/60; 549/69
(58) Field of Search .................. 548/200, 214, 548/365.7; 544/405; 549/14, 59, 60, 69

(56) References Cited

U.S. PATENT DOCUMENTS 5,747,518    5/1998  Yoshikawa et al. ............ 514/403

FOREIGN PATENT DOCUMENTS

0737682A1   10/1996  (EP).
0841336 A    5/1998  (EP).

OTHER PUBLICATIONS

M'hamed Berkaoui et al., "α–Vinylation of β–Aminothiophene Derivatives. Synthesis of 6–Functionalized Thieno[3,2–b]pyridines", Tetrahedron 54, 9055 to 9066 (1998).

Francis Outurquin et al., "Acid Catalyzed α–Alkylation of β–Aminothiophenes Using Aldehydes and Selenophenol Synthesis of Bis(3–amino–2–thienyl)methane Derivatives", Tetrahedron Letters, 34, 5715 to 5718 (1993).

Primary Examiner—Bernard Dentz
(74) Attorney, Agent, or Firm—Burns, Doane, Swecker & Mathis, L.L.P.

(57) ABSTRACT

A compound represented by the formula (1) which is useful as an agricultural fungicide or an intermediate thereof can be obtained by reacting a compound of the general formula (2) with a compound of the general formula (3) in the presence of an acid and reducing the resulted reaction mixture.

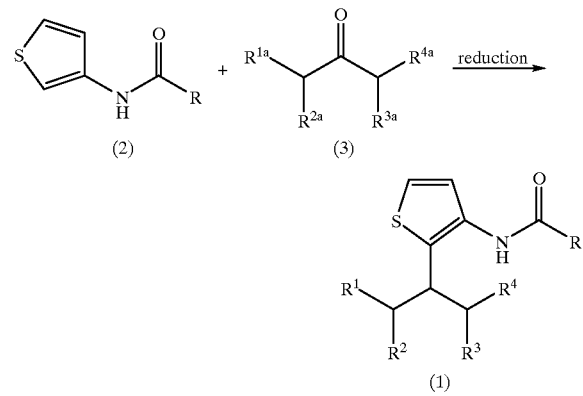

wherein, each of $R^1$ to $R^4$ and $R^{1a}$ to $R^{4a}$ independently represents a hydrogen atom or an alkyl group, and R represents an alkyl group, alkoxy group, phenyl group or 5-membered or 6-membered heterocyclic group.

5 Claims, No Drawings

PROCESS FOR PREPARING 2-ALKYL-3-AMINOTHIOPHENE DERIVATIVE AND 3-AMINOTHIOPHENE DERIVATIVE

This application is a divisional, of application Ser. No. 09/524,007, filed Mar. 13, 2000 now U.S. Pat. No. 6,239,282 B1.

BACKGROUND OF THE INVENTION

1. Field of the Invention

The present invention relate to a process for preparing a 2-alkyl-3-aminothiophene derivative useful as an agricultural fungicide or intermediate thereof, and novel 3-aminothiophene derivatives.

2. Description of the Related Art

Japanese Patent Application Laid-Open (JP-A) No. 9-235282 (EP-A 0737682 A1) describes that a certain kind of 2-alkyl-3-aminothiophene derivative has strong control effect against various plant disease damages. For producing this 2-alkyl-3-aminothiophene derivative, there is envisaged a method in which an alkyl group is directly introduced into 2-position of a 3-aminothiophene derivative. For example, Tetrahedron Letters, 34, 5715 to 5718 (1993) teaches that 2-alkyl-3-aminothiophene is obtained by reacting 3-aminothiophene with various aldehydes in the presence of p-toluenesulfonic acid and selenophenol.

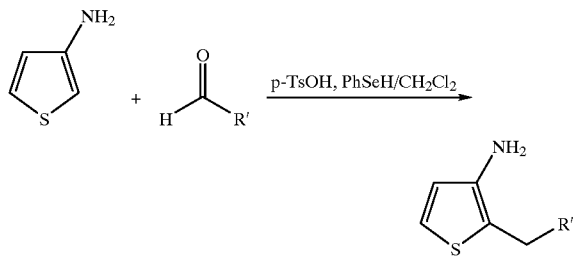

(wherein, R' represents an alkyl group.)

However, in this literature, there is utterly no description in which 2-alkyl-3-aminothiophene having a secondary alkyl group is synthesized. For obtaining a 2-alkyl-3-aminothiophene derivative having a secondary alkyl group using a synthesis method described in this literature, 3-aminothiophene derivative has to be reacted with ketones. However, when the present inventors substituted an aldehyde for the ketone and conducted this reaction, 3-aminothiophene was decomposed and the intended 2-alkyl-3-aminothiophene derivative or 2-alkenyl-3-aminothiophene derivative could not be obtained (Reference Example 1). Further, this literature includes a problem as an industrial production method since the reaction uses as a reducing agent selenophenol which is not easily obtained industrially.

Further, Tetrahedron 54, 9055 to 9066 (1998) teaches that when an aldehyde having branching at α-position is reacted with 3-aminothiophene or 3-aminothiophene derivative, an primary alkenyl group is introduced. However, this literature includes utterly no description regarding reactions using a ketone.

SUMMARY OF THE INVENTION

The object of the present invention is to provide a process for industrially preparing a compound having a secondary alkyl group among 2-alkyl-3-aminothiophene derivatives useful as an agricultural and horticultural fungicide or intermediate thereof by reacting a 3-aminothiophene derivative with aketone.

The present inventors have studied for solving the above-described problems and found that when a 3-aminothiophene derivative in which an amino group at 3-position is substituted with an amide bond or carbamate bond is reacted with various ketones in the presence of an acid, a secondary alkenyl group is introduced into 2-position of the 3-aminothiophene derivative, and when this alkenyl group is reduced by an industrially possible method, it can be converted to an alkyl group easily, completing the invention.

Namely, the aspect of the present invention relates to following (1) to (6).

(1) A process for preparing a 2-alkyl-3-aminothiophene derivative represented by the formula (1):

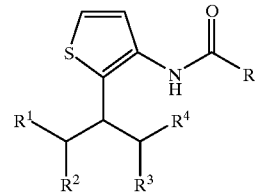

(1)

wherein, R represents a hydrogen atom, alkyl group or alkoxy group which may be substituted, aromatic or non-aromatic hydrocarbon ring which may be substituted, aromatic or non-aromatic heterocyclic ring which may be substituted, each of $R^1$, $R^2$, $R^3$ and $R^4$ independently represents a hydrogen atom or straight or branched alkyl group having 1 to 12 carbon atoms, and $R^1$ and $R^2$, $R^3$ and $R^4$, $R^1$ and $R^3$, $R^1$ and $R^4$, $R^2$ and $R^3$ or $R^2$ and $R^4$ may together form a cycloalkyl group, comprising reacting a compound represented by the formula (2):

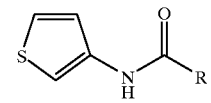

(2)

wherein, R is as defined above, with a compound represented by the formula (3):

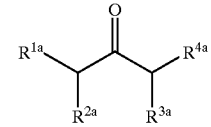

(3)

wherein, each of $R^{1a}$, $R^{2a}$, $R^{3a}$ and $R^{4a}$ independently represents a hydrogen atom, straight or branched alkyl group having 1 to 12 carbon atoms or straight or branched alkenyl group having 1 to 12 carbon atoms, and $R^{1a}$ and $R^{2a}$, $R^{3a}$ and $R^{4a}$, $R^{1a}$ and $R^{3a}$, $R^{1a}$ and $R^{4a}$, $R^{2a}$ and $R^{3a}$ or $R^{2a}$ and $R^{4a}$ may together form a cycloalkyl group or cycloalkenyl group, in the presence of an acid, and reducing the resulting reaction mixture.

(2) A process for preparing a mixture of 2-alkenyl-3-aminothiophene derivatives containing compounds represented by the formulae (4a), (4b), (4c) and (4d) respectively:

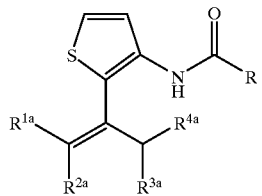
(4a)

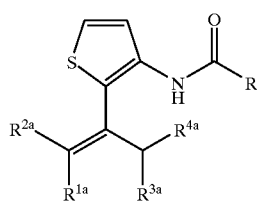
(4b)

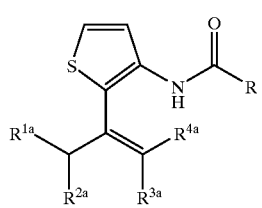
(4c)

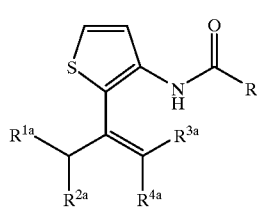
(4d)

wherein, R represents a hydrogen atom, alkyl group or alkoxy group which may be substituted, aromatic or non-aromatic hydrocarbon ring which may be substituted, aromatic or non-aromatic heterocyclic ring which may be substituted, each of $R^{1a}$, $R^{2a}$, $R^{3a}$ and $R^{4a}$ independently represents a hydrogen atom, straight or branched alkyl group having 1 to 12 carbon atoms or straight or branched alkenyl group having 1 to 12 carbon atoms and $R^{1a}$ and $R^{2a}$, $R^{3a}$ and $R^{4a}$, $R^{1a}$ and $R^{3a}$, $R^{1a}$ and $R^{4a}$, $R^{2a}$ and $R^{3a}$ or $R^{2a}$ and $R^{4a}$ may together form a cycloalkyl group or cycloalkenyl group, comprising reacting a compound represented by the formula (2):

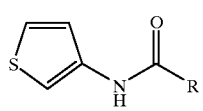
(2)

wherein, R is as defined above, with a compound represented by the formula (3):

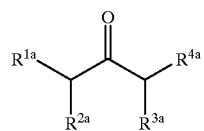
(3)

wherein, $R^{1a}$ to $R^{4a}$ are as define above, in the presence of an acid.

(3) A process for preparing 2-alkyl-3-aminothiophene represented by the formula (1a):

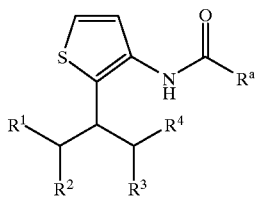
(1a)

wherein, $R^a$ represents a group represented by any of the following (A1) to (A12):

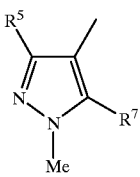
(A1)

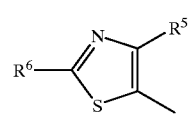
(A2)

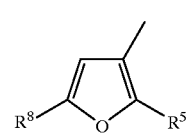
(A3)

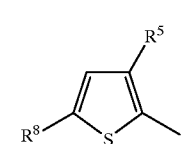
(A4)

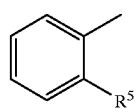
(A5)

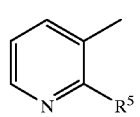
(A6)

-continued (A7)
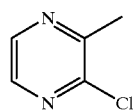

(A8)
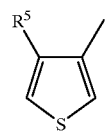

(A9)
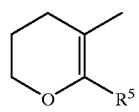

(A10)
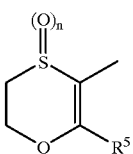

(A11)
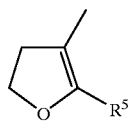

(A12)
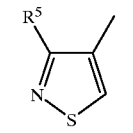

wherein, $R^5$ represents a trifluoromethyl group, difluoromethyl group, methyl group, ethyl group or halogen atom, $R^6$ represents a hydrogen atom, methyl group, trifluoromethyl group, halogen atom, methoxy group or amino group, $R^7$ represents a hydrogen atom, halogen atom, methyl group or methoxy group, $R^8$ represents a hydrogen atom, methyl group, ethyl group or halogen atom, and n represents an integer from 0 to 2, and herein, in the case of (A9), (A10) or (A11), $R^5$ is not a halogen atom, each of $R^1$, $R^2$, $R^3$ and $R^4$ independently represents a hydrogen atom or straight or branched alkyl group having 1 to 12 carbon atoms, and $R^1$ and $R^2$, $R^3$ and $R^4$, $R^1$ and $R^3$, $R^1$ and $R^4$, $R^2$ and $R^3$ or $R^2$ and $R^4$ may together form a cycloalkyl group, comprising reacting a compound represented by the formula (2):

(2)
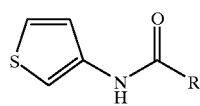

wherein, R represents a hydrogen atom, alkyl group or alkoxy group which may be substituted, aromatic or non-aromatic hydrocarbon ring which may be substituted or aromatic or non-aromatic heterocyclic ring which may be substituted, with a compound represented by the formula (3):

(3)
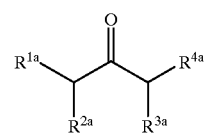

wherein, each of $R^{1a}$, $R^{2a}$, $R^{3a}$ and $R^{4a}$ independently represents a hydrogen atom, straight or branched alkyl group having 1 to 12 carbon atoms or straight or branched alkenyl group having 1 to 12 carbon atoms, and $R^{1a}$ and $R^{2a}$, $R^{3a}$ and $R^{4a}$, $R^{1a}$ and $R^{3a}$, $R^{1a}$ and $R^{4a}$, $R^{2a}$ and $R^{3a}$ or $R^{2a}$ and $R^{4a}$ may together form a cycloalkyl group or cycloalkenyl group, in the presence of an acid, reducing the resulting reaction mixture to obtain a compound represented by the formula (1):

(1)
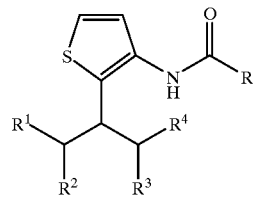

wherein, R, $R^1$, $R^2$, $R^3$ and $R^4$ are as defined above, further hydrolyzing the resultant compound under acidic or alkaline condition to obtain a compound represented by the formula (5):

(5)
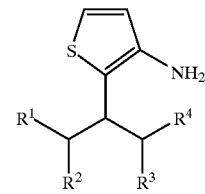

wherein, $R^1$, $R^2$, $R^3$ and $R^4$ are as defined above, and reacting this compound with a compound represented by the formula (8a):

(8a)
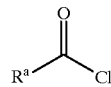

wherein, $R^a$ is as defined above.
(4) A 3-aminothiophene derivative represented by the formula (6a):

(6a)
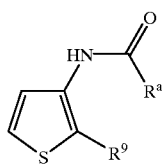

wherein, $R^9$ represents a hydrogen atom, carboxyl group or alkoxycarbonyl group having 1 to 6 carbon atoms and $R^a$ represents a group represented by any of the following (A1) to (A12):

(A1)
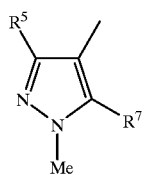

(A2)
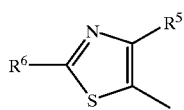

(A3)
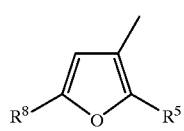

(A4)
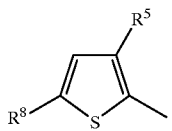

(A5)
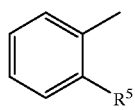

(A6)
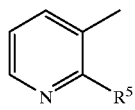

(A7)
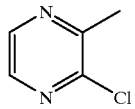

(A8)
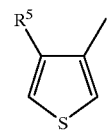

(A9)
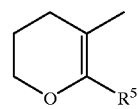

(A10)
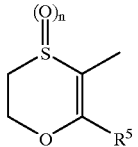

(A11)
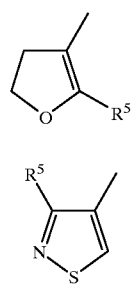

(A12)

wherein, $R^5$ represents a trifluoromethyl group, difluoromethyl group, methyl group, ethyl group or halogen atom, $R^6$ represents a hydrogen atom, methyl group, trifluoromethyl group, halogen atom, methoxy group or amino group, $R^7$ represents a hydrogen atom, halogen atom, methyl group or methoxy group, $R^8$ represents a hydrogen atom, methyl group, ethyl group or halogen atom, and n represents an integer from 0 to 2, and herein, in the case of (A9), (A10) or (A11), $R^5$ is not a halogen atom.

(5) A mixture of 2-alkenyl-3-aminothiophene derivatives containing compounds represented by the formulae (4a)', (4b)', (4c)' and (4d)' respectively:

(4a)'
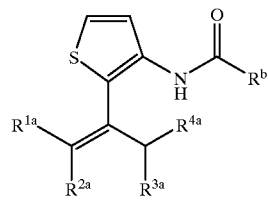

(4b)'
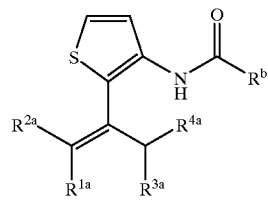

(4c)'
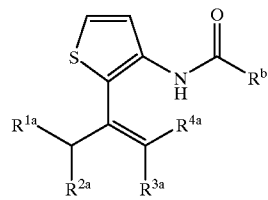

-continued (4d)′

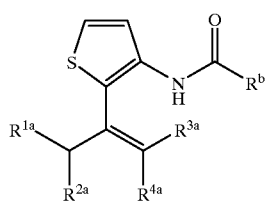

wherein, $R^b$ represents a hydrogen atom, alkyl group or alkoxy group which may be substituted, aromatic or non-aromatic hydrocarbon ring which may be substituted or aromatic or non-aromatic heterocyclic ring which may be substituted, and each of $R^{1a}$, $R^{2a}$, $R^{3a}$ and $R^{4a}$ independently represents a hydrogen atom, straight or branched alkyl group having 1 to 12 carbon atoms or straight or branched alkenyl group having 1 to 12 carbon atoms, and $R^{1a}$ and $R^{2a}$, $R^{3a}$ and $R^{4a}$, $R^{1a}$ and $R^{3a}$, $R^{1a}$ and $R^{4a}$, $R^{2a}$ and $R^{3a}$ or $R^{2a}$ and $R^{4a}$ may together form a cycloalkyl group or cycloalkenyl group, excepting the case in which $R^b$ represents a group represented by any of the following (A1) to (A12):

(A1)

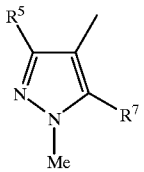

(A2)

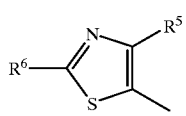

(A3)

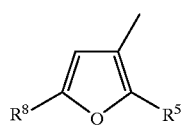

(A4)

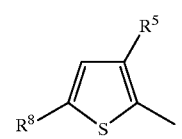

(A5)

(A6)

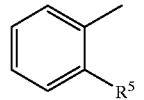

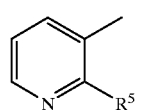

(A7)

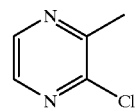

(A8)

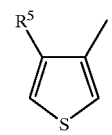

(A9)

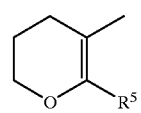

(A10)

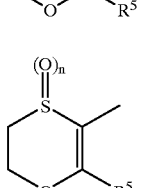

(A11)

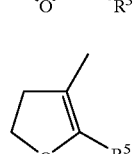

(A12)

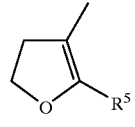

wherein, $R^5$ represents a trifluoromethyl group, difluoromethyl group, methyl group, ethyl group or halogen atom, $R^6$ represent a hydrogen atom, methyl group, trifluoromethyl group, halogen atom, methoxy group or amino group, $R^7$ represents a hydrogen atom, halogen atom, methyl group or methoxy group, $R^8$ represents a hydrogen atom, methyl group, ethyl group or halogen atom, and n represents an integer from 0 to 2, and herein, in the case of (A9), (A10) or (A11), $R^5$ is not a halogen atom, and the case in which $R^b$ represents a tert-butoxy group and $R^{1a}$, $R^{2a}$, $R^{3a}$ and $R^{4a}$ all represent a hydrogen atom being excluded.

(6) A 2-alkyl-3-aminothiophene derivative represented by the formula (1b):

(1b)

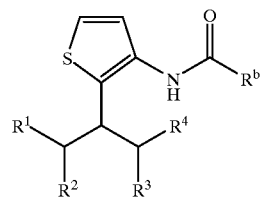

wherein, $R^b$ represents a hydrogen atom, alkyl group or alkoxy group which may be substituted, aromatic or non-aromatic hydrocarbon ring which may be substituted or aromatic or non-aromatic heterocyclic ring which may be substituted, and each of $R^1$, $R^2$, $R^3$ and $R^4$ independently represents a hydrogen atom or straight or branched alkyl group having 1 to 12 carbon atoms, and $R^1$ and $R^2$, $R^3$ and $R^4$, $R^1$ and $R^3$, $R^1$ and $R^4$, $R^2$ and $R^3$ or $R^2$ and $R^4$ may together form a cycloalkyl group, excepting the case in which $R^b$ represents a group represented by any of the following (A1) to (A12):

(A1)
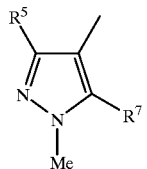

(A2)
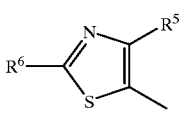

(A3)
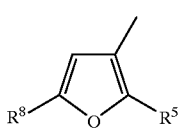

(A4)
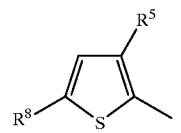

(A5)
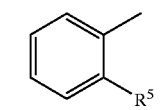

(A6)
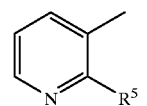

(A7)
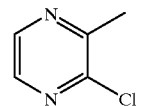

(A8)
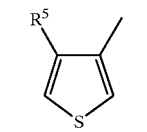

(A9)
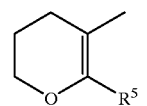

-continued (A10)
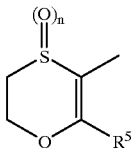

(A11)
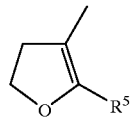

(A12)
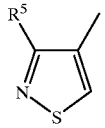

wherein, $R^5$ represents a trifluoromethyl group, difluoromethyl group, methyl group, ethyl group or halogen atom, $R^6$ represents a hydrogen atom, methyl group, trifluoromethyl group, halogen atom, methoxy group or amino group, $R^7$ represents a hydrogen atom, halogen atom, methyl group or methoxy group, $R^8$ represents a hydrogen atom, methyl group, ethyl group or halogen atom, and n represents an integer from 0 to 2, and herein, in the case of (A9), (A10) or (A11), $R^5$ is not a halogen atom.

DETAILED DESCRIPTION OF THE PREFERRED EMBODIMENTS

In the present invention, R may represent a hydrogen atom, and examples of an unsubstituted or substituted alkyl group represented by R include alkyl groups such as a methyl group, ethyl group, propyl group, isopropyl group, butyl group, isobutyl group, sec-butyl group, tert-butyl group, hexyl group, decyl group, methoxymethyl group, ethoxymethyl group, phenyl-methyl group and the like, examples of an unsubstituted or substituted alkoxy group represented by R include alkoxy groups such as a methoxy group, ethoxy group, propoxy group, isopropoxy group, cyclopropoxy group, butoxy group, isobutoxy group, sec-butoxy group, tert-butoxy group, cyclohexyloxy group, hexyloxy group, benzyloxy group and the like, examples of an unsubstituted or substituted aromatic hydrocarbon ring represented by R include a phenyl group and substituted phenyl groups, the substituent on the substituted phenyl groups being, for example, an alkyl group such as a methyl group, ethyl group, propyl group, isopropyl group and the like, an alkoxy group such as a methoxy group, ethoxy group, propoxy group, isopropoxy group and the like, a halogen atom such as chlorine atom, bromine atom, fluorine atom and iodine atom, or a nitro group, cyano group, amino group or the like; examples of an unsubstituted or substituted non-aromatic hydrocarbon ring represented by R include non-aromatic hydrocarbon rings such as a cyclopropyl group, cyclopentyl group, cyclohexyl group, cyclohexenyl group and the like, examples of an unsubstituted or substituted aromatic heterocyclic ring represented by R include a pyrazolyl group, thiazolyl group, isothiazolyl group, furyl group, thienyl group, pyridyl group, pyrazinyl group, oxazolyl group, pyrrolyl group, substituted pyrazolyl group, substituted thiazolyl group, substituted isothiazolyl group, substituted furyl group, substituted thienyl group, substituted pyridyl group, substituted pyrazinyl group, substituted oxazolyl group, substituted pyrrolyl group and the like, the substituent on the substituted pyrazolyl group, substituted thiazolyl group, substituted isothiazolyl group, substituted furyl group, substituted thienyl group, substituted pyridyl group, substituted pyrazinyl group, substituted oxazolyl group and substituted pyrrolyl group being, for example, an alkyl group such as a methyl group, ethyl group, propyl group, isopropyl group and the like, a haloalkyl group such as a trifluoromethyl group, difluoromethyl group and the like, a halogen atom such as fluorine atom, chlorine atom, bromine atom and iodine atom, or an amino group, cyano group or the like; and examples of an unsubstituted or substituted non-aromatic heterocyclic ring represented by R include a dihydropyranyl group, dihydrofuryl group, tetrahydrofuryl group, 2,3-dihydro-1,4-oxathiin-5-yl group, substituted dihydropyranyl group, substituted dihydrofuryl group, substituted tetrahydrofuryl group, substituted 2,3-dihydro-1,4-oxathiin-5-yl group and the like, the substituent on the substituted dihydropyranyl group, substituted dihydrofuryl group, substituted tetrahydrofuryl group and substituted 2,3-dihydro-1,4-oxathiin-5-yl group being, for example, an alkyl group such as a methyl group, ethyl group, propyl group, isopropyl group and the like, a haloalkyl group such as a trifluoromethyl group, difluoromethyl group and the like, a halogen atom such as fluorine atom, chlorine atom, iodine atom and the like, or an amino group, cyano group or the like. When R represents (A1), 4-pyrazolyl groups in which $R^5$ at 3-position represents a trifluoromethyl group, difluoromethyl group, methyl group, ethyl group or halogen atom and $R^7$ at 5-position represents a hydrogen atom, halogen atom, methyl group or methoxy group and methyl is substituted on 1-position are listed, examples thereof including a 1,3-dimethyl-4-pyrazolyl group, 5-chloro-1,3-dimethyl-4-pyrazolyl group, 5-chloro-1-methyl-3-trifluoromethyl-4-pyrazolyl group, 1-methyl-3-trifluoromethyl-4-pyrazolyl group, 1-methyl-3-difluoromethyl-4-pyrazolyl group, 1-methyl-3-ethyl-4-pyrazolyl group, 1-methyl-3-chloro-4-pyrazolyl group, 1-methyl-3-trifluoromethyl-5-methoxy-4-pyrazolyl group and the like, when R represents (A2), 5-thiazolyl groups in which $R^5$ at 4-position represents a trifluoromethyl group, difluoromethyl group, methyl group, ethyl group or halogen atom and $R^6$ at 2-position represents a hydrogen atom, methyl group, trifluoromethyl group, halogen atom, methoxy group or amino group are listed, examples thereof including a 2-methyl-4-trifluoromethyl-5-thiazolyl group, 2-methyl-4-difluoromethyl-5-thiazolyl group, 4-trifluoromethyl-5-thiazolyl group, 2,4-dimethyl-5-thiazolyl group, 2-methyl-4-ethyl-5-thiazolyl group, 2-amino-4-methyl-5-thiazolyl group, 2-methoxy-4-methyl-5-thiazolyl group, 2-chloro-4-methyl-5-thiazolyl group and the like, when R represents (A3), 3-furyl groups in which $R^5$ at 2-position represents a trifluoromethyl group, difluoromethyl group, methyl group, ethyl group or halogen atom and $R^8$ at 5-position represents a hydrogen atom, methyl group, ethyl group or halogen atom are listed, examples thereof including a 2-methyl-3-furyl group, 2,5-dimethyl-3-furyl group, 2-chloro-3-furyl group, 2-trifluoromethyl-3-furyl group and the like, when R represents (A4), 2-thienyl groups in which $R^5$ at 3-position represents a trifluoromethyl group, difluoromethyl group, methyl group, ethyl group or halogen atom and $R^8$ at 5-position represents a hydrogen atom, methyl group or halogen atom are listed, examples thereof including a 3-methyl-2-thienyl group, 3,5-dimethyl-2-thienyl group, 3-chloro-2-thienyl group, 3-iodo-2-thienyl group and the like, when R represents (A5), phenyl groups in which $R^5$ at 2-position represents a trifluoromethyl group, difluoromethyl group, methyl group, ethyl group or halogen atom are listed, examples thereof including a 2-trifluoromethylphenyl group, 2-difluoromethylphenyl group, 2-methylphenyl group, 2-ethylphenyl group, 2-fluorophenyl group, 2-chlorophenyl group, 2-bromophenyl group, 2-iodophenyl group, when R represents (A6), 3-pyridyl groups in which $R^5$ at 2-position represents a trifluoromethyl group, difluoromethyl group, methyl group, ethyl group or halogen atom are listed, examples thereof including a 2-trifluoromethyl-3-pyridyl group, 2-difluoromethyl-3-pyridyl group, 2-methyl-3-pyridyl group, 2-ethyl-3-pyridyl group, 2-fluoro-3-pyridyl group, 2-chloro-3-pyridyl group, 2-bromo-3-pyridyl group and 2-iodo-3-pyridyl group, when R represents (A7), examples thereof include a 2-chloro-3-pyradinyl group, when R represents (A8), 4-thienyl groups in which $R^5$ at 3-position represents a trifluoromethyl group, difluoromethyl group, methyl group, ethyl group or halogen atom are listed, examples thereof including a 3-trifluoromethyl-4-thienyl group, 3-difluoromethyl-4-thienyl group, 3-methyl-4-thienyl group, 3-ethyl-4-thienyl group, 3-fluoro-4-thienyl group, 3-chloro-4-thienyl group, 3-bromo-4-thienyl group and 3-iodo-4-thienyl group, when R represents (A9), 3,4-dihydro-2H-pyran-5-yl groups in which $R^5$ at 6-position represents a trifluoromethyl group, difluoromethyl group, methyl group or ethyl group are listed, examples thereof including a 6-trifluoromethyl-3,4-dihydro-2H-pyran-5-yl group, 6-difluoromethyl-3,4-dihydro-2H-pyran-5-yl group, 6-methyl-3,4-dihydro-2H-pyran-5-yl group and 2-ethyl-3,4-dihydro-2H-pyran-5-yl group, and when R represents (A10), 2,3-dihydro-1,4-oxathiin-5-yl groups, 2,3-dihydro-1,4-oxathiin-4-oxide-5-yl groups or 2,3-dihydro-1,4-oxathiin-4,4-dioxide-5-yl groups in which $R^5$ at 6-position represents a trifluoromethyl group, difluoromethyl group, methyl group or ethyl group are listed, examples thereof including a 6-methyl-2,3-dihydro-1,4-oxathiin-5-yl group, 6-methyl-2,3-dihydro-1,4-oxathiin-4-oxide-5-yl group, 6-methyl-2,3-dihydro-1,4-oxathiin-4,4-dioxide-5-yl group and the like. When R represents (A11), 2,3-dihydro-4-furyl groups in which $R^5$ at 5-position represents a trifluoromethyl group, difluoromethyl group, methyl group or ethyl group are listed, examples thereof including a 5-trifluoromethyl-2,3-dihydro-4-furyl group, 5-difluoromethyl-2,3-dihydro-4-furyl group, 5-methyl-2,3-dihydro-4-furyl group and 5-ethyl-2,3-dihydro-4-furyl group, and when R represents (A12), 4-isothiazolyl groups in which $R^5$ at 3-position represents a trifluoromethyl group, difluoromethyl group, methyl group, ethyl group or halogen atom are listed, examples thereof including a 3-trifluoromethyl-4-isothiazolyl group, 3-difluoromethyl-4-isothiazolyl group, 3-methyl-4-isothiazolyl group, 3-ethyl-4-isothiazolyl group, 3-fluoro-4-isothiazolyl group, 3-chloro-4-isothiazolyl group, 3-bromo-4-isothiazolyl group and 3-iodo-4-isothiazolyl group.

$R^1$, $R^2$, $R^3$ and $R^4$ may represent a hydrogen atom, and examples of an alkyl group represented by $R^1$, $R^2$, $R^3$ and $R^4$ include straight or branched alkyl groups having 1 to 12 carbon atoms such as a methyl group, ethyl group, propyl group, isopropyl group, butyl group, isobutyl group, sec-butyl group, tert-butyl group, hexyl group, decyl group, dodecyl group and the like.

$R^{1a}$, $R^{2a}$, $R^{3a}$ and $R^{4a}$ may represent a hydrogen atom, and examples of an alkyl group represented by $R^{1a}$, $R^{2a}$, $R^{3a}$ and $R^{4a}$ include straight or branched alkyl groups having 1 to 12 carbon atoms such as a methyl group, ethyl group, propyl group, isopropyl group, butyl group, isobutyl group, sec-butyl group, tert-butyl group, hexyl group, decyl group, dodecyl group and the like, and examples of an alkenyl group represented by $R^{1a}$, $R^{2a}$, $R^{3a}$ and $R^{4a}$ include straight or branched alkenyl groups having 1 to 12 carbon atoms such as an ethenyl group, 1-propenyl group, 2-propenyl group, isopropenyl group, 1-butenyl group, 2-butenyl group, 1-hexenyl group, 2-dodecyl group and the like.

$R^9$ may represent a hydrogen atom or carboxyl group, and examples of an alkoxycarbonyl group represented by $R^9$ include alkoxycarbonyl groups having 1 to 6 carbon atoms such as a methoxycarbonyl group, ethoxycarbonyl group, propoxycarbonyl group, isopropoxycarbonyl group, butoxycarbonyl group, tert-butoxycarbonyl group, hexyloxycarbonyl group and the like.

When $R^a$ represents (A1), 4-pyrazolyl groups in which $R^5$ at 3-position represents a trifluoromethyl group, difluoromethyl group, methyl group, ethyl group or halogen atom and $R^7$ at 5-position represents a hydrogen atom, halogen atom, methyl group or methoxy group and methyl is substituted on 1-position are listed, examples thereof including a 1,3-dimethyl-4-pyrazolyl group, 5-chloro-1,3-dimethyl-4-pyrazolyl group, 5-chloro-1-methyl-3-trifluoromethyl-4-pyrazolyl group, 1-methyl-3-trifluoromethyl-4-pyrazolyl group, 1-methyl-3-difluoromethyl-4-pyrazolyl group, 1-methyl-3-ethyl-4-pyrazolyl group, 1-methyl-3-chloro-4-pyrazolyl group, 1-methyl-3-trifluoromethyl-5-methoxy-4-pyrazolyl group and the like, when $R^a$ represents (A2), 5-thiazolyl groups in which $R^5$ at 4-position represents a trifluoromethyl group, difluoromethyl group, methyl group, ethyl group or halogen atom and $R^6$ at 2-position represents a hydrogen atom, methyl group, trifluoromethyl group, halogen atom, methoxy group or amino group are listed, examples thereof including a 2-methyl-4-trifluoromethyl-5-thiazolyl group, 2-methyl-4-difluoromethyl-5-thiazolyl group, 4-trifluoromethyl-5-thiazolyl group, 2,4-dimethyl-5-thiazolyl group, 2-methyl-4-ethyl-5-thiazolyl group, 2-amino-4-methyl-5-thiazolyl group, 2-methoxy-4-methyl-5-thiazolyl group, 2-chloro-4-methyl-5-thiazolyl group and the like, when $R^a$ represents (A3), 3-furyl groups in which $R^5$ at 2-position represents a trifluoromethyl group, difluoromethyl group, methyl group, ethyl group or halogen atom and $R^8$ at 5-position represents a hydrogen atom, methyl group, ethyl group or halogen atom are listed, examples thereof including a 2-methyl-3-furyl group, 2,5-dimethyl-3-furyl group, 2-chloro-3-furyl group, 2-trifluoromethyl-3-furyl group and the like, when $R^a$ represents (A4), 2-thienyl groups in which $R^5$ at 3-position represents a trifluoromethyl group, difluoromethyl group, methyl group, ethyl group or halogen atom and $R^8$ at 5-position represents a hydrogen atom, methyl group or halogen atom are listed, examples thereof including a 3-methyl-2-thienyl group, 3,5-dimethyl-2-thienyl group, 3-chloro-2-thienyl group, 3-iodo-2-thienyl group and the like, when $R^a$ represents (A5), phenyl groups in which $R^5$ at 2-position represents a trifluoromethyl group, difluoromethyl group, methyl group, ethyl group or halogen atom are listed, examples thereof including a 2-trifluoromethylphenyl group, 2-difluoromethylphenyl group, 2-methylphenyl group, 2-ethylphenyl group, 2-fluorophenyl group, 2-chlorophenyl group, 2-bromophenyl group, 2-iodophenyl group, when $R^a$ represents (A6), 3-pyridyl groups in which $R^5$ at 2-position represents a trifluoromethyl group, difluoromethyl group, methyl group, ethyl group or halogen atom are listed, examples thereof including a 2-trifluoromethyl-3-pyridyl group, 2-difluoromethyl-3-pyridyl group, 2-methyl-3-pyridyl group, 2-ethyl-3-pyridyl group, 2-fluoro-3-pyridyl group, 2-chloro-3-pyridyl group, 2-bromo-3-pyridyl group and 2-iodo-3-pyridyl group, when $R^a$ represents (A7), examples thereof include a 2-chloromethyl-3-pyradinyl group, when $R^a$ represents (A8), 4-thienyl groups in which $R^5$ at 3-position represents a trifluoromethyl group, difluoromethyl group, methyl group, ethyl group or halogen atom are listed, examples thereof including a 3-trifluoromethyl-4-thienyl group, 3-difluoromethyl-4-thienyl group, 3-methyl-4-thienyl group, 3-ethyl-4-thienyl group, 3-fluoro-4-thienyl group, 3-chloro-4-thienyl group, 3-bromo-4-thienyl group and 3-iodo-4-thienyl group, when $R^a$ represents (A9), 3,4-dihydro-2H-pyran-5-yl groups in which $R^5$ at 6-position represents a trifluoromethyl group, difluoromethyl group, methyl group or ethyl group are listed, examples thereof including a 6-trifluoromethyl-3,4-dihydro-2H-pyran-5-yl group, 6-difluoromethyl-3,4-dihydro-2H-pyran-5-yl group, 6-methyl-3,4-dihydro-2H-pyran-5-yl group and 2-ethyl-3,4-dihydro-2H-pyran-5-yl group, and when $R^a$ represents (A10), 2,3-dihydro-1,4-oxathiin-5-yl groups, 2,3-dihydro-1,4-oxathiin-4-oxide-5-yl groups or 2,3-dihydro-1,4-oxathiin-4,4-dioxide-5-yl groups in which $R^5$ at 6-position represents a trifluoromethyl group, difluoromethyl group, methyl group or ethyl group are listed, examples thereof including a 6-methyl-2,3-dihydro-1,4-oxathiin-5-yl group, 6-methyl-2,3-dihydro-1,4-oxathiin-4-oxide-5-yl group, 6-methyl-2,3-dihydro-1,4-oxathiin-4,4-dioxide-5-yl group and the like. When $R^a$ represents (A11), 2,3-dihydro-4-furyl groups in which $R^5$ at 5-position represents a trifluoromethyl group, difluoromethyl group, methyl group or ethyl group are listed, examples thereof including a 5-trifluoromethyl-2,3-dihydro-4-furyl group, 5-difluoromethyl-2,3-dihydro-4-furyl group, 5-methyl-2,3-dihydro-4-furyl group and 5-ethyl-2,3-dihydro-4-furyl group, and when $R^a$ represents (A12), 4-isothiazolyl groups in which $R^5$ at 3-position represents a trifluoromethyl group, difluoromethyl group, methyl group, ethyl group or halogen atom are listed, examples thereof including a 3-trifluoromethyl-4-isothiazolyl group, 3-difluoromethyl-4-isothiazolyl group, 3-methyl-4-isothiazolyl group, 3-ethyl-4-isothiazolyl group, 3-fluoro-4-isothiazolyl group, 3-chloro-4-isothiazolyl group, 3-bromo-4-isothiazolyl group and 3-iodo-4-isothiazolyl group.

$R^b$ is a substituent in which $R^a$ is excluded from R.

A process for preparing a 2-alkyl-3-aminothiophene derivative and a method for producing a 3-aminothiophene derivative of the present invention will be described in detail below.

First, a reaction in which a secondary alkenyl group is introduced into 2-position of a 3-aminothiophene derivative and further this alkenyl group is converted to an alkyl group will be explained. For explaining this reaction in detail, it is divided into two steps and explained. However, the first step and the second step can also be conducted continuously, and the two-step reaction is not necessarily required.

In the first step reaction, a compound of the formula (2) is reacted with a compound of the formula (3) in the presence of an acid to produce a mixture of 2-alkenyl-3-aminothiophenes typified by the formulae (4a) to (4d).

First Step Reaction

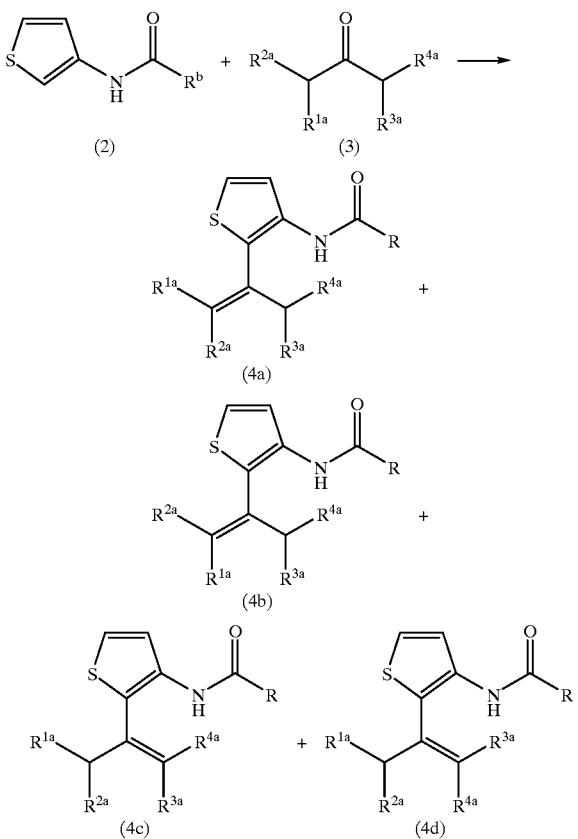

wherein, R, $R^{1a}$ to $R^{4a}$ are as defined above.

The mixture of 2-alkenyl-3-aminothiophenes typified by the formulae (4a) to (4d) is constituted by the 4 species of compounds at the maximum. For example, when $R^{1a}$ to $R^{4a}$ are all different in the compound represented by the formula (3), the mixture includes four compounds. When the compound represented by the formula (3) is 4-methyl-2-pentanone, the mixture comprises three compounds. And when the compound represented by the formula (3) is cyclohexanone, only one compound typified by the formulae (4a) to (4d) is obtained.

The use amount of a compound represented by the formula (3) in the first step reaction is usually from 0.5 to 100.0 mol, preferably from 1.0 to 30.0 mol, particularly preferable from 1.0 to 10.0 per 1 mol of a compound of the formula (2).

Examples of a solvent used if necessary in the first step reaction include aliphatic hydrocarbons such as hexane, petroleum ether and the like, aromatics such as benzene, toluene, chlorobenzene, anisole and the like, alcohols such as methanol, ethanol and the like, ethers such as dioxane, tetrahydrofuran, diethyl ether and the like, nitriles such as acetonitrile, propionitrile and the like, esters such as ethyl acetate and the like, and halogenated hydrocarbons such as dichloromethane, chloroform, 1,2-dichloroethane and the like, and mixed solvents thereof are also used. Also, a compound represented by the formula (3) can be used as a solvent. The use amount of a solvent in the first step reaction is usually from 0.1 to 200 ml, preferably from 1 to 50 ml, more preferably from 1 to 20 ml based on 1 g of a compound typified by the formula (2).

The first step reaction is conducted in the presence of an acid, and examples of the acid include mineral acids such as sulfuric acid, hydrochloric acid, hydrobromic acid, hydroiodic acid, phosphoric acid and the like, organic weak acids such as acetic acid, propionic acid and the like, organic strong acids such as p-toluenesulfonic acid, methanesulfonic acid and the like, solid acids such as zeolite and the like, Lewis acids such as aluminum chloride, zinc chloride and the like, ion-exchanged resins and the like. Preferable are a mineral acid such as sulfuric acid, hydrobromic acid and the like and an organic acid such as p-toluenesulfonic acid, methanesulfonic acid and the like, and particularly preferable are sulfuric acid and p-toluenesulfonic acid. The amount of these acids is usually from 0.001 to 10 mol, preferably from 0.01 to 1 mol based on 1 mol of a compound represented by the formula (2).

The reaction temperature in the first step reaction is usually from 0 to 300° C., preferably from 40 to 180° C., more preferably from 70 to 130° C., and the reaction time is usually from 0.1 to 100 hours, preferably from 1 to 36 hours.

Regarding various conditions in the first step reaction, namely, the use amounts of compounds of the general formulae (2) and (3), the kind and use amount of a solvent, the kind and use amount of an acid, the reaction temperature and the reaction time, numerical values within usual ranges, preferable ranges and more or particularly preferable ranges for respective conditions may be appropriately selected and combined.

Further, in the first step reaction water is formed with the compounds represented by the formulae (4a) to (4d). Removing the formed water, if necessary, can promote the progress of the reaction. Removing the formed water can be conducted by adding a drying agent such as magnesium sulfate anhydride, sodium sulfate anhydride or the like, or by carrying out azeotropic dehydration.

The reaction temperature in the first step reaction should be set at a temperature wherein the reaction can progress, and a catalyst used in the first step reaction should also be appropriately selected and used so that the reaction can progress. Further, as the catalyst used in the first step reaction, catalysts which can be used without problems at reaction temperatures at which the reaction can progress should be appropriately selected for use.

Among mixtures of 2-alkenyl-3-aminothiophene derivatives represented by the general formulae (4a) to (4d) which can be obtained in this first step reaction, the following is a mixture composed of novel compounds.

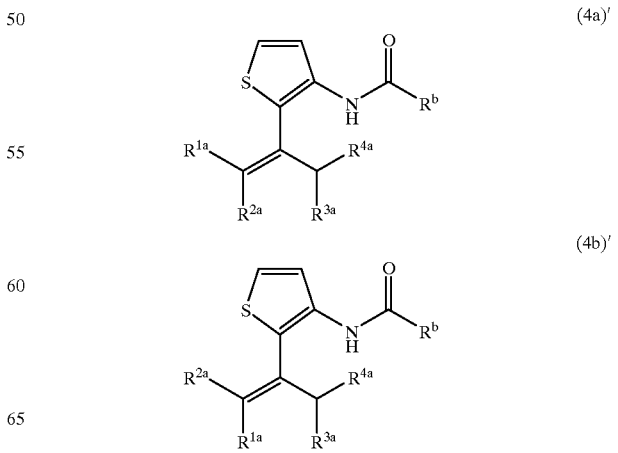

(4c)'

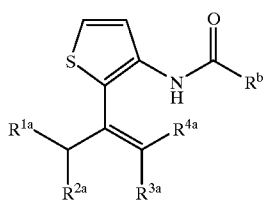

(4d)'

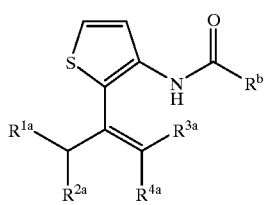

wherein, $R^b$ represents a hydrogen atom, alkyl group or alkoxy group which may be substituted, aromatic or non-aromatic hydrocarbon ring which may be substituted or aromatic or non-aromatic heterocyclic ring which may be substituted, and each of $R^{1a}$, $R^{2a}$, $R^{3a}$ and $R^{4a}$ independently represents a hydrogen atom, straight or branched alkyl group having 1 to 12 carbon atoms or straight or branched alkenyl group having 1 to 12 carbon atoms, and $R^{1a}$ and $R^{2a}$, $R^{3a}$ and $R^{4a}$, $R^{1a}$ and $R^{3a}$, $R^{1a}$ and $R^{4a}$, $R^{2a}$ and $R^{3a}$ or $R^{2a}$ and $R^{4a}$ may together form a cycloalkyl group, excepting the case in which R represents a group represented by any of the following (A1) to (A12):

(A1)

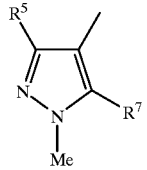

(A2)

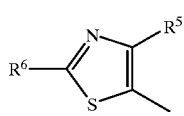

(A3)

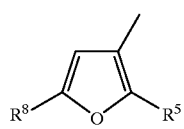

(A4)

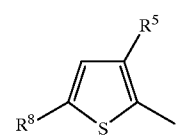

(A5)

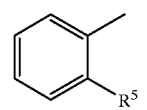

(A6)

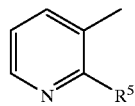

(A7)

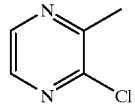

(A8)

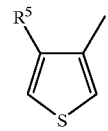

(A9)

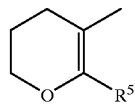

(A10)

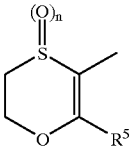

(A11)

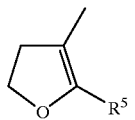

(A12)

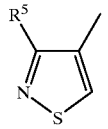

wherein, $R^5$ represents a trifluoromethyl group, difluoromethyl group, methyl group, ethyl group or halogen atom, $R^6$ represent a hydrogen atom, methyl group, trifluoromethyl group, halogen atom, methoxy group or amino group, $R^7$ represents a hydrogen atom, halogen atom, methyl group or methoxy group, $R^8$ represents a hydrogen atom, methyl group, ethyl group or halogen atom, and n represents an integer from 0 to 2 and herein, in the case of (A9), (A10) or (A11), $R^5$ is not a halogen atom, and the case in which R represents a tert-butoxy group and $R^{1a}$, $R^{2a}$, $R^{3a}$ and $R^{4a}$ all represent a hydrogen atom being excluded.

In the second step reaction, a mixture composed of compounds typified by the formulae (4a) to (4d) is reduced to produce a 2-alkyl-3-aminothiophene derivative represented by the formula (1).

Second Step Reaction

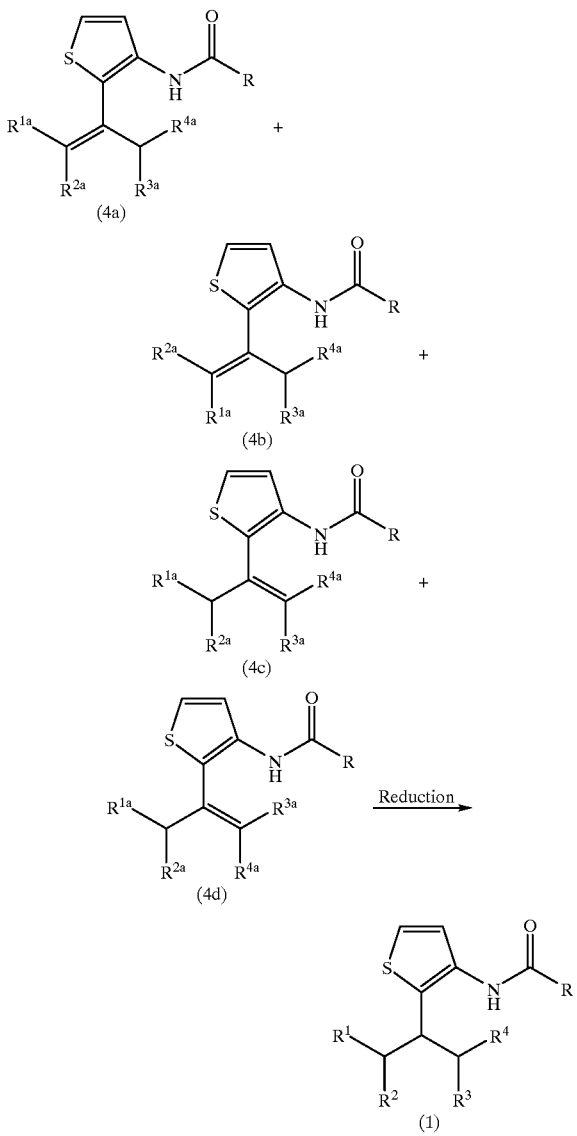

wherein R represents a hydrogen atom, alkyl group or alkoxy group which may be substituted, aromatic or non-aromatic hydrocarbon ring which may be substituted, aromatic or non-aromatic heterocyclic ring which may be substituted, each of $R^1$, $R^2$, $R^3$ and $R^4$ independently represents a hydrogen atom or straight or branched alkyl group having 1 to 12 carbon atoms, and $R^1$ and $R^2$, $R^3$ and $R^4$, $R^1$ and $R^3$, $R^1$ and $R^4$, $R^2$ and $R^3$ or $R^2$ and $R^4$ may together form a cycloalkyl group, each of $R^{1a}$, $R^{2a}$, $R^{3a}$ and $R^{4a}$ independently represents a hydrogen atom, straight or branched alkyl group having 1 to 12 carbon atoms or straight or branched alkenyl group having 1 to 12 carbon atoms, and $R^{1a}$ and $R^{2a}$, $R^{3a}$ and $R^{4a}$, $R^{1a}$ and $R^{3a}$, $R^{1a}$ and $R^{4a}$, $R^{2a}$ and $R^{3a}$ or $R^{2a}$ and $R^{4a}$ may together form a cycloalkyl group or cycloalkenyl group.

The reduction method is not particularly restricted, and there is usually applied a method in which a double bond is reduced to a single bond (for example, Shin Jikken Kagaku Koza, vol. 15, Oxidation and Reduction [II], Maruzen (1977)), and catalytic reduction is industrially preferable.

As a catalyst used in catalytic reaction, there can be used metal catalyst usually used in catalytic reduction, for example, nickel, palladium, platinum, rhodium, ruthenium, cobalt, chromium, copper, lead and the like. And these metals can be used as mixture. While these catalysts can be used in the form of metal, they are usually supported on a carrier such as carbon, barium sulfate, silica gel, aluminum, celite and the like, and alternatively, nickel, cobalt, copper and the like can be used in the form of a Raney catalyst.

The content of a catalyst used in catalytic reduction is usually from 3 to 20%, and the use amount is not particularly restricted and the catalyst is used in an amount of usually from 1 to 100% by weight, preferably from 1 to 30% by weight based on a mixture composed of compounds typified by the formulae (4a) to (4d).

Examples of a solvent used if necessary in the catalytic reduction reaction of the second step include alcohols such as methanol, ethanol and the like, aliphatic hydrocarbons such as hexane, petroleum ether and the like, aromatics such as benzene, toluene, anisole and the like, ethers such as dioxane, tetrahydrofuran, diethyl ether and the like, esters such as ethyl acetate and the like, aliphatic carboxylic acids such as acetic acid, propionic acid and the like, aprotic polar solvents such as dimethylformamide, dimethylsulfoxide and the like, and mixed solvents thereof are also used. The amount of a solvent in the second step reaction is usually from 0.1 to 200 ml, preferably from 2 to 20 ml based on 1 g of a mixture composed of compounds typified by the formulae (4a) to (4d).

The reaction temperature in the catalytic reduction of the second step reaction is usually from 0 to 300° C., preferably from 20 to 180° C., and the reaction time is usually from 0.5 to 100 hours, preferably from 1 to 48 hours.

The catalytic reduction reaction in the second step can be carried out under atmospheric pressure of hydrogen or under pressure of hydrogen. If the reaction is carried out under pressure, the pressure of hydrogen is from 0.098 to 30 MPa, preferably from 0.098 to 5.0 MPa.

Regarding various conditions in the catalytic reduction of the second step reaction, namely, the kind and use amount of a catalyst, the kind and use amount of a solvent, the reaction temperature and the reaction time, and the reaction pressure, numerical values within usual ranges and preferable ranges for respective conditions may be appropriately selected and combined.

Among mixtures of 2-alkyl-3-aminothiophene derivatives represented by the general formula (1b) which can be obtained in this second step reaction, the following is a novel compound.

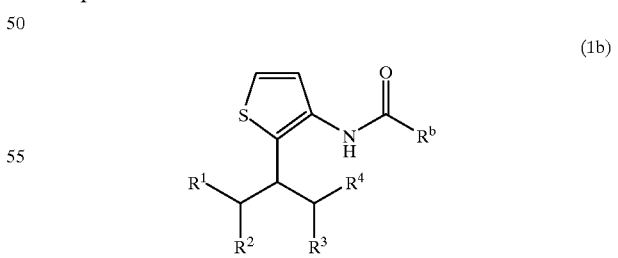

wherein $R^b$ represents a hydrogen atom, alkyl group or alkoxy group which may be substituted, aromatic or non-aromatic hydrocarbon ring which may be substituted or aromatic or non-aromatic heterocyclic ring which may be substituted. Each of $R^1$, $R^2$, $R^3$ and $R^4$ independently represents a hydrogen atom or straight or branched alkyl group having 1 to 12 carbon atoms, and $R^1$ and $R^2$, $R^3$ and $R^4$, $R^1$ and $R^3$, $R^1$ and $R^4$, $R^2$ and $R^3$ or $R^2$ and $R^4$ may together form a cycloalkyl group, excepting the case in which $R^b$ represents a group represented by any of the following (A1) to (A12):

(A1)
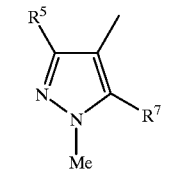

(A2)
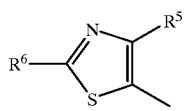

(A3)
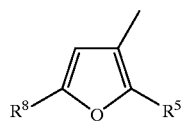

(A4)
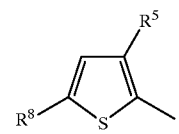

(A5)
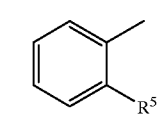

(A6)
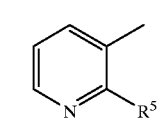

(A7)
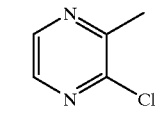

(A8)
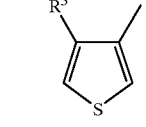

(A9)
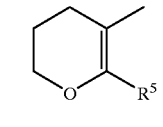

(A10)
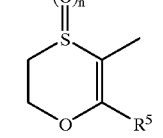

(A11)
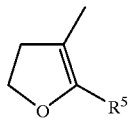

(A12)
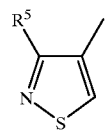

wherein $R^5$ represents a trifluoromethyl group, difluoromethyl group, methyl group, ethyl group or halogen atom, $R^6$ represents a hydrogen atom, methyl group, trifluoromethyl group, halogen atom, methoxy group or amino group, $R^7$ represents a hydrogen atom, halogen atom, methyl group or methoxy group, $R^8$ represents a hydrogen atom, methyl group, ethyl group or halogen atom, and n represents an integer from 0 to 2, and herein, in the case of (A9), (A10) or (A11), $R^5$ is not a halogen atom.

Then, a method for synthesizing a 3-aminothiophene derivative represented by the following formula (6):

(6)
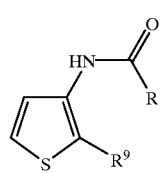

wherein $R^9$ represents a hydrogen atom, carboxyl group or alkoxycarbonyl group having 1 to 6 carbon atoms, R represents a hydrogen atom, alkyl group or alkoxy group which may be substituted, aromatic or non-aromatic hydrocarbon ring which may be substituted or aromatic or non-aromatic heterocyclic ring which may be substituted, which is an intermediate in the present invention will be described.

These compounds can be prepared for example by a method shown in the following reaction formula 1, and examples of the preparation method are not limited to this. The compound of the formula (6) includes compounds of formulae (2), (9) and (10).

Reaction formula 1

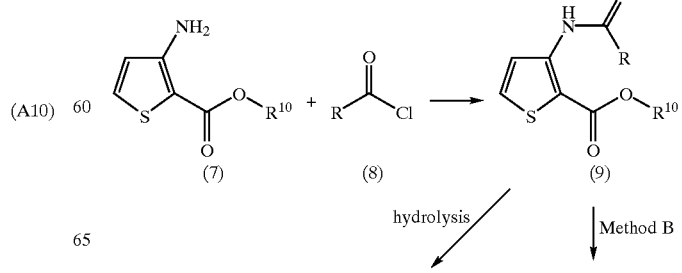

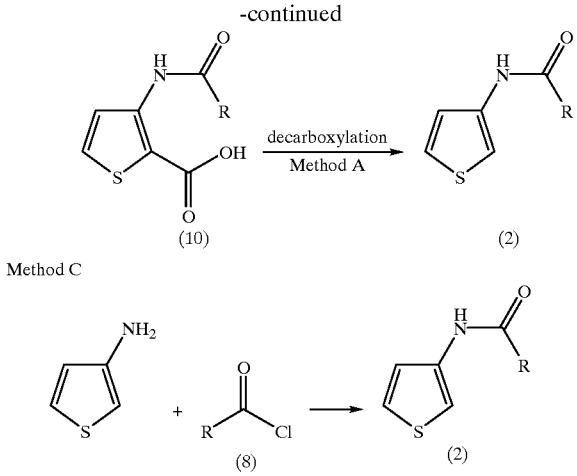

Method C wherein R is as defined above, the formula (9) means the case in which $R^9$ in the formula (6) is an alkoxycarbonyl group having 1 to 6 carbon atoms, the formula (10) means the case in which $R^9$ in the formula (6) is a carboxyl group, the formula (2) means the case in which $R^9$ in the formula (6) is a hydrogen atom, and $R^{10}$ represents an alkyl group having 1 to 6 carbon atoms. Examples of the alkyl group represented by $R^{10}$ include alkyl groups having 1 to 6 carbon atoms such as a methyl group, ethyl group, propyl group, isopropyl group, butyl group, tert-butyl group, hexyl group and the like.

A compound represented by the formula (9) can be prepared by reacting 3-aminothiophene-2-carboxylates represented by the formula (7) with a carboxylic acid halide represented by the formula (8) in melted condition or in a solvent. Raw materials, 3-aminothiophene-2-carboxylates represented by the formula (7) can be prepared by a known method, for example, a method described in SYNTHETIC COMMUNICATION, 9(8), 731 to 734 (1979).

The amount of a compound represented by the formula (8) in this reaction is usually from 0.2 to 20.0 mol, preferably from 0.5 to 5 mol per 1 mol of a compound of the formula (7).

Examples of a solvent used if necessary in this reaction include aliphatic hydrocarbons such as hexane, petroleum ether and the like, aromatics such as benzene, toluene, chlorobenzene, anisole and the like, ethers such as dioxane, tetrahydrofuran, diethyl ether and the like, nitrites such as acetonitrile, propionitrile and the like, esters such as ethyl acetate and the like, halogenated hydrocarbons such as dichloromethane, chloroform, 1,2-dichloroethane and the like, and aprotic polar solvents such as dimethylformamide, dimethylsulfoxide, 1,3-dimethyl-2-imidazolidinone and the like, and mixed solvents thereof are also used. The amount of a solvent in this reaction is usually from 0.1 to 200 ml, preferably from 1 to 20 ml based on 1 g of a compound represented by the formula (7).

This reaction may also be conducted in the presence of a base, and examples of the base include hydroxides of alkali metals and alkaline earth metals such as sodium hydroxide, potassium hydroxide, calcium hydroxide and the like, oxides of alkali metals and alkaline earth metals such as calcium oxide, magnesium oxide and the like, metal hydride of alkali metals and alkaline earth metals such as sodium hydride, calcium hydride and the like, alkali metal amides such as lithium amide, sodium amide and the like, carbonates of alkali metals and alkaline earth metals such as sodium carbonate, calcium carbonate, magnesium carbonate and the like, hydrogen carbonates of alkali metals and alkaline earth metals such as sodium hydrogen carbonate, potassium hydrogen carbonate and the like, alkylated alkali metals and alkaline earth metals such as methyl lithium, phenyl lithium, methyl magnesium chloride and the like, alkoxides of alkali metals and alkaline earth metals such as sodium methoxide, sodium ethoxide, potassium-t-butoxide, dimethoxy magnesium and the like, and various organic bases such as triethylamine, pyridine and the like. The amount of these bases is usually from 0.1 to 20.0 mol, preferably from 1 to 5.0 mol per 1 mol of carboxylic acid chlorides represented by the formula (8).

The reaction temperature is usually from −70 to 250° C., preferably from 0 to 150° C., and the reaction time is usually from 0.1 to 72 hours, preferably from 0.5 to 24 hours.

Regarding various conditions in this reaction, namely, the amounts of compounds of the formulae (7) and (8), the kind and amount of a solvent, the kind and use amount of a base, the reaction temperature and the reaction time, numerical values within usual ranges and preferable ranges for respective conditions may be appropriately selected and combined.

A compound represented by the formula (10) can be prepared by hydrolyzing an ester of a compound represented by the formula (9). The hydrolysis method is not particularly restricted, and there is usually applied a method in which an ester is hydrolyzed into a carboxylic acid (for example, Shin Jikken Kagaku Koza, vol. 14, Synthesis and Reaction of Organic Compound (II), Maruzen (1977)).

(Method A)

A compound represented by the formula (2) can be prepared by decarboxylating a compound represented by the formula (10).

This reaction can be conducted in a solvent or without solvent. Examples of a solvent used if necessary include alcohols such as methanol, ethanol, propanol, butanol, pentanol and the like, aromatic hydrocarbons such as benzene, toluene, xylene and the like, aprotic polar solvents such as dimethylformamide, dimethylsulfoxide, 1,3-dimethyl-2-imidazolidinone and the like, and basic solvents such as pyridine, quinoline and the like, and mixed solvents thereof are also used. The amount of a solvent in this reaction is usually from 0.1 to 200 ml, preferably from 1 to 20 ml based on 1 g of a compound represented by the general formula (10).

This reaction may also be conducted in the presence of a catalyst, and examples of the catalyst include mineral acids such as sulfuric acid, hydrochloric acid, hydrobromic acid, hydroiodic acid, phosphoric acid and the like, organic weak acids such as acetic acid, propionic acid and the like, organic strong acids such as p-toluenesulfonic acid, methanesulfonic acid and the like, metals such as copper and the like, and metal oxides such as copper oxide and the like. The use amount of these catalysts is usually from 0.1 to 100% by mol, preferably from 1 to 20% by mol based on a compound represented by the formula (10).

The reaction temperature of this reaction is usually from 0 to 400° C., preferably from 40 to 250° C., and the reaction time is usually from 0.01 to 240 hours, preferably from 0.1 to 72 hours.

Regarding various conditions in this reaction, namely, the amount of a compound represented by the formula (10), the kind and amount of a solvent, the kind and use amount of a catalyst, the reaction temperature and the reaction time, numerical values within usual ranges and preferable ranges for respective conditions may be appropriately selected and combined.

(Method B)

A compound represented by the formula (2) can also be prepared from a compound represented by the formula (9) in one step by a known method, for example, a method described in SYNTHESIS, 487(1981).

(Method C)

A compound represented by the formula (2) can also be prepared by reacting 3-aminothiophene with a carboxylic acid halide represented by the formula (8) under melted condition or in a solvent. Raw materials, 3-aminothiophene can be prepared by a known method, for example, a method described in SYNTHETIC COMMUNICATION, 25(23), 3729 to 3734 (1995).

Regarding 3-aminothiophene, an amino derivative may be reacted in the free form intact, and may also be reacted in the form of an acidic salt. Examples of the salt include salts of mineral acids such as hydrochlorides, sulfates, hydrobromides, hydroiodides, phosphates and the like, and organic acids such as acetates, oxalates and the like.

The amount of a compound represented by the formula (8) is usually from 0.2 to 20.0 mol, preferably from 0.5 to 5 mol per 1 mol of 3-aminothiophene.

Examples of a solvent used if necessary include aliphatic hydrocarbons such as hexane, petroleum ether and the like, aromatics such as benzene, toluene, chlorobenzene, anisole and the like, ethers such as dioxane, tetrahydrofuran, diethyl ether and the like, nitriles such as acetonitrile, propionitrile and the like, esters such as ethyl acetate and the like, halogenated hydrocarbons such as dichloromethane, chloroform, 1,2-dichloroethane and the like and aprotic polar solvents such as dimethylformamide, dimethylsulfoxide, 1,3-dimethyl-2-imidazolidinone and the like, and mixed solvents thereof are also used. The use amount of a solvent in this reaction is usually from 0.1 to 200 ml, preferably from 1 to 20 ml based on 1 g of 3-aminothiophene.

This reaction may also be conducted in the presence of a base, and examples of the base include hydroxides of alkali metals and alkaline earth metals such as sodium hydroxide, potassium hydroxide, calcium hydroxide and the like, oxides of alkali metals and alkaline earth metals such as calcium oxide, magnesium oxide and the like, hydrides of alkali metals and alkaline earth metals such as sodium hydride, calcium hydride and the like, alkali metal amides such as lithium amide, sodium amide and the like, carbonates of alkali metals and alkaline earth metals such as sodium carbonate, calcium carbonate, magnesium carbonate and the like, hydrogen carbonates of alkali metals and alkaline earth metals such as sodium hydrogen carbonate, potassium hydrogen carbonate and the like, alkylated alkali metals and alkaline earth metals such as methyl lithium, phenyl lithium, methyl magnesium chloride and the like, alkoxides of alkali metals and alkaline earth metals such as sodium methoxide, sodium ethoxide, potassium-t-butoxide, dimethoxy magnesium and the like, and various organic bases such as triethylamine, pyridine and the like. The amount of these bases is usually from 0.1 to 20.0 mol, preferably from 1 to 5.0 mol per 1 mol of carboxylic acid chlorides represented by the formula (8).

The reaction temperature is usually from −70 to 250° C., preferably from 0 to 150° C., and the reaction time is usually from 0.1 to 72 hours, preferably from 0.5 to 24 hours.

Regarding various conditions in this reaction, namely, the amounts of 3-aminothiophene and compounds represented by the general formula (8), the kind and amount of a solvent, the kind and amount of a base, the reaction temperature and the reaction time, numerical values within usual ranges and preferable ranges for respective conditions may be appropriately selected and combined.

Among 3-aminothiophene derivatives represented by the formula (6) which can be obtained by the above-described method shown in the reaction formula 1, the following is a novel compound.

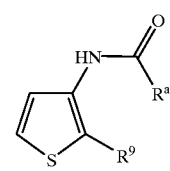

(6a)

wherein $R^9$ represents a hydrogen atom, carboxyl group or alkoxycarbonyl group having 1 to 6 carbon atoms, and $R^a$ represents a group represented by any of the following (A1) to (A12):

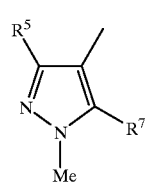

(A1)

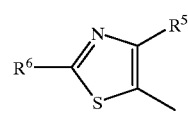

(A2)

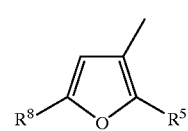

(A3)

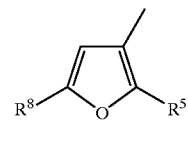

(A4)

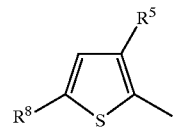

(A5)

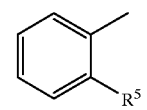

(A6)

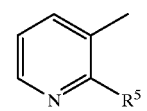

(A7)

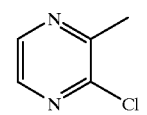

-continued

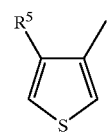
(A8)

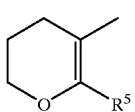
(A9)

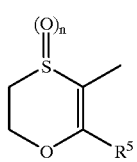
(A10)

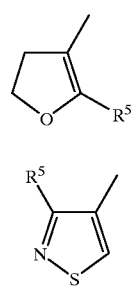
(A11)

(A12)

wherein $R^5$ represents a trifluoromethyl group, difluoromethyl group, methyl group, ethyl group or halogen atom, $R^6$ represents a hydrogen atom, methyl group, trifluoromethyl group, halogen atom, methoxy group or amino group, $R^7$ represents a hydrogen atom, halogen atom, methyl group or methoxy group, $R^8$ represents a hydrogen atom, methyl group, ethyl group or halogen atom, and n represents an integer from 0 to 2, and herein, in the case of (A9), (A10) or (A11), $R^5$ is not a halogen atom.

Then, a method for preparing 2-alkyl-3-aminothiophene represented by the formula (5) will be described.

Reaction formula 2

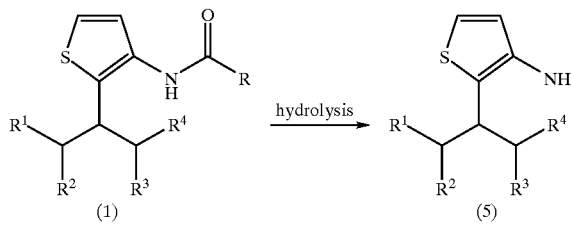

wherein R represents a hydrogen atom, alkyl group or alkoxy group which may be substituted, aromatic or non-aromatic hydrocarbon ring which may be substituted, aromatic or non-aromatic heterocyclic ring which may be substituted, each of $R^1$, $R^2$, $R^3$ and $R^4$ independently represents a hydrogen atom or straight or branched alkyl group having 1 to 12 carbon atoms, and $R^1$ and $R^2$, $R^3$ and $R^4$, $R^1$ and $R^3$, $R^1$ and $R^4$, $R^2$ and $R^3$ or $R^2$ and $R^4$ may together form a cycloalkyl group.

A compound represented by the formula (5) can be produced by hydrolyzing a compound represented by the formula (1) with an acid or alkali. The hydrolysis method is not particularly restricted, and there is usually applied a method in which an amide is hydrolyzed into amine (for example, Shin Jikken Kagaku Koza, vol. 14, Synthesis and Reaction of Organic Compound (II), Maruzen (1977)).

Then, a method for producing 2-alkyl-3-aminothiophene derivative represented by the general formula (1a) will be described.

Reaction formula 3

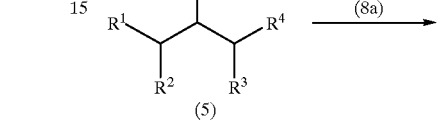

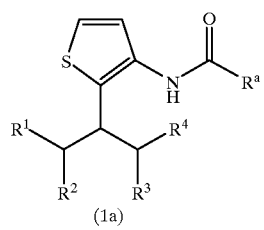

wherein $R^1$ to $R^4$, $R^a$ are as defined above.

A compound represented by the general formula (1a) can be prepared by reacting a compound represented by the formula (5) with a carboxylic acid halide represented by the formula (8a) under melted condition or in a solvent.

The amount of a compound represented by the formula (8a) is usually from 0.2 to 20.0 mol, preferably from 0.5 to 5 mol per 1 mol of a compound represented by the formula (5).

Examples of a solvent used if necessary include aliphatic hydrocarbons such as hexane, petroleum ether and the like, aromatics such as benzene, toluene, chlorobenzene, anisole and the like, ethers such as dioxane, tetrahydrofuran, diethyl ether and the like, nitriles such as acetonitrile, propionitrile and the like, esters such as ethyl acetate and the like, halogenated hydrocarbons such as dichloromethane, chloroform, 1,2-dichloroethane and the like and aprotic polar solvents such as dimethylformamide, dimethylsulfoxide, 1,3-dimethyl-2-imidazolidinone and the like, and mixed solvents thereof are also used. The amount of a solvent in this reaction is usually from 0.1 to 200 ml, preferably from 1 to 20 ml based on 1 g of a compound represented by the formula (5).

This reaction may also be conducted in the presence of a base, and examples of the base include hydroxides of alkali metals and alkaline earth metals such as sodium hydroxide, potassium hydroxide, calcium hydroxide and the like, oxides of alkali metals and alkaline earth metals such as calcium oxide, magnesium oxide and the like, hydrides of alkali metals and alkaline earth metals such as sodium hydride, calcium hydride and the like, alkali metal amides such as lithium amide, sodium amide and the like, carbonates of alkali metals and alkaline earth metals such as sodium carbonate, calcium carbonate, magnesium carbonate and the like, hydrogen carbonates of alkali metals and alkaline earth metals such as sodium hydrogen carbonate, potassium hydrogen carbonate and the like, alkylated alkali metals and alkaline earth metals such as methyl lithium, phenyl lithium, methyl magnesium chloride and the like, alkoxides of alkali metals and alkaline earth metals such as sodium methoxide, sodium ethoxide, potassium-t-butoxide, dimethoxy magnesium and the like, and various organic bases such as triethylamine, pyridine and the like. The use amount of these bases is usually from 0.1 to 20.0 mol. preferably from 1 to 5.0 mol per 1 mol of carboxylic acid chlorides represented by the formula (8a).

The reaction temperature is usually from −70 to 250° C., preferably from 0 to 150° C., and the reaction time is usually from 0.1 to 72 hours, preferably from 0.5 to 24 hours.

Regarding various conditions in this reaction, namely, the use amounts of compounds represented by the formulae (5) and (8a), the kind and use amount of a solvent, the kind and use amount of a base, the reaction temperature and the reaction time, numerical values within usual ranges and preferable ranges for respective conditions may be appropriately selected and combined.

EXAMPLE

The following examples further specifically illustrate the present invention but do not limit the scope of the present invention.

Reference Example 1

Reaction of 3-aminothiophene with 4-methyl-2-pentanone 0.15 g of p-toluenesulfonic acid monohydrate and 1.61 g (16.1 mmol) of 4-methyl-2-pentanone were charged into 5 ml of methylene chloride, cooled to 5° C., then, 0.53 g (5.35 mmol) of 3-aminothiophene was added dropwise. The mixture was stirred for 1 hour at 5° C. to find no progress of the reaction. Therefore, the reaction temperature was raised to 25° C. and the mixture was stirred for 1 hour. Since the reaction did not progress at all, stirring under reflux was conducted to find decomposition of 3-aminothiophene.

Example 1

Synthesis of N-{3-(2-methoxycarbonyl)-thienyl}-3-trifluoromethyl-1-methylpyrazole-4-carboxamide (compound 1.1)

9.53 g (60.7 mmol) of methyl 3-aminothiophene-2-carboxylate and 9.60 g (121.4 mmol) of pyridine were charged into 63 ml of tetrahydrofuran, then the mixture was cooled to 10° C., and to the mixture was added 12.9 g (60.7 mmol) of 3-trifluoromethyl-1-methylpyrazole-4-carbonyl chloride dropwise at a temperature of 18° C. or lower. After stirring the mixture at 25° C. for 3 hours, ethyl acetate was added, and the mixture was washed sequentially with a 5% aqueous hydrochloric acid solution, saturated aqueous sodium hydrogen carbonate solution and saturated sodium chloride solution. After drying over anhydrous sodium sulfate, the solvent was distilled off under reduced pressure, and the resultant residue was crystallized out from hexane to obtain 20.1 g of the intended compound as a colorless crystal (yield: 99%). The 3-trifluoromethyl-1-methylpyrazole-4-carbonyl chloride herein used had been obtained by preparing ethyl 3-trifluoromethyl-1-methylpyrazole-4-carboxylate by a method described in DE4231517, then, hydrolyzing it by an ordinary method and acid-chlorinating the hydrolysate.

Example 2

Synthesis of N-{3-(2-carboxy)thienyl}-3-trifluoromethyl-1-methylpyrazole-4-carboxamide (compound 8.1)

15.6 g (46.8 mmol) of the N-{3-(2-methoxycarbonyl)-thienyl}-3-trifluoromethyl-1-methylpyrazole-4-carboxamide obtained in Example 1 and 3.74 g (93.7 mmol) of sodium hydroxide were charged into a mixed solvent comprising 60 ml of methanol, 40 ml of water and 10 ml of dioxane, and the mixture was stirred at 25° C. for 5 hours. To this was added 7.8 ml of concentrated hydrochloric acid to control pH at about 4, then, methanol and dioxane were distilled off under reduced pressure, and 1 ml of concentrated hydrochloric acid was added to control pH at 1. The deposited crystal was filtrated, then, washed with 30 ml of water three times and dried under reduced pressure to obtain 14.7 g of the intended compound (yield: 99%).

Example 3

Synthesis of N-(3-thienyl)-3-trifluoromethyl-1-methyl-pyrazole-4-carboxamide (compound 15.1) (Method A)

2.0 g (6.27 mmol) of the N-{3-(2-carboxy)thienyl}-3-trifluoromethyl-1-methylpyrazole-4-carboxamide obtained in Example 2 was heated to 215° C. without using a solvent, and stirred for 10 minutes in the same condition. It was cooled to room temperature to obtain 1.57 g of the intended compound as a brown crystal (yield: 91%)

Example 4

Synthesis of N-(3-thienyl)-3-trifluoromethyl-1-methyl-pyrazole-4-carboxamide (compound 15.1) (Method C)

65.0 g (0.451 mol) of 3-aminothiophene 1/2 oxalate was charged into 455 ml of tetrahydrofuran, and the mixture was cooled to 10° C. under nitrogen flow. 74.9 g (0.948 mol) of pyridine and 67.2 g (0.316 mol) of 3-trifluoromethyl-1-methylpyrazole-4-carbonyl chloride were added dropwise sequentially at 18° C., and the mixture was stirred for 2 hours at 25° C. The reaction solution was discharged into 1500 ml of water, then, tetrahydrofuran was distilled off under reduced pressure. The deposited crystal was filtrated, then, washed with 100 ml of water three times and dried under reduced pressure to obtain 73.9 g of the intended compound (yield: 85% (based on carbonyl chloride)) as a crystal. The 3-trifluoromethyl-1-methylpyrazole-4-carbonyl chloride herein used had been obtained by producing ethyl 3-trifluoromethyl-1-methylpyrazole-4-carboxylate by a method described in DE4231517, then, hydrolyzing it by an ordinary method and acid-chlorinating the hydrolysate.

Example 5

Synthesis of N-(3-thienyl)-3-trifluoromethyl-1-methyl-pyrazole-4-carboxamide (compound 15.1) (Method B)

5.0 g (15.0 mmol) of the N-{3-(2-methoxycarbonyl)-thienyl}-3-trifluoromethyl-1-methylpyrazole-4-carboxamide obtained in Example 1 and 1.91 g (16.5 mmol) of pyridine hydrochloride were charged into 25 ml of pyridine, and the mixture was stirred for 42 hours at 120° C. The mixture was cooled to room temperature, then, pyridine was distilled off under reduced pressure to obtain 12.1 g of an oil. This oil was discharged into 200 ml of water, and the deposited crystal was filtrated. This crystal was washed with 10 ml of water three times and dried under reduced pressure to obtain 3.88 g of the intended compound (yield: 94%) as a crystal.

Example 6

Synthesis of N-[3-{2-(1,3-dimethylbutyl)}thienyl]-3-trifluoromethyl-1-methylpyrazole-4-carboxamide 20.0 g (72.7 mmol) of the N-(3-thienyl)-3-trifluoromethyl-1-methylpyrazole-4-carboxamide obtained in Example 4, 21.9 g (218.2 mmol) of 4-methyl-2-pentanone and 1.0 g of p-toluenesulfonic acid monohydrate were charged into 160 ml of toluene, and the mixture was stirred with heating at 112° C. for 8 hours while extracting water producing in the reaction out of the system. After cooling to 50° C., the solution was washed with a saturated aqueous sodium hydrogen carbonate solution and dried over sodium sulfate. The solvent was distilled off under reduced pressure, then, the resulted residue was purified by silica gel column chromatography (eluent: hexane/ethyl acetate=6/4) to obtain 24.1 g of a mixture as a colorless crystal.

1.0 g (2.80 mmol) of this mixture and 0.2 g of 5% palladium carbon (Degussa chemical catalyst E106R/W) were charged into 10 ml of methanol, and catalytic reduction was conducted at 25° C. for 9 hours at normal pressure. The palladium carbon was filtrated, and methanol in the filtrate was distilled off under reduced pressure, then, ethyl acetate was added to the residue. After washing with water, the organic layer was dried over anhydrous sodium sulfate, and the solvent was distilled off under reduced pressure to obtain 1.0 g of the intended compound as a colorless crystal (yield: 91%).

$^1$H-NMR (CDCl$_3$, σ value, J=Hz): 0.86 (6H, d, J=6.8), 1.25 (3H, d, J=6.8), 1.43–1.64 (3H, m), 3.08 (1H, sext, J=6.8), 3.99 (3H, s), 7.12 (1H, d, J=5.1), 7.43 (1H, d, J=5.1), 7.53 (1H, brs), 8.05 (1H, s).

m.p.: 107 to 108° C.

Example 7

Synthesis of N-[3-{2-(1-methylpropyl)}thienyl]-3-trifluoromethyl-1-methylpyrazole-4-carboxamide The title compound was synthesized in the same manner as in Example 6 except that methyl ethyl ketone was used instead of 4-methyl-2-pentanone (yield: 70%).

$^1$H-NMR (CDCl$_3$, σ value, J=Hz): 0.89 (3H, d, J=7.3), 1.30 (3H, d, J=7.3), 1.59–1.69 (2H, m), 2.85–2.93 (1H, m), 3.99 (3H, s), 7.13 (1H, d, J=5.1), 7.46 (1H, d, J=5.1), 7.54 (1H, brs), 8.05 (1H, s).

m.p.: 112 to 114° C.

Example 8

Synthesis of N-{3-(2-cyclohexyl)thienyl}-3-trifluoromethyl-1-methylpyrazole-4-carboxamide The title compound was synthesized in the same manner as in Example 6 except that cyclohexanone was used instead of 4-methyl-2-pentanone (yield: 68%).

$^1$H-NMR (CDCl$_3$, σ value, J=Hz): 1.22–1.49 (5H, m), 1.72–1.94 (5H, m), 2.72–2.79 (1H, m), 3.99 (3H, s), 7.10 (1H, d, J=5.1), 7.51 (1H, d, J=5.1), 7.60 (1H, brs), 8.06 (1H, s).

m.p.: 128.7 to 129.5° C.

Reference Example 2

Synthesis of N-{3-(2-methoxycarbonyl)thienyl}-benzamide 31.4 g (0.200 mol) of methyl 3-aminothiophene-2-carboxylate was charged into 97.2 g of toluene, and the mixture was heated to 90° C. 29.5 g (0.210 mol) of benzoyl chloride was added dropwise over 20 minutes while keeping the reflux temperature, and the mixture was stirred for 4 hours under reflux. After cooling to room temperature, 100 ml of toluene was added, and the mixture was washed sequentially with a saturated aqueous sodium hydrogen carbonate solution and a saturated sodium chloride solution. The solution was dried over anhydrous magnesium sulfate, then, the solvent was distilled off under reduced pressure to obtain 52.0 g of the intended compound as a crystal (yield: 100%).

$^1$H-NMR (CDCl$_3$, ppm, J=Hz): 3.94 (3H, s), 7.49–7.61 (5H, m), 8.00–8.05 (2H, m), 8.31 (1H, d, J=5.3)

m.p.: 101.4 to 102.3° C.

Reference Example 3

Synthesis of N-{3-(2-carboxy)thienyl}-benzamide 50.0 g (0.192 mol) of the N-{3-(2-methoxycarbonyl)-thienyl}-benzamide obtained in Reference Example 2 was charged into 300 ml of ethanol, and to this was added dropwise 15.4 g (0.385 mol) of sodium hydroxide dissolved in 150 ml of water. The mixture was stirred for 4 hours at room temperature, then, cooled to 10° C., and 30 ml of concentrated hydrochloric acid was added dropwise to control pH at about 6. Methanol was distilled off under reduced pressure, then, 100 ml of water was charged into the resulted residue, and 10 ml of concentrated hydrochloric acid was added to control pH at 1. The deposited crystal was filtrated, and washed with 50 ml of water three times. The resulting crystal was dried under reduced pressure to obtain 45.0 g of the intended compound as a colorless crystal (yield: 95%).

$^1$H-NMR (DMSO-d$_6$, ppm, J=Hz): 7.56–7.69 (3H, m), 7.91–7.94 (3H, m), 8.09 (1H, d, J=5.7), 11.2 (1H, brs)

m.p.: 214.6 to 214.9° C.

Reference Example 4

Synthesis of N-(3-thienyl)-benzamide (Method A)

30.0 g (12.1 mmol) of the N-{3-(2-carbonyl)thienyl}-benzamide obtained in Reference Example 3 and 1.5 g of p-toluenesulfonic acid monohydrate were charged into 120 ml of 1,3-dimethyl-2-imidazolydinone, and the mixture was stirred at 130° C. for 27 hours. After cooled to room temperature, the solution was discharged into 1000 ml of water. The deposited crystal was filtrated, and washed with 30 ml of water three times. The resulting crystal was dried under reduced pressure to obtain 20.8 g of the intended compound as a crystal (yield: 85%).

$^1$H-NMR (CDCl$_3$, ppm, J=Hz): 7.12–7.14 (1H, m), 7.28–7.29 (1H, m), 7.44–7.58 (3H, m), 7.73 (1H, dd, J=2.9, 0.6), 7.84–7.88 (2H, m), 8.20 (1H, brs)

m.p.: 155.4 to 156.2° C.

Example 9

Synthesis of mixture of N-[3-{2-(E)-(4-methyl-2-penten-2-yl)}thienyl]-benzamide, N-[3-{2-(Z)-(4-methyl-2-penten-2-yl)}thienyl]-benzamide, and N-[3-{2-(4-methyl-1-penten-2-yl)}thienyl]-benzamide (mixture 115.3)

20.0 g (0.0985 mol) of the N-(3-thienyl)-benzamide obtained in Reference Example 4, 29.6 g (0.296 mol) of 4-methyl-2-pentanone and 1.0 g of p-toluenesulfonic acid monohydrate were charged into 200 ml of toluene, and the mixture was stirred with heating at 111° C. for 9.5 hours while extracting water producing in the reaction out of the system. After cooling to room temperature, the solution was washed with a 1N aqueous sodium hydroxide solution and saturated sodium chloride solution sequentially, then, dried over sodium sulfate. The solvent was distilled off under reduced pressure, then, the resulted residue was purified by silica gel column chromatography (eluent: hexane: ethyl acetate=9:1) to obtain 26.1 g of the intended mixture as a colorless crystal (yield: 93%).

Example 10

Synthesis of N- [3-{2- (1,3-dimethylbutyl)}thienyl]-benzamide (compound 114.3)

24.0 g (84.2 mmol) of the mixture N-[3-{2-(E)-(4-methyl-2-penten-2-yl)}thienyl]-benzamide, N-[3-{2-(Z)-(4-methyl-2-penten-2-yl)}thienyl]-benzamide, and N-[3-{2-(4-methyl-1-penten-2-yl)}thienyl]-benzamide obtained in Example 9, 4.8 g of 5% palladium carbon (Degussa chemical catalyst E106R/W) and 120 ml of methanol were charged into 200 ml autoclave, purged with nitrogen, then, a hydrogenation reaction was conducted for 11 hours under conditions of a temperature of 40° C. and a hydrogen pressure of 1.96 MPa. After purging with nitrogen, the catalyst was filtrated off, and the filtrate was distilled off under reduced pressure to obtain 23.5 g of the intended compound as a colorless crystal (yield: 97%).

Example 11

Synthesis of 3-amino-2-(1,3-dimethylbutyl) thiophene 21.8 g (76.0 mmol) of the N-[3-{2-(1,3-dimethyl-butyl)}thienyl]-benzamide obtained in Example 10 was charged into a mixed solution composed of 100 ml of concentrated hydrochloric acid and 70 ml of acetic acid, and the reaction was conducted with heating under reflux at 97° C. for 27 hours. After cooling to room temperature, the solution was neutralized with a 10N aqueous sodium hydroxide solution while charging ice. After extracting with ethyl acetate twice, the solution was washed with a saturated sodium chloride solution, and dried over magnesium sulfate. The solvent was distilled off under reduced pressure to obtain 13.3 g of the intended compound as an oil (yield: 96%).

$^1$H-NMR (CDCl$_3$, σ value, J=Hz): 0.89 (3H, d, J=6.6), 0.90 (3H, d, J=6.6), 1.23 (3H, d, J=6.6), 1.35–1.65 (3H, m), 2.95 (1H, sext, J=6.6), 3.35 (2H, brs), 6.55 (1H, d, J=5.1), 6.95 (1H, d, J=5.1)

Physical condition: oil

Example 12

Synthesis of N-[3-{2-(1,3-dimethylbutyl)}thienyl]-3-trifluoromethyl-1-methylpyrazole-4-carboxamide 0.50 g (2.73 mmol) of the 3-amino-2-(1,3-dimethyl-butyl) thiophene obtained in Example 11 and 0.26 g (3.28 mmol) of pyridine were charged into 3 ml of tetrahydrofuran, and the mixture was cooled to 10° C. 0.64 g (3.00 mmol) of 3-trifluoromethyl-1-methylpyrazole-4-carbonyl chloride was added dropwise while keeping the reaction temperature under 18° C. The mixture was stirred for 2 hours at room temperature, then, discharged into a 5% aqueous hydrochloric acid solution and extracted with ethyl acetate. The ethyl acetate layer was washed with a saturated aqueous sodium hydrogen carbonate solution and a saturated sodium chloride solution, then, dried over anhydrous magnesium sulfate. The solvent was distilled off under reduced pressure, then, the resulting residue was crystallized out from hexane to obtain 0.93 g of the intended compound as a crystal (yield: 95%). The 3-trifluoromethyl-1-methylpyrazole-4-carbonyl chloride herein used had been obtained by producing ethyl 3-trifluoromethyl-1-methylpyrazole-4-carboxylate by a method described in DE4231517, then, hydrolyzing it by an ordinary method and acid-chlorinating the hydrolysate.

$^1$H-NMR (CDCl$_3$, σ value, J=Hz): 0.86 (6H, d, J=6.8), 1.25 (3H, d, J=6.8), 1.43–1.64 (3H, m), 3.08 (1H, sext, J=6.8), 3.99 (3H, s), 7.12 (1H, d, J=5.1), 7.43 (1H, d, J=5.1), 7.53 (1H, brs), 8.05 (1H, s).

m.p.: 107 to 108° C.

Reference Example 5

Synthesis of methyl 3-isopropoxycarbonylaminothiophene-2-carboxylate 22.1 g (0.141 mol) of methyl 3-aminothiophene-2-carboxylate was dissolved in 100 ml of ethyl acetate, and to this was added 11.7 g (0.148 mol) of pyridine. 18.1 g (0.148 mol) of isopropyl chloroformate was added dropwise while cooling with ice over 30 minutes. After completion of the addition, the solution was heated to 60° C. and stirred with heating for 3 hours. After completion of the reaction, the reaction solution was washed sequentially with a 5% aqueous hydrochloric acid solution, saturated aqueous sodium hydrogen carbonate solution and saturated sodium chloride solution, and dried over anhydrous sodium sulfate. The solvent was distilled off under reduced pressure, and the resulting residue was purified by silica gel column chromatography (eluent: hexane/ethyl acetate=7/3) to obtain 30.6 g of the intended compound as a crystal (yield: 85%). The crystal herein obtained was not analyzed and used for the next reaction.

Reference Example 6

Synthesis of 3-isopropoxycarbonyl-aminothiophene (Method B)

30.8 g (0.126 mol) of the methyl 3-isopropoxy-carbonylaminothiophene-2-carboxylate obtained in Reference Example 5 and 16.1 g (0.139 mol) of pyridine hydrochloride were charged into 70 ml of pyridine, and the mixture was heated to 130° C., and stirred with heating for 45 hours. After cooling to room temperature, pyridine was distilled off under reduced pressure, and into the resulted residue was charged 300 ml of ethyl acetate. The ethyl acetate layer was washed with water, then, dried over magnesium sulfate. The solvent was distilled off under reduced pressure, and the resulted residue was purified by silica gel column chromatography (eluent: hexane/ethyl acetate=2/1) to obtain 21.0 g of the intended compound as a colorless crystal (yield: 90%).

$^1$H-NMR (CDCl$_3$, ppm, J=Hz): 1.29 (6H, d, J=6.3), 5.01 (1H, sept, J=6.3), 6.80 (1H, brs), 6.92–6.94 (1H, m), 7.19–7.26 (2H, m).

m.p.: 105.0 to 107.2° C.

Example 13

Synthesis of mixture of 3-isopropoxycarbonylamino-{2-(E)-(4-methyl-2-penten-2-yl)}thiophene, 3-isopropoxycarbonyl-amino-{2-(Z)-(4-methyl-2-penten-2-yl)}thiophene, and 3-isopropoxycarbonylamino-{2-(4-methyl-1-penten-2-yl)}thiophene (mixture 115.5)

(15.4 mmol) of the 3-isopropoxycarbonylaminothiophene obtained in Reference Example 6, 4.60 g (46.0 mmol) of 4-methyl-2-pentanone and 0.14 g of p-toluenesulfonic acid monohydrate were charged into 20 ml of toluene, and the mixture was heated under reflux for 7 hours while extracting water producing in the reaction out of the system. After cooling to room temperature, the solution was washed with a saturated aqueous sodium hydrogen carbonate solution, and dried over sodium sulfate. The solvent was distilled off under reduced pressure, then, the resulting residue was purified by silica gel column chromatography (eluent/hexane:ethyl acetate=20/1) to obtain 3.68 g of the intended mixture as an oil (yield: 89%).

Example 14

Synthesis of 3-isopropoxycarbonyl-{2-(1,3-dimethylbutyl)}-thiophene (compound 114.5)

b 2.06g (7.72 mmol) of the mixture of 3-isopropoxy-carbonylamino-{2-(E)-(4-methyl-2-penten-2-yl)}thiophene, 3-isopropoxycarbonylamino-{2-(Z)-(4-methyl-2-penten-2-yl)}thiophene, and 3-isopropoxycarbonylamino-{2-(4-methyl-1-penten-2-yl)}thiophene obtained in Example 13 and 0.41 g of 5% palladium carbon (Degussa chemical catalyst E106R/W) were charged into 20 ml of methanol, and after nitrogen purge, a hydrogenation reaction was conducted at normal pressure under hydrogen atmosphere for 9 hours. After nitrogen purge, the catalyst was filtrated off, and the solvent was distilled off under reduced pressure. The resulting residue was purified by silica gel column chromatography (eluent: hexane/ethyl acetate=9/1) to obtain 1.61 g of the intended compound as a colorless crystal (yield: 70%).

Example 15

Synthesis of 3-amino-2-(1,3-dimethylbutyl) thiophene 1.24 g (4.61 mmol) of the 3-isopropoxycarbonyl-{2-(1,3-dimethylbutyl)}thiophene obtained in Example 14 and 1.36 g (34.0 mmol) of sodium hydroxide were charged into a mixture of 5 ml of methanol, 4 ml of water and 5 ml of dioxane, and the mixture was heated under reflux for 8 hours. The solvent was distilled off under reduced pressure, then, extracted with diethyl ether twice, and washed with a saturated sodium chloride solution. The solvent was distilled off under reduced pressure, and the resulting residue was purified by silica gel column chromatography (eluent: hexane/ethyl acetate=9/1) to obtain 0.42 g of the intended compound as a brown oil (yield: 50%).

$^1$H-NMR (CDCl$_3$, σ value, J=Hz): 0.89 (3H, d, J=6.6), 0.90 (3H, d, J=6.6), 1.23 (3H, d, J=6.6), 1.35–1.65 (3H, m), 2.95 (1H, sext, J=6.6), 3.35 (2H, brs), 6.55 (1H, d, J=5.1), 6.95 (1H, d, J=5.1).

Physical condition: oil

Example 16

Synthesis of N-[3-{2-(1,3-dimethylbutyl)thienyl}]-3-trifluoromethyl-1-methylpyrazole-4-carboxylic amide 0.25 g (1.36 mmol) of the 3-amino-2-(1,3-dimethylbutyl) thiophene obtained in Example 15 and 0.13 g (1.64 mmol) were charged into 3 ml of tetrahydrofuran, and the mixture was cooled to 10° C. 0.32 g (1.50 mmol) of 3-trifluoromethyl-1-methylpyrazole-4-carbonyl chloride was added dropwise while keeping the reaction temperature under 18° C. The mixture was stirred for 2 hours at room temperature, then, discharged into a 5% aqueous hydrochloric acid solution and extracted with ethyl acetate. The ethyl acetate layer was washed with a saturated aqueous sodium hydrogen carbonate solution and a saturated sodium chloride solution, then, dried over anhydrous magnesium sulfate. The solvent was distilled off under reduced pressure, then, the resulting residue was crystallized out from hexane to obtain 0.46 g of the intended compound as a crystal (yield: 94%). The 3-trifluoromethyl-1-methylpyrazole-4-carbonyl chloride herein used had been obtained by producing ethyl 3-trifluoromethyl-1-methylpyrazole-4-carboxylate by a method described in DE4231517, then, hydrolyzing it by an ordinary method and acid-chlorinating the hydrolysate.

hu 1H-NMR (CDCl$_3$, σ value, J=Hz): 0.86 (6H, d, J=6.8), 1.25 (3H, d, J=6.8), 1.43–1.64 (3H, m), 3.08 (1H, sext, J=6.8), 3.99 (3H, s), 7.12 (1H, d, J=5.1), 7.43 (1H, d, J=5.1), 7.53 (1H, brs), 8.05 (1H, s).

m.p.: 107 to 108° C.

Examples of a compound of the formula (6a) which is an intermediate of the present invention are summarized in the following Tables 1.

In table 1, a solvent for measurement of NMR is DMSO-d$_6$, when R$^9$ is carboxy group.

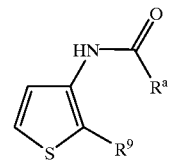

(6a)

TABLE 1

| Compound No. | R$^9$ | Ar | m.p. (° C.) | $^1$H—NMR(270 MHz) (CDCl$_3$, δ value, J:Hz) |
|---|---|---|---|---|
| 1.1 | CO$_2$CH$_3$ | A1 (R$^5$ = CF$_3$, R$^7$ = H) | 144.1~ 144.9 | 3.92(3H, s), 4.03(3H, s), 7.51(1H, d, J=5.6), 7.96(1H, s) 8.19(1H, d, J=5.6), 10.68(1H, brs) |
| 1.2 | CO$_2$CH$_3$ | A1 (R$^5$ = CHF$_2$, R$^7$ = H) | | |
| 1.3 | CO$_2$CH$_3$ | A1 (R$^5$ = CH$_3$, R$^7$ = H) | | |
| 1.4 | CO$_2$CH$_3$ | A1 (R$^5$ = C$_2$H$_5$, R$^7$ = H) | | |
| 1.5 | CO$_2$CH$_3$ | A1 (R$^5$ = F, R$^7$ = H) | | |

TABLE 1-continued

| Compound No. | $R^9$ | Ar | m.p. (° C.) | $^1$H—NMR(270 MHz) (CDCl$_3$, δ value, J:Hz) |
|---|---|---|---|---|
| 1.6 | CO$_2$CH$_3$ | A1 ($R^5$ = Cl, $R^7$ = H) | | |
| 1.7 | CO$_2$CH$_3$ | A1 ($R^5$ = Br, $R^7$ = H) | | |
| 1.8 | CO$_2$CH$_3$ | A1 ($R^5$ = I, $R^7$ = H) | | |
| 2.1 | CO$_2$CH$_3$ | A1 ($R^5$ = CF$_3$, $R^7$ = F) | | |
| 2.2 | CO$_2$CH$_3$ | A1 ($R^5$ = CHF$_2$, $R^7$ = F) | | |
| 2.3 | CO$_2$CH$_3$ | A1 ($R^5$ = CH$_3$, $R^7$ = F) | | |
| 2.4 | CO$_2$CH$_3$ | A1 ($R^5$ = C$_2$H$_5$, $R^7$ = F) | | |
| 2.5 | CO$_2$CH$_3$ | A1 ($R^5$ = F, $R^7$ = F) | | |
| 2.6 | CO$_2$CH$_3$ | A1 ($R^5$ = Cl, $R^7$ = F) | | |
| 2.7 | CO$_2$CH$_3$ | A1 ($R^5$ = Br, $R^7$ = F) | | |
| 2.8 | CO$_2$CH$_3$ | A1 ($R^5$ = I, $R^7$ = F) | | |
| 3.1 | CO$_2$CH$_3$ | A1 ($R^5$ = CF$_3$, $R^7$ = Cl) | | |
| 3.2 | CO$_2$CH$_3$ | A1 ($R^5$ = CHF$_2$, $R^7$ = Cl) | | |
| 3.3 | CO$_2$CH$_3$ | A1 ($R^5$ = CH$_3$, $R^7$ = Cl) | | |
| 3.4 | CO$_2$CH$_3$ | A1 ($R^5$ = C$_2$H$_5$, $R^7$ = Cl) | | |
| 3.5 | CO$_2$CH$_3$ | A1 ($R^5$ = F, $R^7$ = Cl) | | |
| 3.6 | CO$_2$CH$_3$ | A1 ($R^5$ = Cl, $R^7$ = Cl) | | |
| 3.7 | CO$_2$CH$_3$ | A1 ($R^5$ = Br, $R^7$ = Cl) | | |
| 3.8 | CO$_2$CH$_3$ | A1 ($R^5$ = I, $R^7$ = Cl) | | |
| 4.1 | CO$_2$CH$_3$ | A1 ($R^5$ = CF$_3$, $R^7$ = Br) | | |
| 4.2 | CO$_2$CH$_3$ | A1 ($R^5$ = CHF$_2$, $R^7$ = Br) | | |
| 4.3 | CO$_2$CH$_3$ | A1 ($R^5$ = CH$_3$, $R^7$ = Br) | | |
| 4.4 | CO$_2$CH$_3$ | A1 ($R^5$ = C$_2$H$_5$, $R^7$ = Br) | | |
| 4.5 | CO$_2$CH$_3$ | A1 ($R^5$ = F, $R^7$ = Br) | | |
| 4.6 | CO$_2$CH$_3$ | A1 ($R^5$ = Cl, $R^7$ = Br) | | |
| 4.7 | CO$_2$CH$_3$ | A1 ($R^5$ = Br, $R^7$ = Br) | | |
| 4.8 | CO$_2$CH$_3$ | A1 ($R^5$ = I, $R^7$ = Br) | | |
| 5.1 | CO$_2$CH$_3$ | A1 ($R^5$ = CF$_3$, $R^7$ = I) | | |
| 5.2 | CO$_2$CH$_3$ | A1 ($R^5$ = CHF$_2$, $R^7$ = I) | | |
| 5.3 | CO$_2$CH$_3$ | A1 ($R^5$ = CH$_3$, $R^7$ = I) | | |
| 5.4 | CO$_2$CH$_3$ | A1 ($R^5$ = C$_2$H$_5$, $R^7$ = I) | | |
| 5.5 | CO$_2$CH$_3$ | A1 ($R^5$ = F, $R^7$ = I) | | |
| 5.6 | CO$_2$CH$_3$ | A1 ($R^5$ = Cl, $R^7$ = I) | | |
| 5.7 | CO$_2$CH$_3$ | A1 ($R^5$ = Br, $R^7$ = I) | | |
| 5.8 | CO$_2$CH$_3$ | A1 ($R^5$ = I, $R^7$ = I) | | |
| 6.1 | CO$_2$CH$_3$ | A1 ($R^5$ = CF$_3$, $R^7$ = CH$_3$) | | |
| 6.2 | CO$_2$CH$_3$ | A1 ($R^5$ = CHF$_2$, $R^7$ = CH$_3$) | | |
| 6.3 | CO$_2$CH$_3$ | A1 ($R^5$ = CH$_3$, $R^7$ = CH$_3$) | | |

TABLE 1-continued

| Compound No. | $R^9$ | Ar | m.p. (° C.) | $^1$H—NMR(270 MHz) (CDCl$_3$, δ value, J:Hz) |
|---|---|---|---|---|
| 6.4 | CO$_2$CH$_3$ | A1 (R$^5$ = C$_2$H$_5$, R$^7$ = CH$_3$) | | |
| 6.5 | CO$_2$CH$_3$ | A1 (R$^5$ = F, R$^7$ = CH$_3$) | | |
| 6.6 | CO$_2$CH$_3$ | A1 (R$^5$ = Cl, R$^7$ = CH$_3$) | | |
| 6.7 | CO$_2$CH$_3$ | A1 (R$^5$ = Br, R$^7$ = CH$_3$) | | |
| 6.8 | CO$_2$CH$_3$ | A1 (R$^5$ = I, R$^7$ = CH$_3$) | | |
| 7.1 | CO$_2$CH$_3$ | A1 (R$^5$ = CF$_3$, R$^7$ = OCH$_3$) | | |
| 7.2 | CO$_2$CH$_3$ | A1 (R$^5$ = CHF$_2$, R$^7$ = OCH$_3$) | | |
| 7.3 | CO$_2$CH$_3$ | A1 (R$^5$ = CH$_3$, R$^7$ = OCH$_3$) | | |
| 7.4 | CO$_2$CH$_3$ | A1 (R$^5$ = C$_2$H$_5$, R = OCH$_3$) | | |
| 7.5 | CO$_2$CH$_3$ | A1 (R$^5$ = F, R$^7$ = OCH$_3$) | | |
| 7.6 | CO$_2$CH$_3$ | A1 (R$^5$ = Cl, R$^7$ = OCH$_3$) | | |
| 7.7 | CO$_2$CH$_3$ | A1 (R$^5$ = Br, R$^7$ = OCH$_3$) | | |
| 7.8 | CO$_2$CH$_3$ | A1 (R$^5$ = I, R$^7$ = OCH$_3$) | | |
| 8.1 | CO$_2$H | A1 (R$^5$ = CF$_3$, R$^7$ = H | 221.6~ 222 | 4.03(3H, s), 7.53(1H, d, J=5.6), 8.09 (1H, s), 8.13(1H, d, J=5.6) |
| 8.2 | CO$_2$H | A1 (R$^5$ = CHF$_2$, R$^7$ = H) | | |
| 8.3 | CO$_2$H | A1 (R$^5$ = CH$_3$, R$^7$ = H) | | |
| 8.4 | CO$_2$H | A1 (R$^5$ = C$_2$H$_5$, R$^7$ = H) | | |
| 8.5 | CO$_2$H | A1 (R$^5$ = F, R$^7$ = H) | | |
| 8.6 | CO$_2$H | A1 (R$^5$ = Cl, R$^7$ = H) | | |
| 8.7 | CO$_2$H | A1 (R$^5$ = Br, R$^7$ = H) | | |
| 8.8 | CO$_2$H | A1 (R$^5$ = I, R$^7$ = H) | | |
| 9.1 | CO$_2$H | A1 (R$^5$ = CF$_3$, R$^7$ = F) | | |
| 9.2 | CO$_2$H | A1 (R$^5$ = CHF$_2$, R$^7$ = F) | | |
| 9.3 | CO$_2$H | A1 (R$^5$ = CH$_3$, R$^7$ = F) | | |
| 9.4 | CO$_2$H | A1 (R$^5$ = C$_2$H$_5$, R$^7$ = F) | | |
| 9.5 | CO$_2$H | A1 (R$^5$ = F, R$^7$ = F) | | |
| 9.6 | CO$_2$H | A1 (R$^5$ = Cl, R$^7$ = F) | | |
| 9.7 | CO$_2$H | A1 (R$^5$ = Br, R$^7$ = F) | | |
| 9.8 | CO$_2$H | A1 (R$^5$ = I, R$^7$ = F) | | |
| 10.1 | CO$_2$H | A1 (R$^5$ = CF$_3$, R$^7$ = Cl) | | |
| 10.2 | CO$_2$H | A1 (R$^5$ = CHF$_2$, R$^7$ = Cl) | | |
| 10.3 | CO$_2$H | A1 (R$^5$ = CH$_3$, R$^7$ = Cl) | | |
| 10.4 | CO$_2$H | A1 (R$^5$ = C$_2$H$_5$, R$^7$ = Cl) | | |
| 10.5 | CO$_2$H | A1 (R$^5$ = F, R$^7$ = Cl) | | |
| 10.6 | CO$_2$H | A1 (R$^5$ = Cl, R$^7$ = Cl) | | |
| 10.7 | CO$_2$H | A1 (R$^5$ = Br, R$^7$ = Cl) | | |
| 10.8 | CO$_2$H | A1 (R$^5$ = I, R$^7$ = Cl) | | |
| 11.1 | CO$_2$H | A1 (R$^5$ = CF$_3$, R$^7$ = Br) | | |

TABLE 1-continued

| Compound No. | $R^9$ | Ar | m.p. (°C.) | $^1$H—NMR(270 MHz) (CDCl$_3$, δ value, J:Hz) |
|---|---|---|---|---|
| 11.2 | CO$_2$H | A1 ($R^5$ = CHF$_2$, $R^7$ = Br) | | |
| 11.3 | CO$_2$H | A1 ($R^5$ = CH$_3$, $R^7$ = Br) | | |
| 11.4 | CO$_2$H | A1 ($R^5$ = C$_2$H$_5$, $R^7$ = Br) | | |
| 11.5 | CO$_2$H | A1 ($R^5$ = F, $R^7$ = Br) | | |
| 11.6 | CO$_2$H | A1 ($R^5$ = Cl, $R^7$ = Br) | | |
| 11.7 | CO$_2$H | A1 ($R^5$ = Br, $R^7$ = Br) | | |
| 11.8 | CO$_2$H | A1 ($R^5$ = I, $R^7$ = Br) | | |
| 12.1 | CO$_2$H | A1 ($R^5$ = CF$_3$, $R^7$ = I) | | |
| 12.2 | CO$_2$H | A4 ($R^5$ = CHF$_2$, $R^7$ = I) | | |
| 12.3 | CO$_2$H | A1 ($R^5$ = CH$_3$, $R^7$ = I) | | |
| 12.4 | CO$_2$H | A1 ($R^5$ = C$_2$H$_5$, $R^7$ = I) | | |
| 12.5 | CO$_2$H | A1 ($R^5$ = F, $R^7$ = I) | | |
| 12.6 | CO$_2$H | A1 ($R^5$ = Cl, $R^7$ = I) | | |
| 12.7 | CO$_2$H | A1 ($R^5$ = Br, $R^7$ = I) | | |
| 12.8 | CO$_2$H | A1 ($R^5$ = I, $R^7$ = I) | | |
| 13.1 | CO$_2$H | A1 ($R^5$ = CF$_3$, $R^7$ = CH$_3$) | | |
| 13.2 | CO$_2$H | A1 ($R^5$ = CHF$_2$, $R^7$ = CH$_3$) | | |
| 13.3 | CO$_2$H | A1 ($R^5$ = CH$_3$, $R^7$ = CH$_3$) | | |
| 13.4 | CO$_2$H | A1 ($R^5$ = C$_2$H$_5$, $R^7$ = CH$_3$) | | |
| 13.5 | CO$_2$H | A1 ($R^5$ = F, $R^7$ = CH$_3$) | | |
| 13.6 | CO$_2$H | A1 ($R^5$ = Cl, $R^7$ = CH$_3$) | | |
| 13.7 | CO$_2$H | A1 ($R^5$ = Br, $R^7$ = CH$_3$) | | |
| 13.8 | CO$_2$H | A1 ($R^5$ = I, $R^7$ = CH$_3$) | | |
| 14.1 | CO$_2$H | A1 ($R^5$ = CF$_3$, $R^7$ = OCH$_3$) | | |
| 14.2 | CO$_2$H | A1 ($R^5$ = CHF$_2$, $R^7$ = OCH$_3$) | | |
| 14.3 | CO$_2$H | A1 ($R^5$ = CH$_3$, $R^7$ = OCH$_3$) | | |
| 14.4 | CO$_2$H | A1 ($R^5$ = C$_2$H$_5$, $R^7$ = OCH$_3$) | | |
| 14.5 | CO$_2$H | A1 ($R^5$ = F, $R^7$ = OCH$_3$) | | |
| 14.6 | CO$_2$H | A1 ($R^5$ = Cl, $R^7$ = OCH$_3$) | | |
| 14.7 | CO$_2$H | A1 ($R^5$ = Br, $R^7$ = OCH$_3$) | | |
| 14.8 | CO$_2$H | A1 ($R^5$ = I, $R^7$ = OCH$_3$) | | |
| 15.1 | H | A1 ($R^5$ = CF$_3$, $R^7$ = H) | 158.3~ 158.9 | 3.98(3H, s), 7.03(1H, dd, J=5.2, 1.3) , 7.46(1H, dd, J=5.2, 3.3), 7.65(1H, dd, J=3.3, 1.3), 8.00(1H, s), 8.01(1H, brs) |
| 15.2 | H | A1 ($R^5$ = CHF$_2$, $R^7$ = H) | | |
| 15.3 | H | A1 ($R^5$ = CH$_3$, $R^7$ = H) | | |
| 15.4 | H | A1 ($R^5$ = C$_2$H$_5$, $R^7$ = H) | | |
| 15.5 | H | A1 ($R^5$ = F, $R^7$ = H) | | |
| 15.6 | H | A1 ($R^5$ = Cl, $R^7$ = H) | | |

TABLE 1-continued

| Compound No. | $R^9$ | Ar | m.p. (° C.) | $^1$H—NMR(270 MHz) (CDCl$_3$, δ value, J:Hz) |
|---|---|---|---|---|
| 15.7 | H | A1 ($R^5$ = Br, $R^7$ = H) | | |
| 15.8 | H | A1 ($R^5$ = I, $R^7$ = H) | | |
| 16.1 | H | A1 ($R^5$ = CF$_3$, $R^7$ = F) | | |
| 16.2 | H | A1 ($R^5$ = CHF$_2$, $R^7$ = F) | | |
| 16.3 | H | A1 ($R^5$ = CH$_3$, $R^7$ = F) | | |
| 16.4 | H | A1 ($R^5$ = C$_2$H$_5$, $R^7$ = F) | | |
| 16.5 | H | A1 ($R^5$ = F, $R^7$ = F) | | |
| 16.6 | H | A1 ($R^5$ = Cl, $R^7$ = F) | | |
| 16.7 | H | A1 ($R^5$ = Br, $R^7$ = F) | | |
| 16.8 | H | A1 ($R^5$ = I, $R^7$ = F) | | |
| 17.1 | H | A1 ($R^5$ = CF$_3$, $R^7$ = Cl) | | |
| 17.2 | H | A1 ($R^5$ = CHF$_2$, $R^7$ = Cl) | | |
| 17.3 | H | A1 ($R^5$ = CH$_3$, $R^7$ = Cl) | | |
| 17.4 | H | A1 ($R^5$ = C$_{H5}$, $R^7$ = Cl) | | |
| 17.5 | H | A1 ($R^5$ = F, $R^7$ = Cl) | | |
| 17.6 | H | A1 ($R^5$ = Cl, $R^7$ = Cl) | | |
| 17.7 | H | A1 ($R^5$ = Br, $R^7$ = Cl) | | |
| 17.8 | H | A1 ($R^5$ = I, $R^7$ = Cl) | | |
| 18.1 | H | A1 ($R^5$ = CF$_3$, $R^7$ = Br) | | |
| 18.2 | H | A1 ($R^5$ = CHF$_2$, $R^7$ = Br) | | |
| 18.3 | H | A1 ($R^5$ = CH$_3$, $R^7$ = Br) | | |
| 18.4 | H | A1 ($R^5$ = C$_2$H$_5$, $R^7$ = Br) | | |
| 18.5 | H | A1 ($R^5$ = F, $R^7$ = Br) | | |
| 18.6 | H | A1 ($R^5$ = Cl, $R^7$ = Br) | | |
| 18.7 | H | A1 ($R^5$ = Br, $R^7$ = Br) | | |
| 18.8 | H | A1 ($R^5$ = I, $R^7$ = Br) | | |
| 19.1 | H | A1 ($R^5$ = CF$_3$, $R^7$ = I) | | |
| 19.2 | H | A1 ($R^5$ = CHF$_2$, $R^7$ = I) | | |
| 19.3 | H | A1 ($R^5$ = CH$_3$, $R^7$ = I) | | |
| 19.4 | H | A1 ($R^5$ = C$_2$H$_5$, $R^7$ = I) | | |
| 19.5 | H | A1 ($R^5$ = F, $R^7$ = I) | | |
| 19.6 | H | A1 ($R^5$ = Cl, $R^7$ = I) | | |
| 19.7 | H | A1 ($R^5$ = Br, $R^7$ = I) | | |
| 19.8 | H | A1 ($R^5$ = I, $R^7$ = I) | | |
| 20.1 | H | A1 ($R^5$ = CF$_3$, $R^7$ = CH$_3$) | | |
| 20.2 | H | A1 ($R^5$ = CHF$_2$, $R^7$ = CH$_3$) | | |
| 20.3 | H | A1 ($R^5$ = CH$_3$, $R^7$ = CH$_3$) | | |
| 20.4 | H | A1 ($R^5$ = C$_2$H$_5$, $R^7$ = CH$_3$) | | |

TABLE 1-continued

| Compound No. | $R^9$ | Ar | m.p. (° C.) | $^1$H—NMR(270 MHz) (CDCl$_3$, δ value, J:Hz) |
|---|---|---|---|---|
| 20.5 | H | A1 ($R^5$ = F, $R^7$ = CH$_3$) | | |
| 20.6 | H | A1 ($R^5$ = Cl, $R^7$ = CH$_3$) | | |
| 20.7 | H | A1 ($R^5$ = Br, $R^7$ = CH$_3$) | | |
| 20.8 | H | A1 ($R^5$ = I, $R^7$ = CH$_3$) | | |
| 21.1 | H | A1 ($R^5$ = CF$_3$, $R^7$ = OCH$_3$) | | |
| 21.2 | H | A1 ($R^5$ = CHF$_2$, $R^7$ = OCH$_3$) | | |
| 21.3 | H | A1 ($R^5$ = CH$_3$, $R^7$ = OCH$_3$) | | |
| 21.4 | H | A1 ($R^5$ = C$_2$H$_5$, $R^7$ = OCH$_3$) | | |
| 21.5 | H | A1 ($R^5$ = F, $R^7$ = OCH$_3$) | | |
| 21.6 | H | A1 ($R^5$ = Cl, $R^7$ = OCH$_3$) | | |
| 21.7 | H | A1 ($R^5$ = Br, $R^7$ = OCH$_3$) | | |
| 21.8 | H | A1 ($R^5$ = I, $R^7$ = OCH$_3$) | | |
| 22.1 | CO$_2$CH$_3$ | A2 ($R^5$ = CF$_3$, $R^6$ = H) | | |
| 22.2 | CO$_2$CH$_3$ | A2 ($R^5$ = CHF$_2$, $R^6$ = H) | | |
| 22.3 | CO$_2$CH$_3$ | A2 ($R^5$ = CH$_3$, $R^6$ = H) | | |
| 22.4 | CO$_2$CH$_3$ | A2 ($R^5$ = C$_2$H$_5$, $R^6$ = H) | | |
| 22.5 | CO$_2$CH$_3$ | A2 ($R^5$ = F, $R^6$ = H) | | |
| 22.6 | CO$_2$CH$_3$ | A2 ($R^5$ = Cl, $R^6$ = H) | | |
| 22.7 | CO$_2$CH$_3$ | A2 ($R^5$ = Br, $R^6$ = H) | | |
| 22.8 | CO$_2$CH$_3$ | A2 ($R^5$ = I, $R^6$ = H) | | |
| 23.1 | CO$_2$CH$_3$ | A2 ($R^5$ = CF$_3$, $R^6$ = CH$_3$) | | |
| 23.2 | CO$_2$CH$_3$ | A2 ($R^5$ = CHF$_2$, $R^6$ = CH$_3$) | | |
| 23.3 | CO$_2$CH$_3$ | A2 ($R^5$ = CH$_3$, $R^6$ = CH$_3$) | | |
| 23.4 | CO$_2$CH$_3$ | A2 ($R^5$ = C$_2$H$_5$, $R^6$ = CH$_3$) | 107.1~ 109.4 | 1.35(3H, t, J=7.6), 2.73(3H, s), 3.18 (2H, q, J=7.6), 3.93(3H, s), 7.52 (1H, d, J=5.0), 8.19(1H, d, J=5.0), 10.7(1 H, brs) |
| 23.5 | CO$_2$CH$_3$ | A2 ($R^5$ = F, $R^6$ = CH$_3$) | | |
| 23.6 | CO$_2$CH$_3$ | A2 ($R^5$ = Cl, $R^6$ = CH$_3$) | | |
| 23.7 | CO$_2$CH$_3$ | A2 ($R^5$ = Br, $R^6$ = CH$_3$) | | |
| 23.8 | CO$_2$CH$_3$ | A2 ($R^5$ = I, $R^6$ = CH$_3$) | | |
| 24.1 | CO$_2$CH$_3$ | A2 ($R^5$ = CF$_3$, $R^6$ = CF$_3$) | | |
| 24.2 | CO$_2$CH$_3$ | A2 ($R^5$ = CHF$_2$, $R^6$ = CF$_3$) | | |
| 24.3 | CO$_2$CH$_3$ | A2 ($R^5$ = CH$_3$, $R^6$ = CF$_3$) | | |
| 24.4 | CO$_2$CH$_3$ | A2 ($R^5$ = C$_2$H$_5$, R = CF$_3$) | | |
| 24.5 | CO$_2$CH$_3$ | A2 ($R^5$ = F, $R^6$ = CF$_3$) | | |
| 24.6 | CO$_2$CH$_3$ | A2 ($R^5$ = Cl, $R^6$ = CF$_3$) | | |
| 24.7 | CO$_2$CH$_3$ | A2 ($R^5$ = Br, $R^6$ = CH$_3$) | | |
| 24.8 | CO$_2$CH$_3$ | A2 ($R^5$ = I, $R^6$ = CF$_3$) | | |
| 25.1 | CO$_2$CH$_3$ | A2 ($R^5$ = CF$_3$, $R^6$ = F) | | |

TABLE 1-continued

| Compound No. | $R^9$ | Ar | m.p. (° C.) | $^1$H—NMR(270 MHz) (CDCl$_3$, δ value, J:Hz) |
|---|---|---|---|---|
| 25.2 | CO$_2$CH$_3$ | A2 ($R^5$ = CHF$_2$, $R^6$ = F) | | |
| 25.3 | CO$_2$CH$_3$ | A2 ($R^5$ = CH$_3$, $R^6$ = F) | | |
| 25.4 | CO$_2$CH$_3$ | A2 ($R^5$ = C$_2$H$_5$, $R^6$ = F) | | |
| 25.5 | CO$_2$CH$_3$ | A2 ($R^5$ = F, $R^6$ = F) | | |
| 25.6 | CO$_2$CH$_3$ | A2 ($R^5$ = Cl, $R^6$ = F) | | |
| 25.7 | CO$_2$CH$_3$ | A2 ($R^5$ = Br, $R^6$ = F) | | |
| 25.8 | CO$_2$CH$_3$ | A2 ($R^5$ = I, $R^6$ = F) | | |
| 26.1 | CO$_2$CH$_3$ | A2 ($R^5$ = CF$_3$, $R^6$ = Cl) | | |
| 26.2 | CO$_2$CH$_3$ | A2 ($R^5$ = CHF$_2$, $R^6$ = Cl) | | |
| 26.3 | CO$_2$CH$_3$ | A2 ($R^5$ = CH$_3$, $R^6$ = Cl) | | |
| 26.4 | CO$_2$CH$_3$ | A2 ($R^5$ = C$_2$H$_5$, $R^6$ = Cl) | | |
| 26.5 | CO$_2$CH$_3$ | A2 ($R^5$ = F, $R^6$ = Cl) | | |
| 26.6 | CO$_2$CH$_3$ | A2 ($R^5$ = Cl, $R^6$ = Cl) | | |
| 26.7 | CO$_2$CH$_3$ | A2 ($R^5$ = Br, $R^6$ = Cl) | | |
| 26.8 | CO$_2$CH$_3$ | A2 ($R^5$ = I, $R^6$ = Cl) | | |
| 27.1 | CO$_2$CH$_3$ | A2 ($R^5$ = CF$_3$, $R^6$ = Br) | | |
| 27.2 | CO$_2$CH$_3$ | A2 ($R^5$ = CHF$_2$, $R^6$ = Br) | | |
| 27.3 | CO$_2$CH$_3$ | A2 ($R^5$ = CH$_3$, $R^6$ = Br) | | |
| 27.4 | CO$_2$CH$_3$ | A2 ($R^5$ = C$_2$H$_5$, $R^6$ = Br) | | |
| 27.5 | CO$_2$CH$_3$ | A2 ($R^5$ = F, $R^6$ = Br) | | |
| 27.6 | CO$_2$CH$_3$ | A2 ($R^5$ = Cl, $R^6$ = Br) | | |
| 27.7 | CO$_2$CH$_3$ | A2 ($R^5$ = Br, $R^6$ = Br) | | |
| 27.8 | CO$_2$CH$_3$ | A1 ($R^5$ = I, $R^6$ = Br) | | |
| 28.1 | CO$_2$CH$_3$ | A2 ($R^5$ = CF$_3$, $R^6$ = I) | | |
| 28.2 | CO$_2$CH$_3$ | A2 ($R^5$ = CHF$_2$, $R^6$ = I) | | |
| 28.3 | CO$_2$CH$_3$ | A2 ($R^5$ = CH$_3$, $R^6$ = I) | | |
| 28.4 | CO$_2$CH$_3$ | A2 ($R^5$ = C$_2$H$_5$, $R^6$ = I) | | |
| 28.5 | CO$_2$CH$_3$ | A2 ($R^5$ = F, $R^6$ = I) | | |
| 28.6 | CO$_2$CH$_3$ | A2 ($R^5$ = Cl, $R^6$ = I) | | |
| 28.7 | CO$_2$CH$_3$ | A2 ($R^5$ = Br, $R^6$ = I) | | |
| 28.8 | CO$_2$CH$_3$ | A2 ($R^5$ = I, $R^6$ = I) | | |
| 29.1 | CO$_2$CH$_3$ | A2 ($R^5$ = CF$_3$, $R^6$ = OCH$_3$) | | |
| 29.2 | CO$_2$CH$_3$ | A2 ($R^5$ = CHF$_2$, $R^6$ = OCH$_3$) | | |
| 29.3 | CO$_2$CH$_3$ | A2 ($R^5$ = CH$_3$, $R^6$ = OCH$_3$) | | |
| 29.4 | CO$_2$CH$_3$ | A2 ($R^5$ = C$_2$H$_5$, $R^6$ = OCH$_3$) | | |
| 29.5 | CO$_2$CH$_3$ | A2 ($R^5$ = F, $R^6$ = OCH$_3$) | | |
| 29.6 | CO$_2$CH$_3$ | A2 ($R^5$ = Cl, $R^6$ = OCH$_3$) | | |
| 29.7 | CO$_2$CH$_3$ | A2 ($R^5$ = Br, $R^6$ = OCH$_3$) | | |

TABLE 1-continued

| Compound No. | $R^9$ | Ar | m.p. (° C.) | $^1$H—NMR(270 MHz) (CDCl$_3$, δ value, J:Hz) |
|---|---|---|---|---|
| 29.8 | CO$_2$CH$_3$ | A2 (R$^5$ = I, R = OCH$_3$) | | |
| 30.1 | CO$_2$CH$_3$ | A2 (R$^5$ = CF$_3$, R$^6$ = NH$_2$) | | |
| 30.2 | CO$_2$CH$_3$ | A2 (R$^5$ = CHF$_2$, R$^6$ = NH$_2$) | | |
| 30.3 | CO$_2$CH$_3$ | A2 (R$^5$ = CH$_3$, R$^5$ = NH$_2$) | | |
| 30.4 | CO$_2$CH$_3$ | A2 (R$^5$ = C$_2$H$_5$, R$^6$ = NH$_2$) | | |
| 30.5 | CO$_2$CH$_3$ | A2 (R$^5$ = F, R$^6$ = NH$_2$) | | |
| 30.6 | CO$_2$CH$_3$ | A2 (R$^5$ = Cl, R$^6$ = NH$_2$) | | |
| 30.7 | CO$_2$CH$_3$ | A2 (R$^5$ = Br, R$^6$ = NH$_2$) | | |
| 30.8 | CO$_2$CH$_3$ | A2 (R$^5$ = I, R$^6$ = NH$_2$) | | |
| 31.1 | CO$_2$H | A2 (R$^5$ = CF$_3$, R$^6$ = H) | | |
| 31.2 | CO$_2$H | A2 (R$^5$ = CHF$_2$, R$^6$ = H) | | |
| 31.3 | CO$_2$H | A2 (R$^5$ = CH$_3$, R$^6$ = H) | | |
| 31.4 | CO$_2$H | A2 (R$^5$ = C$_2$H$_5$, R$^6$ = H) | | |
| 31.5 | CO$_2$H | A2 (R$^5$ = F, R$^6$ = H) | | |
| 31.6 | CO$_2$H | A2 (R$^5$ = Cl, R$^6$ = H) | | |
| 31.7 | CO$_2$H | A2 (R$^5$ = Br, R$^6$ = H) | | |
| 31.8 | CO$_2$H | A2 (R$^5$ = I, R$^6$ = H) | | |
| 32.1 | CO$_2$H | A2 (R$^5$ = CF$_3$, R$^6$ = CH$_3$) | | |
| 32.2 | CO$_2$H | A2 (R$^5$ = CHF$_2$, R$^6$ = CH$_3$) | | |
| 32.3 | CO$_2$H | A2 (R$^6$ = CH$_3$, R$^6$ = CH$_3$) | | |
| 32.4 | CO$_2$H | A2 (R$^5$ = C$_2$H$_5$, R$^6$ = CH$_3$) | | |
| 32.5 | CO$_2$H | A2 (R$^5$ = F, R$^6$ = CH$_3$) | | |
| 32.6 | CO$_2$H | A2 (R$^5$ = Cl, R$^6$ = CH$_3$) | | |
| 32.7 | CO$_2$H | A2 (R$^5$ = Br, R$^6$ = CH$_3$) | | |
| 32.8 | CO$_2$H | A2 (R$^5$ = I, R$^6$ = CH$_3$) | | |
| 33.1 | CO$_2$H | A2 (R$^5$ = CF$_3$, R$^6$ = CF$_3$) | | |
| 33.2 | CO$_2$H | A2 (R$^5$ = CHF$_2$, R$^6$ = CF$_3$) | | |
| 33.3 | CO$_2$H | A2 (R$^5$ = CH$_3$, R$^6$ = CF$_3$) | | |
| 33.4 | CO$_2$H | A2 (R$^5$ = C$_2$H$_5$, R$^6$ = CF$_3$) | | |
| 33.5 | CO$_2$H | A2 (R$^5$ = F, R$^6$ = CF$_3$) | | |
| 33.6 | CO$_2$H | A2 (R$^5$ = Cl, R$^6$ = CF$_3$) | | |
| 33.7 | CO$_2$H | A2 (R$^5$ = Br, R$^6$ = CH$_3$) | | |
| 33.8 | CO$_2$H | A2 (R$^5$ = I, R$^6$ = CF$_3$) | | |
| 34.1 | CO$_2$H | A2 (R$^5$ = CF$_3$, R$^6$ = F) | | |
| 34.2 | CO$_2$H | A2 (R$^5$ = CHF$_2$, R$^6$ = F) | | |
| 34.3 | CO$_2$H | A2 (R$^5$ = CH$_3$, R$^6$ = F) | | |
| 34.4 | CO$_2$H | A2 (R$^5$ = C$_2$H$_5$, R$^6$ = F) | | |
| 34.5 | CO$_2$H | A2 (R$^5$ = F, R$^6$ = F) | | |

TABLE 1-continued

| Compound No. | $R^9$ | Ar | m.p. (° C.) | $^1$H—NMR(270 MHz) (CDCl$_3$, δ value, J:Hz) |
|---|---|---|---|---|
| 34.6 | CO$_2$H | A2 ($R^5$ = Cl, $R^6$ = F) | | |
| 34.7 | CO$_2$H | A2 ($R^5$ = Br, $R^6$ = F) | | |
| 34.8 | CO$_2$H | A2 ($R^5$ = I, $R^6$ = F) | | |
| 35.1 | CO$_2$H | A2 ($R^5$ = CF$_3$, $R^6$ = Cl) | | |
| 35.2 | CO$_2$H | A2 ($R^5$ = CHF$_2$, $R^6$ = Cl) | | |
| 35.3 | CO$_2$H | A2 ($R^5$ = CH$_3$, $R^6$ = Cl) | | |
| 35.4 | CO$_2$H | A2 ($R^5$ = C$_2$H$_5$, $R^6$ = Cl) | | |
| 35.5 | CO$_2$H | A2 ($R^5$ = F, $R^6$ = Cl) | | |
| 35.6 | CO$_2$H | A2 ($R^5$ = Cl, $R^6$ = Cl) | | |
| 35.7 | CO$_2$H | A2 ($R^5$ = Br, $R^6$ = Cl) | | |
| 35.8 | CO$_2$H | A2 ($R^5$ = I, $R^6$ = Cl) | | |
| 36.1 | CO$_2$H | A2 ($R^5$ = CF$_3$, $R^6$ = Br) | | |
| 36.2 | CO$_2$H | A2 ($R^5$ = CHF$_2$, $R^6$ = Br) | | |
| 36.3 | CO$_2$H | A2 ($R^5$ = CH$_3$, $R^6$ = Br) | | |
| 36.4 | CO$_2$H | A2 ($R^5$ = C$_2$H$_5$, $R^6$ = Br) | | |
| 36.5 | CO$_2$H | A2 ($R^5$ = F, $R^6$ = Br) | | |
| 36.6 | CO$_2$H | A2 ($R^5$ = Cl, $R^6$ = Br) | | |
| 36.7 | CO$_2$H | A2 ($R^5$ = Br, $R^6$ = Br) | | |
| 36.8 | CO$_2$H | A1 ($R^5$ = I, $R^6$ = Br) | | |
| 37.1 | CO$_2$H | A2 ($R^5$ = CF$_3$, $R^6$ = I) | | |
| 37.2 | CO$_2$H | A2 ($R^5$ = CHF$_2$, $R^6$ = I) | | |
| 37.3 | CO$_2$H | A2 ($R^5$ = CH$_3$, $R^6$ = I) | | |
| 37.4 | CO$_2$H | A2 ($R^5$ = C$_2$H$_5$, $R^6$ = I) | | |
| 37.5 | CO$_2$H | A2 ($R^5$ = F, $R^6$ = I) | | |
| 37.6 | CO$_2$H | A2 ($R^5$ = Cl, $R^6$ = I) | | |
| 37.7 | CO$_2$H | A2 ($R^5$ = Br, $R^6$ = I) | | |
| 37.8 | CO$_2$H | A2 ($R^5$ = I, $R^6$ = I) | | |
| 38.1 | CO$_2$H | A2 ($R^5$ = CF$_3$, $R^6$ = OCH$_3$) | | |
| 38.2 | CO$_2$H | A2 ($R^5$ = CHF$_2$, $R^6$ = OCH$_3$) | | |
| 38.3 | CO$_2$H | A2 ($R^5$ = CH$_3$, $R^6$ = OCH$_3$) | | |
| 38.4 | CO$_2$H | A2 ($R^5$ = C$_2$H$_5$, $R^6$ = OCH$_3$) | | |
| 38.5 | CO$_2$H | A2 ($R^5$ = F, $R^6$ = OCH$_3$) | | |
| 38.6 | CO$_2$H | A2 ($R^5$ = Cl, $R^6$ = OCH$_3$) | | |
| 38.7 | CO$_2$H | A2 ($R^5$ = Br, $R^6$ = OCH$_3$) | | |
| 38.8 | CO$_2$H | A2 ($R^5$ = I, $R^6$ = OCH$_3$) | | |
| 39.1 | CO$_2$H | A2 ($R^5$ = CF$_3$, $R^6$ = NH$_2$) | | |
| 39.2 | CO$_2$H | A2 ($R^5$ = CHF$_2$, $R^6$ = NH$_2$) | | |
| 39.3 | CO$_2$H | A2 ($R^5$ = CH$_3$, $R^6$ = NH$_2$) | | |

TABLE 1-continued

| Compound No. | $R^9$ | Ar | m.p. (° C.) | $^1$H—NMR(270 MHz) (CDCl$_3$, δ value, J:Hz) |
|---|---|---|---|---|
| 39.4 | CO$_2$H | A2 ($R^5$ = C$_2$H$_5$, $R^6$ = NH$_2$) | | |
| 39.5 | CO$_2$H | A2 ($R^5$ = F, $R^6$ = NH$_2$) | | |
| 39.6 | CO$_2$H | A2 ($R^5$ = Cl, $R^6$ = NH$_2$) | | |
| 39.7 | CO$_2$H | A2 ($R^5$ = Br, $R^6$ = NH$_2$) | | |
| 39.8 | CO$_2$H | A2 ($R^5$ = I, $R^6$ = NH$_2$) | | |
| 40.1 | H | A2 ($R^5$ = CF$_3$, $R^6$ = H) | | |
| 40.2 | H | A2 ($R^5$ = CHF$_2$, $R^6$ = H) | | |
| 40.3 | H | A2 ($R^5$ = CH$_3$, $R^6$ = H) | | |
| 40.4 | H | A2 ($R^5$ = C$_2$H$_5$, $R^6$ = H) | | |
| 40.5 | H | A2 ($R^5$ = F, $R^6$ = H) | | |
| 40.6 | H | A2 ($R^5$ = Cl, $R^6$ = H) | | |
| 40.7 | H | A2 ($R^5$ = Br, $R^6$ = H) | | |
| 40.8 | H | A2 ($R^5$ = I, $R^6$ = H) | | |
| 41.1 | H | A2 ($R^5$ = CF$_3$, $R^6$ = CH$_3$) | | |
| 41.2 | H | A2 ($R^5$ = CHF$_2$, $R^6$ = CH$_3$) | | |
| 41.3 | H | A2 ($R^5$ = CH$_3$, $R^6$ = CH$_3$) | | |
| 41.4 | H | A2 ($R^5$ = C$_2$H$_5$, $R^6$ = CH$_3$) | 119.6~ 121.1 | 1.34(3H, t, J=7.3), 2.71(3H, s), 3.10 (2H, q, J=7.3), 7.05(1H, dd,J=5.3, 1. 3), 7.26–7.29(1H, m), 7.62 (1H, dd, J=3.3, 1.3), 7.66(1H, brs) |
| 41.5 | H | A2 ($R^5$ = F, $R^6$ = CH$_3$) | | |
| 41.6 | H | A2 ($R^5$ = Cl, $R^6$ = CH$_3$) | | |
| 41.7 | H | A2 ($R^5$ = Br, $R^6$ = CH$_3$) | | |
| 41.8 | H | A2 ($R^5$ = I, $R^6$ = CH$_3$) | | |
| 42.1 | H | A2 ($R^5$ = CF$_3$, $R^6$ = CF$_3$) | | |
| 42.2 | H | A2 ($R^5$ = CHF$_2$, $R^6$ = CF$_3$) | | |
| 42.3 | H | A2 ($R^5$ = CH$_3$, $R^6$ = CF$_3$) | | |
| 42.4 | H | A2 ($R^5$ = C$_2$H$_5$, $R^6$ = CF$_3$) | | |
| 42.5 | H | A2 ($R^5$ = F, $R^6$ = CF$_3$) | | |
| 42.6 | H | A2 ($R^5$ = Cl, $R^6$ = CF$_3$) | | |
| 42.7 | H | A2 ($R^5$ = Br, $R^6$ = CH$_3$) | | |
| 42.8 | H | A2 ($R^5$ = I, $R^6$ = CF$_3$) | | |
| 43.1 | H | A2 ($R^5$ = CF$_3$, $R^6$ = F) | | |
| 43.2 | H | A2 ($R^5$ = CHF$_2$, $R^6$ = F) | | |
| 43.3 | H | A2 ($R^5$ = CH$_3$, $R^6$ = F) | | |
| 43.4 | H | A2 ($R^5$ = C$_2$H$_5$, $R^6$ = F) | | |
| 43.5 | H | A2 ($R^5$ = F, $R^6$ = F) | | |
| 43.6 | H | A2 ($R^5$ = Cl, $R^6$ = F) | | |
| 43.7 | H | A2 ($R^5$ = Br, $R^6$ = F) | | |
| 43.8 | H | A2 ($R^5$ = I, $R^6$ = F) | | |

TABLE 1-continued

| Compound No. | $R^9$ | Ar | m.p. (° C.) | $^1$H—NMR(270 MHz) (CDCl$_3$, δ value, J:Hz) |
|---|---|---|---|---|
| 44.1 | H | A2 ($R^5$ = CF$_3$, $R^6$ = Cl) | | |
| 44.2 | H | A2 ($R^5$ = CHF$_2$, $R^6$ = Cl) | | |
| 44.3 | H | A2 ($R^5$ = CH$_3$, $R^6$ = Cl) | | |
| 44.4 | H | A2 ($R^5$ = C$_2$H$_5$, $R^6$ = Cl) | | |
| 44.5 | H | A2 ($R^5$ = F, $R^6$ = Cl) | | |
| 44.6 | H | A2 ($R^5$ = Cl, $R^6$ = Cl) | | |
| 44.7 | H | A2 ($R^5$ = Br, $R^6$ = Cl) | | |
| 44.8 | H | A2 ($R^5$ = I, $R^6$ = Cl) | | |
| 45.1 | H | A2 ($R^5$ = CF$_3$, $R^6$ = Br) | | |
| 45.2 | H | A2 ($R^5$ = CHF$_2$, $R^6$ = Br) | | |
| 45.3 | H | A2 ($R^5$ = CH$_3$, $R^6$ = Br) | | |
| 45.4 | H | A2 ($R^5$ = C$_2$H$_5$, $R^6$ = Br) | | |
| 45.5 | H | A2 ($R^5$ = F, $R^6$ = Br) | | |
| 45.6 | H | A2 ($R^5$ = Cl, $R^6$ = Br) | | |
| 45.7 | H | A2 ($R^5$ = Br, $R^6$ = Br) | | |
| 45.8 | H | A1 ($R^5$ = I, $R^6$ = Br) | | |
| 46.1 | CO$_2$H | A2 ($R^5$ = CF$_3$, $R^6$ = I) | | |
| 46.2 | CO$_2$H | A2 ($R^5$ = CHF$_2$, $R^6$ = I) | | |
| 46.3 | CO$_2$H | A2 ($R^5$ = CH$_3$, $R^6$ = I) | | |
| 46.4 | CO$_2$H | A2 ($R^5$ = C$_2$H$_5$, $R^5$ = I) | | |
| 46.5 | CO$_2$H | A2 ($R^5$ = F, $R^6$ = I) | | |
| 46.6 | CO$_2$H | A2 ($R^5$ = Cl $R^6$ = I) | | |
| 46.7 | CO$_2$H | A2 ($R^5$ = Br, $R^6$ = I) | | |
| 46.8 | CO$_2$H | A2 ($R^5$ = I, $R^6$ = I) | | |
| 47.1 | H | A2 ($R^5$ = CF$_3$, $R^6$ = OCH$_3$) | | |
| 47.2 | H | A2 ($R^5$ = CHF$_2$, $R^6$ = OCH$_3$) | | |
| 47.3 | H | A2 ($R^5$ = CH$_3$, $R^6$ = OCH$_3$) | | |
| 47.4 | H | A2 ($R^5$ = C$_2$H$_5$, $R^6$ = OCH$_3$) | | |
| 47.5 | H | A2 ($R^5$ = F, $R^6$ = OCH$_3$) | | |
| 47.6 | H | A2 ($R^5$ = Cl, $R^6$ = OCH$_3$) | | |
| 47.7 | H | A2 ($R^5$ = Br, $R^6$ = OCH$_3$) | | |
| 47.8 | H | A2 ($R^5$ = I, $R^6$ = OCH$_3$) | | |
| 48.1 | H | A2 ($R^5$ = CF$_3$, $R^6$ = NH$_2$) | | |
| 48.2 | H | A2 ($R^5$ = CHF$_2$, $R^6$ = NH$_2$) | | |
| 48.3 | H | A2 ($R^5$ = CH$_3$, $R^6$ = NH$_2$) | | |
| 48.4 | H | A2 ($R^5$ = C$_2$H$_5$, $R^6$ = NH$_2$) | | |
| 48.5 | H | A2 ($R^5$ = F, $R^6$ = NH$_2$) | | |
| 48.6 | H | A2 ($R^5$ = Cl, $R^6$ = NH$_2$) | | |

TABLE 1-continued

| Compound No. | $R^9$ | Ar | m.p. (° C.) | $^1$H—NMR(270 MHz) (CDCl$_3$, δ value, J:Hz) |
|---|---|---|---|---|
| 48.7 | H | A2 ($R^5$ = Br, $R^6$ = NH$_2$) | | |
| 48.8 | H | A2 ($R^5$ = I, $R^6$ = NH$_2$) | | |
| 49.1 | CO$_2$CH$_3$ | A3 ($R^5$ = CF$_3$, $R^8$ = H) | | |
| 49.2 | CO$_2$CH$_3$ | A3 ($R^5$ = CHF$_2$, $R^8$ = H) | | |
| 49.3 | CO$_2$CH$_3$ | A3 ($R^5$ = CH$_3$, $R^8$ = H) | 135.3~136.2 | 2.68(3H, s), 3.92(3H, s), 6.72(1H, d, J=2.3), 7.31(1H, d, J=2.3), 7.50(1H, d, J=5.3), 8.23(1H, d, J=5.3), 10.70 (1H, brs) |
| 49.4 | CO$_2$CH$_3$ | A3 ($R^5$ = C$_2$H$_5$, $R^8$ = H) | | |
| 49.5 | CO$_2$CH$_3$ | A3 ($R^5$ = F, $R^8$ = H) | | |
| 49.6 | CO$_2$CH$_3$ | A3 ($R^5$ = Cl, $R^8$ = H) | | |
| 49.7 | CO$_2$CH$_3$ | A3 ($R^5$ = Br, $R^8$ = H) | | |
| 49.8 | CO$_2$CH$_3$ | A3 ($R^5$ = I, $R^8$ = H) | | |
| 50.1 | CO$_2$CH$_3$ | A3 ($R^5$ = CF$_3$, $R^8$ = CH$_3$) | | |
| 50.2 | CO$_2$CH$_3$ | A3 ($R^5$ = CHF$_2$, $R^8$ = CH$_3$) | | |
| 50.3 | CO$_2$CH$_3$ | A3 ($R^5$ = CH$_3$, $R^8$ = CH$_3$) | | |
| 50.4 | CO$_2$CH$_3$ | A3 ($R^5$ = C$_2$H$_5$, $R^8$ = CH$_3$) | | |
| 50.5 | CO$_2$CH$_3$ | A3 ($R^5$ = F, $R^8$ = CH$_3$) | | |
| 50.6 | CO$_2$CH$_3$ | A3 ($R^5$ = Cl, $R^8$ = CH$_3$) | | |
| 50.7 | CO$_2$CH$_3$ | A3 ($R^5$ = Br, $R^8$ = CH$_3$) | | |
| 50.8 | CO$_2$CH$_3$ | A3 ($R^5$ = I, $R^8$ = CH$_3$) | | |
| 51.1 | CO$_2$CH$_3$ | A3 ($R^5$ = CF$_3$, $R^8$ = CH$_2$CH$_3$) | | |
| 51.2 | CO$_2$CH$_3$ | A3 ($R^5$ = CHF$_2$, $R^8$ = CH$_2$CH$_3$) | | |
| 51.3 | CO$_2$CH$_3$ | A3 ($R^5$ = CH$_3$, $R^8$ = CH$_2$CH$_3$) | | |
| 51.4 | CO$_2$CH$_3$ | A3 ($R^5$ = C$_2$H$_5$, $R^8$ = CH$_2$CH$_3$) | | |
| 51.5 | CO$_2$CH$_3$ | A3 ($R^5$ = F, $R^8$ = CH$_2$CH$_3$) | | |
| 51.6 | CO$_2$CH$_3$ | A3 ($R^5$ = Cl, $R^8$ = CH$_2$CH$_3$) | | |
| 51.7 | CO$_2$CH$_3$ | A3 ($R^5$ = Br, $R^8$ = CH$_2$CH$_3$) | | |
| 51.8 | CO$_2$CH$_3$ | A3 ($R^5$ = I, $R^8$ = CH$_2$CH$_3$) | | |
| 52.1 | CO$_2$CH$_3$ | A3 ($R^5$ = CF$_3$, $R^8$ = F) | | |
| 52.2 | CO$_2$CH$_3$ | A3 ($R^5$ = CHF$_2$, $R^8$ = F) | | |
| 52.3 | CO$_2$CH$_3$ | A3 ($R^5$ = CH$_3$, $R^8$ = F) | | |
| 52.4 | CO$_2$CH$_3$ | A3 ($R^5$ = C$_2$H$_5$, $R^8$ = F) | | |
| 52.5 | CO$_2$CH$_3$ | A3 ($R^5$ = F, $R^8$ = F) | | |
| 52.6 | CO$_2$CH$_3$ | A3 ($R^5$ = Cl, $R^8$ = F) | | |
| 52.7 | CO$_2$CH$_3$ | A3 ($R^5$ = Br, $R^8$ = F) | | |
| 52.8 | CO$_2$CH$_3$ | A3 ($R^5$ = I, $R^8$ = F) | | |
| 53.1 | CO$_2$CH$_3$ | A3 ($R^5$ = CF$_3$, $R^8$ = Cl) | | |
| 53.2 | CO$_2$CH$_3$ | A3 ($R^5$ = CHF$_2$, $R^8$ = Cl) | | |
| 53.3 | CO$_2$CH$_3$ | A3 ($R^5$ = CH$_3$, $R^8$ = Cl) | | |

TABLE 1-continued

| Compound No. | $R^9$ | Ar | m.p. (° C.) | $^1$H—NMR(270 MHz) (CDCl$_3$, δ value, J:Hz) |
|---|---|---|---|---|
| 53.4 | CO$_2$CH$_3$ | A3 ($R^5$ = C$_2$H$_5$, $R^8$ = Cl) | | |
| 53.5 | CO$_2$CH$_3$ | A3 ($R^5$ = F, $R^8$ = Cl) | | |
| 53.6 | CO$_2$CH$_3$ | A3 ($R^5$ = Cl, $R^8$ = Cl) | | |
| 53.7 | CO$_2$CH$_3$ | A3 ($R^5$ = Br, $R^8$ = Cl) | | |
| 53.8 | CO$_2$CH$_3$ | A3 ($R^5$ = I, $R^8$ = Cl) | | |
| 54.1 | CO$_2$CH$_3$ | A3 ($R^5$ = CF$_3$, $R^8$ = Br) | | |
| 54.2 | CO$_2$CH$_3$ | A3 ($R^5$ = CHF$_2$, $R^8$ = Br) | | |
| 54.3 | CO$_2$CH$_3$ | A3 ($R^5$ = CH$_3$, $R^8$ = Br) | | |
| 54.4 | CO$_2$CH$_3$ | A3 ($R^5$ = C$_2$H$_5$, $R^8$ = Br) | | |
| 54.5 | CO$_2$CH$_3$ | A3 ($R^5$ = F, $R^8$ = Br) | | |
| 54.6 | CO$_2$CH$_3$ | A3 ($R^5$ = Cl, $R^8$ = Br) | | |
| 54.7 | CO$_2$CH$_3$ | A3 ($R^5$ = Br, $R^8$ = Br) | | |
| 54.8 | CO$_2$CH$_3$ | A3 ($R^5$ = I, $R^8$ = Br) | | |
| 55.1 | CO$_2$CH$_3$ | A3 ($R^5$ = CF$_3$, $R^8$ = I) | | |
| 55.2 | CO$_2$CH$_3$ | A3 ($R^5$ = CHF$_2$, $R^8$ = I) | | |
| 55.3 | CO$_2$CH$_3$ | A3 ($R^5$ = CH$_3$, $R^8$ = I) | | |
| 55.4 | CO$_2$CH$_3$ | A3 ($R^5$ = C$_2$H$_5$, $R^8$ = I) | | |
| 55.5 | CO$_2$CH$_3$ | A3 ($R^5$ = F, $R^8$ = I) | | |
| 55.6 | CO$_2$CH$_3$ | A3 ($R^5$ = Cl, $R^8$ = I) | | |
| 55.7 | CO$_2$CH$_3$ | A3 ($R^5$ = Br, $R^8$ = I) | | |
| 55.8 | CO$_2$CH$_3$ | A3 ($R^5$ = I, $R^8$ = I) | | |
| 56.1 | CO$_2$H | A3 ($R^5$ = CF$_3$, $R^8$ = H) | | |
| 56.2 | CO$_2$H | A3 ($R^5$ = CHF$_2$, $R^8$ = H) | | |
| 56.3 | CO$_2$H | A3 ($R^5$ = CH$_3$, $R^8$ = H) | | |
| 56.4 | CO$_2$H | A3 ($R^5$ = C$_2$H$_5$, $R^8$ = H) | | |
| 56.5 | CO$_2$H | A3 ($R^5$ = F, $R^8$ = H) | | |
| 56.6 | CO$_2$H | A3 ($R^5$ = Cl, $R^8$ = H) | | |
| 56.7 | CO$_2$H | A3 ($R^5$ = Br, $R^8$ = H) | | |
| 56.8 | CO$_2$H | A3 ($R^5$ = I, $R^8$ = H) | | |
| 57.1 | CO$_2$H | A3 ($R^5$ = CF$_3$, $R^8$ = CH$_3$) | | |
| 57.2 | CO$_2$H | A3 ($R^5$ = CHF$_2$, $R^8$ = CH$_3$) | | |
| 57.3 | CO$_2$H | A3 ($R^5$ = CH$_3$, $R^8$ = CH$_3$) | | |
| 57.4 | CO$_2$H | A3 ($R^5$ = C$_2$H$_5$, $R^8$ = CH$_3$) | | |
| 57.5 | CO$_2$H | A3 ($R^5$ = F, $R^8$ = CH$_3$) | | |
| 57.6 | CO$_2$H | A3 ($R^5$ = Cl, $R^8$ = CH$_3$) | | |
| 57.7 | C()2H | A3 ($R^5$ = Br, $R^8$ = CH$_3$) | | |
| 57.8 | CO2W | A3 ($R^5$ = I, $R^8$ = CH$_3$) | | |
| 58.1 | CO$_2$H | A3 ($R^5$ = CF$_3$, $R^8$ = CH$_2$CH$_3$) | | |

TABLE 1-continued

| Compound No. | $R^9$ | Ar | m.p. (° C.) | $^1$H—NMR(270 MHz) (CDCl$_3$, δ value, J:Hz) |
|---|---|---|---|---|
| 58.2 | CO$_2$H | A3 (R$^5$ = CHF$_2$, R$^8$ = CH$_2$CH$_3$) | | |
| 58.3 | CO$_2$H | A3 (R$^5$ = CH$_3$, R$^8$ = CH$_2$CH$_3$) | | |
| 58.4 | CO$_2$H | A3 (R$^5$ = CH$_5$, R$^8$ = CH$_2$CH$_3$) | | |
| 58.5 | CO$_2$H | A3 (R$^5$ = F, R$^8$ = CH$_2$CH$_3$) | | |
| 58.6 | CO$_2$H | A3 (R$^5$ = Cl, R$^8$ = CH$_2$CH$_3$) | | |
| 58.7 | CO$_2$H | A3 (R$^5$ = Br, R$^8$ = CH$_2$CH$_3$) | | |
| 58.8 | CO$_2$H | A3 (R$^5$ = I, R$^8$ = CH$_2$CH$_3$) | | |
| 59.1 | CO$_2$H | A3 (R$^5$ = CF$_3$, R$^8$ = F) | | |
| 59.2 | CO$_2$H | A3 (R$^5$ = CHF$_2$, R$^8$ = F) | | |
| 59.3 | CO$_2$H | A3 (R$^5$ = CH$_3$, R$^8$ = F) | | |
| 59.4 | CQH | A3 (R$^5$ = C$_2$H$_5$, R$^8$ = F) | | |
| 59.5 | CO$_2$H | A3 (R$^5$ = F, R$^8$ = F) | | |
| 59.6 | CO$_2$H | A3 (R$^5$ = Cl, R$^8$ = F) | | |
| 59.7 | CO$_2$H | A3 (R$^5$ = Br, R$^8$ = F) | | |
| 59.8 | CO$_2$H | A3 (R$^5$ = I, R$^8$ = F) | | |
| 60.1 | CO$_2$H | A3 (R$^5$ = CF$_3$, R$^8$ = Cl) | | |
| 60.2 | CO$_2$H | A3 (R$^5$ = CHF$_2$, R$^8$ = Cl) | | |
| 60.3 | CO$_2$H | A3 (R$^5$ = CH$_3$, R$^8$ = Cl) | | |
| 60.4 | CO$_2$H | A3 (R$^5$ = C$_2$H$_5$, R$^8$ = Cl) | | |
| 60.5 | CO$_2$H | A3 (R$^5$ = F, R$^8$ = Cl) | | |
| 60.6 | CO$_2$H | A3 (R$^5$ = Cl, R$^8$ = Cl) | | |
| 60.7 | CO$_2$H | A3 (R$^5$ = Br, R$^8$ = Cl) | | |
| 60.8 | CO$_2$H | A3 (R$^5$ = I, R$^8$ = Cl) | | |
| 61.1 | CO$_2$H | A3 (R$^5$ = CF$_3$, R$^8$ = Br) | | |
| 61.2 | CO$_2$H | A3 (R$^5$ = CHF$_2$, R$^8$ = Br) | | |
| 61.3 | CO$_2$H | A3 (R$^5$ = CH$_3$, R$^8$ = Br) | | |
| 61.4 | CO$_2$H | A3 (R$^5$ = C$_2$H$_5$, R$^8$ = Br) | | |
| 61.5 | CO$_2$H | A3 (R$^5$ = F, R$^8$ = Br) | | |
| 61.6 | CO$_2$H | A3 (R$^5$ = Cl, R$^8$ = Br) | | |
| 61.7 | CO$_2$H | A3 (R$^5$ = Br, R$^8$ = Br) | | |
| 61.8 | CO$_2$H | A3 (R$^5$ = I, R$^8$ = Br) | | |
| 62.1 | CO$_2$H | A3 (R$^5$ = CF$_3$, R$^8$ = I) | | |
| 62.2 | CO$_2$H | A3 (R$^5$ = CHF$_2$, R$^8$ = I) | | |
| 62.3 | CO$_2$H | A3 (R$^5$ = CH$_3$, R$^8$ = I) | | |
| 62.4 | CO$_2$H | A3 (R$^5$ = C$_2$H$_5$, R$^8$ = I) | | |
| 62.5 | CO$_2$H | A3 (R$^5$ = F, R$^8$ = I) | | |
| 62.6 | CO$_2$H | A3 (R$^5$ = Cl, R$^8$ = I) | | |
| 62.7 | CO$_2$H | A3 (R$^5$ = Br, R$^8$ = I) | | |

TABLE 1-continued

| Compound No. | $R^9$ | Ar | m.p. (° C.) | $^1$H—NMR(270 MHz) (CDCl$_3$, δ value, J:Hz) |
|---|---|---|---|---|
| 62.8 | CO$_2$H | A3 (R$^5$ = I, R$^8$ = I) | | |
| 63.1 | H | A3 (R$^5$ = CF$_3$, R$^8$ = H) | | |
| 63.2 | H | A3 (R$^5$ = CHF$_2$, R$^8$ = H) | | |
| 63.3 | H | A3 (R$^5$ = CH$_3$, R$^8$ = H) | 118.4~ 120.4 | 2.64(3H, s), 6.53(1H, d, J=2.3), 7.07 (1H, 4d, J=5.3, 1.3), 7.25(1H, dd, J=5.3, 3.3), 7.29(1H, d, J=2.3)7.63(1H, dd, J=3.3, 1.3), 7.41 (1H, brs) |
| 63.4 | H | A3 (R$^5$ = C$_2$H$_5$, R$^8$ = H) | | |
| 63.5 | H | A3 (R$^5$ = F, R$^8$ = H) | | |
| 63.6 | H | A3 (R$^5$ = Cl, R$^8$ = H) | | |
| 63.7 | H | A3 (R$^5$ = Br, R$^8$ = H) | | |
| 63.8 | H | A3 (R$^5$ = I, R$^8$ = H) | | |
| 64.1 | H | A3 (R$^5$ = CF$_3$, R$^8$ = CH$_3$) | | |
| 64.2 | H | A3 (R$^5$ = CHF$_2$, R$^8$ = CH$_3$) | | |
| 64.3 | H | A3 (R$^5$ = CH$_3$, R$^8$ = CH$_3$) | | |
| 64.4 | H | A3 (R$^5$ = C$_2$H$_5$, R$^8$ = CH$_3$) | | |
| 64.5 | H | A3 (R$^5$ = F, R$^8$ = CH$_3$) | | |
| 64.6 | H | A3 (R$^5$ = Cl, R$^8$ = CH$_3$) | | |
| 64.7 | H | A3 (R$^5$ = Br, R$^8$ = CH$_3$) | | |
| 64.8 | H | A3 (R$^5$ = I, R$^8$ = CH$_3$) | | |
| 65.1 | H | A3 (R$^5$ = CF$_3$, R$^8$ = CH$_2$CH$_3$) | | |
| 65.2 | H | A3 (R$^5$ = CHF$_2$, R$^8$ = CH$_2$CH$_3$) | | |
| 65.3 | H | A3 (R$^5$ = CH$_3$, R$^8$ = CH$_2$CH$_3$) | | |
| 65.4 | H | A3 (R$^5$ = C$_2$H$_5$, R$^8$ = CH$_2$CH$_3$) | | |
| 65.5 | H | A3 (R$^5$ = F, R$^8$ = CH$_2$CH$_3$) | | |
| 65.6 | H | A3 (R$^5$ = Cl, R$^8$ = CH$_2$CH$_3$) | | |
| 65.7 | H | A3 (R$^5$ = Br, R$^8$ = CH$_2$CH$_3$) | | |
| 65.8 | H | A3 (R$^5$ = I, R$^8$ = CH$_2$CH$_3$) | | |
| 66.1 | H | A3 (R$^5$ = CF$_3$, R$^8$ = F) | | |
| 66.2 | H | A3 (R$^5$ = CHF$_2$, R$^8$ = F) | | |
| 66.3 | H | A3 (R$^5$ = CH$_3$, R$^8$ = F) | | |
| 66.4 | H | A3 (R$^5$ = C$_2$H$_5$, R$^8$ = F) | | |
| 66.5 | H | A3 (R$^5$ = F, R$^8$ = F) | | |
| 66.6 | H | A3 (R$^5$ = Cl, R$^8$ = F) | | |
| 66.7 | H | A3 (R$^5$ = Br, R$^8$ = F) | | |
| 66.8 | H | A3 (R$^5$ = I, R$^8$ = F) | | |
| 67.1 | CO$_2$H | A3 (R$^5$ = CF$_3$, R$^8$ = Cl) | | |
| 67.2 | CO$_2$H | A3 (R$^5$ = CHF$_2$, R$^8$ = Cl) | | |
| 67.3 | CO$_2$H | A3 (R$^5$ = CH$_3$, R$^8$ = Cl) | | |
| 67.4 | CO$_2$H | A3 (R$^5$ = C$_2$H$_5$, R$^8$ = Cl) | | |

TABLE 1-continued

| Compound No. | $R^9$ | Ar | m.p. (° C.) | $^1$H—NMR(270 MHz) (CDCl$_3$, δ value, J:Hz) |
|---|---|---|---|---|
| 67.5 | CO$_2$H | A3 ($R^5$ = F, $R^8$ = Cl) | | |
| 67.6 | CO$_2$H | A3 ($R^5$ = Cl, $R^8$ = Cl) | | |
| 67.7 | CO$_2$H | A3 ($R^5$ = Br, $R^8$ = Cl) | | |
| 67.8 | CO$_2$H | A3 ($R^5$ = I, $R^8$ = Cl) | | |
| 68.1 | H | A3 ($R^5$ = CF$_3$, $R^8$ = Br) | | |
| 68.2 | H | A3 ($R^5$ = CHF$_2$, $R^8$ = Br) | | |
| 68.3 | H | A3 ($R^5$ = CH$_3$, $R^8$ = Br) | | |
| 68.4 | H | A3 ($R^5$ = C$_2$H$_5$, $R^8$ = Br) | | |
| 68.5 | H | A3 ($R^5$ = F, $R^8$ = Br) | | |
| 68.6 | H | A3 ($R^5$ = Cl, $R^8$ = Br) | | |
| 68.7 | H | A3 ($R^5$ = Br, $R^8$ = Br) | | |
| 68.8 | H | A3 ($R^5$ = I, $R^8$ = Br) | | |
| 69.1 | H | A3 ($R^5$ = CF$_3$, $R^8$ = I) | | |
| 69.2 | H | A3 ($R^5$ = CHF$_2$, $R^8$ = I) | | |
| 69.3 | H | A3 ($R^5$ = CH$_3$, $R^8$ = I) | | |
| 69.4 | H | A3 ($R^5$ = C$_2$H$_5$, $R^8$ = I) | | |
| 69.5 | H | A3 ($R^5$ = F, $R^8$ = I) | | |
| 69.6 | H | A3 ($R^5$ = Cl, $R^8$ = I) | | |
| 69.7 | H | A3 ($R^5$ = Br, $R^8$ = I) | | |
| 69.8 | H | A3 ($R^5$ = I, $R^8$ = I) | | |
| 70.1 | CO$_2$CH$_3$ | A4 ($R^5$ = CF$_3$, $R^8$ = H) | | |
| 70.2 | CO$_2$CH$_3$ | A4 ($R^5$ = CHF$_2$, $R^8$ = H) | | |
| 70.3 | CO$_2$CH$_3$ | A4 ($R^5$ = CH$_3$, $R^8$ = H) | 157.8~ 158.7 | 2.66(3H, s), 3.92(3H, s), 6.95(1H, d, J=4.9), 7.38(1H, d, J=4.9), 7.50(1H, d, J=5.3), 8.23(1H, d, J=5.3), 10.8(1 H,brs) |
| 70.4 | CO$_2$CH$_3$ | A4 ($R^5$ = C$_2$H$_5$, $R^8$ = H) | | |
| 70.5 | CO$_2$CH$_3$ | A4 ($R^5$ = F, $R^8$ = H) | | |
| 70.6 | CO$_2$CH$_3$ | A4 ($R^5$ = Cl, $R^8$ = H) | | |
| 70.7 | CO$_2$CH$_3$ | A4 ($R^5$ = Br, $R^8$ = H) | | |
| 70.8 | CO$_2$CH$_3$ | A4 ($R^5$ = J, $R^8$ = H) | | |
| 71.1 | CO$_2$CH$_3$ | A4 ($R^5$ = CF$_3$, $R^8$ = CH$_3$) | | |
| 71.2 | CO$_2$CH$_3$ | A4 ($R^5$ = CHF$_2$, $R^8$ = CH$_3$) | | |
| 71.3 | CO$_2$CH$_3$ | A4 ($R^5$ = CH$_3$, $R^8$ = CH$_3$) | | |
| 71.4 | CO$_2$CH$_3$ | A4 ($R^5$ = C$_2$H$_5$, $R^8$ = CH$_3$) | | |
| 71.5 | CO$_2$CH$_3$ | A4 ($R^5$ = F, $R^8$ = CH$_3$) | | |
| 71.6 | CO$_2$CH$_3$ | A4 ($R^5$ = Cl, $R^8$ = CH$_3$) | | |
| 71.7 | CO$_2$CH$_3$ | A4 ($R^5$ = Br, $R^8$ = CH$_3$) | | |
| 71.8 | CO$_2$CH$_3$ | A4 ($R^5$ = I, $R^8$ = CH$_3$) | | |
| 72.1 | CO$_2$CH$_3$ | A4 ($R^5$ = CF$_3$, $R^8$ = CH$_2$CH$_3$) | | |

TABLE 1-continued

| Compound No. | $R^9$ | Ar | m.p. (° C.) | $^1$H—NMR(270 MHz) (CDCl$_3$, δ value, J:Hz) |
|---|---|---|---|---|
| 72.2 | CO$_2$CH$_3$ | A4 ($R^5$ = CHF$_2$, $R^8$ = CH$_2$CH$_3$) | | |
| 72.3 | CO$_2$CH$_3$ | A4 ($R^5$ = CH$_3$, $R^8$ = CH$_2$CH$_3$) | | |
| 72.4 | CO$_2$CH$_3$ | A4 ($R^5$ = C$_2$H$_5$, $R^8$ = CH$_2$CH$_3$) | | |
| 72.5 | CO$_2$CH$_3$ | A4 ($R^5$ = F, $R^8$ = CH$_2$CH$_3$) | | |
| 72.6 | CO$_2$CH$_3$ | A4 ($R^5$ = Cl, $R^8$ = CH$_2$CH$_3$) | | |
| 72.7 | CO$_2$CH$_3$ | A4 ($R^5$ = Br, $R^8$ = CH$_2$CH$_3$) | | |
| 72.8 | CO$_2$CH$_3$ | A4 ($R^5$ = I, $R^8$ = CH$_2$CH$_3$) | | |
| 73.1 | CO$_2$CH$_3$ | A4 ($R^5$ = CF$_3$, $R^8$ = F) | | |
| 73.2 | CO$_2$CH$_3$ | A4 ($R^5$ = CHF$_2$, $R^8$ = F) | | |
| 73.3 | CO$_2$CH$_3$ | A4 ($R^5$ = CH$_3$, $R^8$ = F) | | |
| 73.4 | CO$_2$CH$_3$ | A4 ($R^5$ = C$_2$H$_5$, $R^8$ = F) | | |
| 73.5 | CO$_2$CH$_3$ | A4 ($R^5$ = F, $R^8$ = F) | | |
| 73.6 | CO$_2$CH$_3$ | A4 ($R^5$ = Cl, $R^8$ = F) | | |
| 73.7 | CO$_2$CH$_3$ | A4 ($R^5$ = Br, $R^8$ = F) | | |
| 73.8 | CO$_2$CH$_3$ | A4 ($R^5$ = I, $R^8$ = F) | | |
| 74.1 | CO$_2$CH$_3$ | A4 ($R^5$ = CF$_3$, $R^8$ = Cl) | | |
| 74.2 | CO$_2$CH$_3$ | A4 ($R^5$ = CHF$_2$, $R^8$ = Cl) | | |
| 74.3 | CO$_2$CH$_3$ | A4 ($R^5$ = CH$_3$, $R^8$ = Cl) | | |
| 74.4 | CO$_2$CH$_3$ | A4 ($R^5$ = C$_2$H$_5$, $R^8$ = Cl) | | |
| 74.5 | CO$_2$CH$_3$ | A4 ($R^5$ = F, $R^8$ = Cl) | | |
| 74.6 | CO$_2$CH$_3$ | A4 ($R^5$ = Cl, $R^8$ = Cl) | | |
| 74.7 | CO$_2$CH$_3$ | A4 ($R^5$ = Br, $R^8$ = Cl) | | |
| 74.8 | CO$_2$CH$_3$ | A4 ($R^5$ = I, $R^8$ = Cl) | | |
| 75.1 | CO$_2$CH$_3$ | A4 ($R^5$ = CF$_3$, $R^8$ = Br) | | |
| 75.2 | CO$_2$CH$_3$ | A4 ($R^5$ = CHF$_2$, $R^8$ = Br) | | |
| 75.3 | CO$_2$CH$_3$ | A4 ($R^5$ = CH$_3$, $R^8$ = Br) | | |
| 75.4 | CO$_2$CH$_3$ | A4 ($R^5$ = C$_2$H$_5$, $R^8$ = Br) | | |
| 75.5 | CO$_2$CH$_3$ | A4 ($R^5$ = F, $R^8$ = Br) | | |
| 75.6 | CO$_2$CH$_3$ | A4 ($R^5$ = Cl, $R^8$ = Br) | | |
| 75.7 | CO$_2$CH$_3$ | A4 ($R^5$ = Br, $R^8$ = Br) | | |
| 75.8 | CO$_2$CH$_3$ | A4 ($R^5$ = I, $R^8$ = Br) | | |
| 76.1 | CO$_2$CH$_3$ | A4 ($R^5$ = CF$_3$, $R^8$ = I) | | |
| 76.2 | CO$_2$CH$_3$ | A4 ($R^5$ = CHF$_2$, $R^8$ = I) | | |
| 76.3 | CO$_2$CH$_3$ | A4 ($R^5$ = CH$_3$, $R^8$ = I) | | |
| 76.4 | CO$_2$CH$_3$ | A4 ($R^5$ = C$_2$H$_5$, $R^8$ = I) | | |
| 76.5 | CO$_2$CH$_3$ | A4 ($R^5$ = F, $R^8$ = I) | | |
| 76.6 | CO$_2$CH$_3$ | A4 ($R^5$ = Cl, $R^8$ = I) | | |
| 76.7 | CO$_2$CH$_3$ | A4 ($R^5$ = Br, $R^8$ = I) | | |

TABLE 1-continued

| Compound No. | $R^9$ | Ar | m.p. (° C.) | $^1$H—NMR(270 MHz) (CDCl$_3$, δ value, J:Hz) |
|---|---|---|---|---|
| 76.8 | CO$_2$CH$_3$ | A4 ($R^5$ = I, $R^8$ = I) | | |
| 77.1 | CO$_2$H | A4 ($R^5$ = CF$_3$, $R^8$ = H) | | |
| 77.2 | CO$_2$H | A4 ($R^5$ = CHF$_2$, $R^8$ = H) | | |
| 77.3 | CO$_2$H | A4 ($R^5$ = CH$_3$, $R^8$ = H) | | |
| 77.4 | CO$_2$H | A4 ($R^5$ = C$_2$H$_5$, $R^8$ = H) | | |
| 77.5 | CO$_2$H | A4 ($R^5$ = F, $R^8$ = H) | | |
| 77.6 | CO$_2$H | A4 ($R^5$ = Cl, $R^8$ = H) | | |
| 77.7 | CO$_2$H | A4 ($R^5$ = Br, $R^8$ = H) | | |
| 77.8 | CO$_2$H | A4 ($R^5$ = I, $R^8$ = H) | | |
| 78.1 | CO$_2$H | A4 ($R^5$ = CF$_3$, $R^8$ = CH$_3$) | | |
| 78.2 | CO$_2$H | A4 ($R^5$ = CHF$_2$, $R^8$ = CH$_3$) | | |
| 78.3 | CO$_2$H | A4 ($R^5$ = CH$_3$, $R^8$ = CH$_3$) | | |
| 78.4 | CO$_2$H | A4 ($R^5$ = C$_2$H$_5$, $R^8$ = CH$_3$) | | |
| 78.5 | CO$_2$H | A4 ($R^5$ = F, $R^8$ = CH$_3$) | | |
| 78.6 | CO$_2$H | A4 ($R^5$ = Cl, $R^8$ = CH$_3$) | | |
| 78.7 | CO$_2$H | A4 ($R^5$ = Br, $R^8$ = CH$_3$) | | |
| 78.8 | CO$_2$H | A4 ($R^5$ = I, $R^8$ = CH$_3$) | | |
| 79.1 | CO$_2$H | A4 ($R^5$ = CF$_3$, $R^8$ = CH$_2$CH$_3$) | | |
| 79.2 | CO$_2$H | A4 ($R^5$ = CHF$_2$, $R^8$ = CH$_2$CH$_3$) | | |
| 79.3 | CO$_2$H | A4 ($R^5$ = CH$_3$, $R^8$ = CH$_2$CH$_3$) | | |
| 79.4 | CO$_2$H | A4 ($R^5$ = C$_2$H$_5$, $R^8$ = CH$_2$CH$_3$) | | |
| 79.5 | CO$_2$H | A4 ($R^5$ = F, $R^8$ = CH$_2$CH$_3$) | | |
| 79.6 | CO$_2$H | A4 ($R^5$ = Cl, $R^8$ = CH$_2$CH$_3$) | | |
| 79.7 | CO$_2$H | A4 ($R^5$ = Br, $R^8$ = CH$_2$CH$_3$) | | |
| 79.8 | CO$_2$H | A4 ($R^5$ = I, $R^8$ = CH$_2$CH$_3$) | | |
| 80.1 | CO$_2$H | A4 ($R^5$ = CF$_3$, $R^8$ = F) | | |
| 80.2 | CO$_2$H | A4 ($R^5$ = CHF$_2$, $R^8$ = F) | | |
| 80.3 | CO$_2$H | A4 ($R^5$ = CH$_3$, $R^8$ = F) | | |
| 80.4 | CO$_2$H | A4 ($R^5$ = C$_2$H$_5$, $R^8$ = F) | | |
| 80.5 | CO$_2$H | A4 ($R^5$ = F, $R^8$ = F) | | |
| 80.6 | CO$_2$H | A4 ($R^5$ = Cl, $R^8$ = F) | | |
| 80.7 | CO$_2$H | A4 ($R^5$ = Br, $R^8$ = F) | | |
| 80.8 | CO$_2$H | A4 ($R^5$ = I, $R^8$ = F) | | |
| 81.1 | CO$_2$H | A4 ($R^5$ = CF$_3$, $R^8$ = Cl) | | |
| 81.2 | CO$_2$H | A4 ($R^5$ = CHF$_2$, $R^8$ = Cl) | | |
| 81.3 | CO$_2$H | A4 ($R^5$ = CH$_3$, $R^8$ = Cl) | | |
| 81.4 | CO$_2$H | A4 ($R^5$ = C$_2$H$_5$, $R^8$ = Cl) | | |
| 81.5 | CO$_2$H | A4 ($R^5$ = F, $R^8$ = Cl) | | |

TABLE 1-continued

| Compound No. | $R^9$ | Ar | m.p. (° C.) | $^1$H—NMR(270 MHz) (CDCl$_3$, δ value, J:Hz) |
|---|---|---|---|---|
| 81.6 | CO$_2$H | A4 ($R^5$ = Cl, $R^8$ = Cl) | | |
| 81.7 | CO$_2$H | A4 ($R^5$ = Br, $R^8$ = Cl) | | |
| 81.8 | CO$_2$H | A4 ($R^5$ = I, $R^8$ = Cl) | | |
| 82.1 | CO$_2$H | A4 ($R^5$ = CF$_3$, $R^8$ = Br) | | |
| 82.2 | CO$_2$H | A4 ($R^5$ = CHF$_2$, $R^8$ = Br) | | |
| 82.3 | CO$_2$H | A4 ($R^5$ = CH$_3$, $R^8$ = Br) | | |
| 82.4 | CO$_2$H | A4 ($R^5$ = C$_2$H$_5$, $R^8$ = Br) | | |
| 82.5 | CO$_2$H | A4 ($R^5$ = F, $R^8$ = Br) | | |
| 82.6 | CO$_2$H | A4 ($R^5$ = Cl, $R^8$ = Br) | | |
| 82.7 | CO$_2$H | A4 ($R^5$ = Br, $R^8$ = Br) | | |
| 82.8 | CO$_2$H | A4 ($R^5$ = J, $R^8$ = Br) | | |
| 83.1 | CO$_2$H | A4 ($R^5$ = CF$_3$, $R^8$ = I) | | |
| 83.2 | CO$_2$H | A4 ($R^5$ = CHF$_2$, $R^8$ = I) | | |
| 83.3 | CO$_2$H | A4 ($R^5$ = CH$_3$, $R^8$ = I) | | |
| 83.4 | CO$_2$H | A4 ($R^5$ = C$_2$H$_5$, $R^8$ = I) | | |
| 83.5 | CO$_2$H | A4 ($R^5$ = F, $R^8$ = I) | | |
| 83.6 | CO$_2$H | A4 ($R^5$ = Cl, $R^8$ = I) | | |
| 83.7 | CO$_2$H | A4 ($R^5$ = Br, $R^8$ = I) | | |
| 83.8 | CO$_2$H | A4 ($R^5$ = I, $R^8$ = I) | | |
| 84.1 | H | A4 ($R^5$ = CF$_3$, $R^8$ = H) | | |
| 84.2 | H | A4 ($R^5$ = CHF$_2$, $R^8$ = H) | | |
| 84.3 | H | A4 ($R^5$ = CH$_3$, $R^8$ = H) | 100~ 100.8 | 2.58(3H, s), 6.93(1H, d, J=4.8), 7.07 (1H, dd, J=5.1, 1.3), 7.26(1H, dd, J=5.1, 3.1), 7.31(1H, d, J=4.8), 7.64(1H, dd, J=3.1, 1.3), 7.82 (1H, brs) |
| 84.4 | H | A4 ($R^5$ = C$_2$H$_5$, $R^8$ = H) | | |
| 84.5 | H | A4 ($R^5$ = F, $R^8$ = H) | | |
| 84.6 | H | A4 ($R^5$ = Cl, $R^8$ = H) | | |
| 84.7 | H | A4 ($R^5$ = Br, $R^8$ = H) | | |
| 84.8 | H | A4 ($R^5$ = I, $R^8$ = H) | | |
| 85.1 | H | A4 ($R^5$ = CF$_3$, $R^8$ = CH$_3$) | | |
| 85.2 | H | A4 ($R^5$ = CHF$_2$, $R^8$ = CH$_3$) | | |
| 85.3 | H | A4 ($R^5$ = CH$_3$, $R^8$ = CH$_3$) | | |
| 85.4 | H | A4 ($R^5$ = C$_2$H$_5$, $R^8$ = CH$_3$) | | |
| 85.5 | H | A4 ($R^5$ = F, $R^8$ = CH$_3$) | | |
| 85.6 | H | A4 ($R^5$ = Cl, $R^8$ = CH$_3$) | | |
| 85.7 | H | A4 ($R^5$ = Br, $R^8$ = CH$_3$) | | |
| 85.8 | H | A4 ($R^5$ = I, $R^8$ = CH$_3$) | | |
| 86.1 | H | A4 ($R^5$ = CF$_3$, $R^8$ = CH$_2$CH$_3$) | | |
| 86.2 | H | A4 ($R^5$ = CHF$_2$, $R^8$ = CH$_2$CH$_3$) | | |

TABLE 1-continued

| Compound No. | $R^9$ | Ar | m.p. (° C.) | $^1$H—NMR(270 MHz) (CDCl$_3$, δ value, J:Hz) |
|---|---|---|---|---|
| 86.3 | H | A4 ($R^5$ = CH$_3$, $R^8$ = CH$_2$CH$_3$) | | |
| 86.4 | H | A4 ($R^5$ = C$_2$H$_5$, $R^8$ = CH$_2$CH$_3$) | | |
| 86.5 | H | A4 ($R^5$ = F, $R^8$ = CH$_2$CH$_3$) | | |
| 86.6 | H | A4 ($R^5$ = Cl, $R^8$ = CH$_2$CH$_3$) | | |
| 86.7 | H | A4 ($R^5$ = Br, $R^8$ = CH$_2$CH$_3$) | | |
| 86.8 | H | A4 ($R^5$ = I, $R^8$ = CH$_2$CH$_3$) | | |
| 87.1 | H | A4 ($R^5$ = CF$_3$, $R^8$ = F) | | |
| 87.2 | H | A4 ($R^5$ = CHF$_2$, $R^8$ = F) | | |
| 87.3 | H | A4 ($R^5$ = CH$_3$, $R^8$ = F) | | |
| 87.4 | H | A4 ($R^5$ = C$_2$H$_5$, $R^8$ = F) | | |
| 87.5 | H | A4 ($R^5$ = F, $R^8$ = F) | | |
| 87.6 | H | A4 ($R^5$ = Cl, $R^8$ = F) | | |
| 87.7 | H | A4 ($R^5$ = Br, $R^8$ = F) | | |
| 87.8 | H | A4 ($R^5$ = I, $R^8$ = F) | | |
| 88.1 | CO$_2$H | A4 ($R^5$ = CF$_3$, $R^8$ = Cl) | | |
| 88.2 | CO$_2$H | A4 ($R^5$ = CHF$_2$, $R^8$ = Cl) | | |
| 88.3 | CO$_2$H | A4 ($R^5$ = CH$_3$, $R^8$ = Cl) | | |
| 88.4 | CO$_2$H | A4 ($R^5$ = C$_2$H$_5$, $R^8$ = Cl) | | |
| 88.5 | CO$_2$H | A4 ($R^5$ = F, $R^8$ = Cl) | | |
| 88.6 | CO$_2$H | A4 ($R^5$ = Cl, $R^8$ = Cl) | | |
| 88.7 | CO$_2$H | A4 ($R^5$ = Br, $R^8$ = Cl) | | |
| 88.8 | CO$_2$H | A4 ($R^5$ = I, $R^8$ = Cl) | | |
| 89.1 | H | A4 ($R^5$ = CF$_3$, $R^8$ = Br) | | |
| 89.2 | H | A4 ($R^5$ = CHF$_2$, $R^8$ = Br) | | |
| 89.3 | H | A4 ($R^5$ = CH$_3$, $R^8$ = Br) | | |
| 89.4 | H | A4 ($R^5$ = C$_2$H$_5$, $R^8$ = Br) | | |
| 89.5 | H | A4 ($R^5$ = F, $R^8$ = Br) | | |
| 89.6 | H | A4 ($R^5$ = Cl, $R^8$ = Br) | | |
| 89.7 | H | A4 ($R^5$ = Br, $R^8$ = Br) | | |
| 89.8 | H | A4 ($R^5$ = I, $R^8$ = Br) | | |
| 90.1 | H | A4 ($R^5$ = CF$_3$, $R^8$ = I) | | |
| 90.2 | H | A4 ($R^5$ = CHF$_2$, $R^8$ = I) | | |
| 90.3 | H | A4 ($R^5$ = CH$_3$, $R^8$ = I) | | |
| 90.4 | H | A4 ($R^5$ = C$_2$H$_5$, $R^8$ = I) | | |
| 90.5 | H | A4 ($R^5$ = F, $R^8$ = I) | | |
| 90.6 | H | A4 ($R^5$ = Cl, $R^8$ = I) | | |
| 90.7 | H | A4 ($R^5$ = Br, $R^8$ = I) | | |
| 90.8 | H | A4 ($R^5$ = I, $R^8$ = I) | | |

TABLE 1-continued

| Compound No. | $R^9$ | Ar | m.p. (° C.) | $^1$H—NMR(270 MHz) (CDCl$_3$, δ value, J:Hz) |
|---|---|---|---|---|
| 91.1 | CO$_2$CH$_3$ | A5 (R$^5$ = CF$_3$) | | |
| 91.2 | CO$_2$CH$_3$ | A5 (R$^5$ = CHF$_2$) | | |
| 91.3 | CO$_2$CH$_3$ | A5 (R$^5$ = CH$_3$) | 122.4~ 123.1 | 2.57(3H, s), 3.88(3H, s), 7.29~7.42 (3H, m), 7.53~7.55(1H, m), 7.60~ 7.63(1H, m), 8.30(1H, d, J= 5.3) 10.60(1H, brs) |
| 91.4 | CO$_2$CH$_3$ | A5 (R$^5$ = C$_2$H$_5$) | | |
| 91.5 | CO$_2$CH$_3$ | A5 (R$^5$ = F) | | |
| 91.6 | CO$_2$CH$_3$ | A5 (R$^5$ = Cl) | | |
| 91.7 | CO$_2$CH$_3$ | A5 (R$^5$ = Br) | | |
| 91.8 | CO$_2$CH$_3$ | A5 (R$^5$ = I) | | |
| 92.1 | CO$_2$H | A5 (R$^5$ = CF$_3$) | | |
| 92.2 | CO$_2$H | A5 (R$^5$ = CHF$_2$) | | |
| 92.3 | CO$_2$H | A5 (R$^5$ = CH$_3$) | 200.9~ 201.4 | 2.46(3H, s), 7.33–7.38(2H, m), 7.44– 7.50(1H, m), 7.60–7.64(1H, m), 7.93 (1H, d, J= 5.6), 8.11(1H, d, J=5.6), 10 .7(1H,s) |
| 92.4 | CO$_2$H | A5 (R$^5$ = C$_2$H$_5$) | | |
| 92.5 | CO$_2$H | A5 (R$^5$ = F) | | |
| 92.6 | CO$_2$H | A5 (R$^5$ = Cl) | | |
| 92.7 | CO$_2$H | A5 (R$^5$ = Br) | | |
| 92.8 | CO$_2$H | A5 (R$^5$ = I) | | |
| 93.1 | H | A5 (R$^5$ = CF$_3$) | | |
| 93.2 | H | A5 (R$^5$ = CHF$_2$) | | |
| 93.3 | H | A5 (R$^5$ = CH$_3$) | 162.2~ 163.8 | 2.49(3H, s), 7.05(1H, dd, J=5.3, 1.3) , 7.24–7.36(5H,m), 7.70(1H, dd, J= 2.9, 1.3), 7.84(1H, brs) |
| 93.4 | H | A5 (R$^5$ = C$_2$H$_5$) | | |
| 93.5 | H | A5 (R$^5$ = F) | | |
| 93.6 | H | A5 (R$^5$ = Cl) | | |
| 93.7 | H | A5 (R$^5$ = Br) | | |
| 93.8 | H | A5 (R$^5$ = I) | | |
| 94.1 | CO$_2$CH$_3$ | A6 (R$^5$ = CF$_3$) | | |
| 94.2 | CO$_2$CH$_3$ | A6 (R$^5$ = CHF$_2$) | | |
| 93.3 | CO$_2$CH$_3$ | A6 (R$^5$ = CH$_3$) | | |
| 93.4 | CO$_2$CH$_3$ | A6 (R$^5$ = C$_2$H$_5$) | | |
| 94.5 | CO$_2$CH$_3$ | A6 (R$^5$ = F) | | |
| 94.6 | CO$_2$CH$_3$ | A6 (R$^5$ = Cl) | 152.5~ 153.4 | 3.90(3H, s), 7.40(1H, dd, J=7.6, 4.9) , 7.56 (1H, d, J=5.3), 8.09 (1H, dd, J=7 .6, 2.0), 8.27(1H, d, J=5.3), 8.54(1H , dd, J=4.9, 2.0), 10.92(1H, brs) |
| 93.7 | CO$_2$CH$_3$ | A6 (R$^5$ = Br) | | |
| 94.8 | CO$_2$CH$_3$ | A6 (R$^5$ = I) | | |
| 95.1 | CO$_2$H | A6 (R$^5$ = CF$_3$) | | |
| 95.2 | CO$_2$H | A6 (R$^5$ = CHF$_2$) | | |
| 95.3 | CO$_2$H | A6 (R$^5$ = CH$_3$) | | |
| 95.4 | CO$_2$H | A6 (R$^5$ = C$_2$H$_5$) | | |
| 95.5 | CO$_2$H | A6 (R$^5$ = F) | | |
| 95.6 | CO$_2$H | A6 (R$^5$ = Cl) | more than 200° C. | 7.61(1H, dd, J=7.6, 4.9), 7.92(1H, d, J=5.3), 8.06(1H, d, J=5.3), 8.21(1H, dd, J=7.6, 2.0), 8.59 (1H, dd, J=4.9, 2 .0), 10.84(1H, s) |
| 95.7 | CO$_2$H | A6 (R$^5$ = Br) | | |
| 95.8 | CO$_2$H | A6 (R$^5$ = I) | | |
| 96.1 | H | A6 (R$^5$ = CF$_3$) | | |
| 96.2 | H | A6 (R$^5$ = CHF$_2$) | | |
| 96.3 | H | A6 (R$^6$ = CH$_3$) | | |
| 96.4 | H | A6 (R$^5$ = C$_2$H$_5$) | | |
| 96.5 | H | A6 (R$^5$ = F) | | |
| 96.6 | H | A6 (R$^5$ = Cl) | semi- solid | 7.11(1H, dd, J=5.3, 1.3), 7.30(1H, dd , J=5.3, 3.3), 7.41(1H, dd, J=7.9, 4.7 ), 7.76 (1H, dd, J=3.3, 1.3), 8.20– 8.23(1H, m), 8.50(1H, dd, J= 4.7, 2.0), 8.58(1H, brs) |
| 96.7 | H | A6 (R$^5$ = Br) | | |
| 96.8 | H | A6 (R$^5$ = I) | | |
| 97.1 | CO$_2$CH$_3$ | A7 | | |
| 97.2 | CO$_2$H | A7 | | |
| 97.3 | H | A7 | | |
| 98.1 | CO$_2$CH$_3$ | A8 (R$^5$ = CF$_3$) | | |
| 98.2 | CO$_2$CH$_3$ | A8 (R$^5$ = CHF$_2$) | | |
| 98.3 | CO$_2$CH$_3$ | A8 (R$^5$ = CH$_3$) | | |
| 98.4 | CO$_2$CH$_3$ | A8 (R$^5$ = C$_2$H$_5$) | | |
| 98.5 | CO$_2$CH$_3$ | A8 (R$^5$ = F) | | |
| 98.6 | CO$_2$CH$_3$ | A8 (R$^5$ = Cl) | | |
| 98.7 | CO$_2$CH$_3$ | A8 (R$^5$ = Br) | | |

TABLE 1-continued

| Compound No. | $R^9$ | Ar | m.p. (° C.) | $^1$H—NMR(270 MHz) (CDCl$_3$, δ value, J:Hz) |
|---|---|---|---|---|
| 98.8 | CO$_2$CH$_3$ | A8 (R$^5$ = I) | | |
| 99.1 | CO$_2$H | A8 (R$^5$ = CF$_3$) | | |
| 99.2 | CO$_2$H | A8 (R$^5$ = CHF$_2$) | | |
| 99.3 | CO$_2$H | A8 (R$^5$ = CH$_3$) | | |
| 99.4 | CO$_2$H | A8 (R$^5$ = C$_2$H$_5$) | | |
| 99.5 | CO$_2$H | A8 (R$^5$ = F) | | |
| 99.6 | CO$_2$H | A8 (R$^5$ = Cl) | | |
| 99.7 | CO$_2$H | A8 (R$^5$ = Br) | | |
| 99.8 | CO$_2$H | A8 (R$^5$ = I) | | |
| 100.1 | H | A8 (R$^5$ = CF$_3$) | | |
| 100.2 | H | A8 (R$^5$ = CHF$_2$) | | |
| 100.3 | H | A8 (R$^5$ = CH$_3$) | | |
| 100.4 | H | A8 (R$^5$ = C$_2$H$_5$) | | |
| 100.5 | H | A8 (R$^5$ = F) | | |
| 100.6 | H | A8 (R$^5$ = Cl) | | |
| 100.7 | H | A8 (R$^5$ = Br) | | |
| 100.8 | H | A8 (R$^5$ = I) | | |
| 101.1 | CO$_2$CH$_3$ | A9 (R$^5$ = CF$_3$) | | |
| 101.2 | CO$_2$CH$_3$ | A9 (R$^5$ = CHF$_2$) | | |
| 101.3 | CO$_2$CH$_3$ | A9 (R$^5$ = CH$_3$) | | |
| 101.4 | CO$_2$CH$_3$ | A9 (R$^5$ = C$_2$H$_5$) | | |
| 102.1 | CO$_2$H | A9 (R$^5$ = CF$_3$) | | |
| 102.2 | CO$_2$H | A9 (R$^5$ = CHF$_2$) | | |
| 102.3 | CO$_2$H | A9 (R$^5$ = CH$_3$) | | |
| 102.4 | CO$_2$H | A9 (R$^5$ = C$_2$H$_5$) | | |
| 103.1 | H | A9 (R$^5$ = CF$_3$) | | |
| 103.2 | H | A9 (R$^5$ = CHF$_2$) | | |
| 103.3 | H | A9 (R$^5$ = CH$_3$) | 151.1~152.6 | 1.89~1.97(2H, m), 2.19(3H, s), 2.32~2.37(2H, m), 4.02~4.05 (2H, m), 6.99(1H, dd, J=5.3, 1.3), 7.23(1H, dd, J=5.3, 3.3), 7.40(1H, brs), 7.58(1H, dd J= 3.3, 1.3) |
| 103.4 | H | A9 (R$^5$ = C$_2$H$_5$) | | |
| 104.1 | CO$_2$CH$_3$ | A10 (R$^5$ = CF$_3$) | | |
| 104.2 | CO$_2$CH$_3$ | A10 (R$^5$ = CHF$_2$) | | |
| 104.3 | CO$_2$CH$_3$ | A10 (R$^5$ = CH$_3$) | | |
| 104.4 | CO$_2$CH$_3$ | A10 (R$^5$ = C$_2$H$_5$) | | |
| 105.1 | CO$_2$H | A10 (R$^5$ = CF$_3$) | | |
| 105.2 | CO$_2$H | A10 (R$^5$ = CHF$_2$) | | |
| 105.3 | CO$_2$H | A10 (R$^5$ = CH$_3$) | | |
| 105.4 | CO$_2$H | A10 (R$^5$ = C$_2$H$_5$) | | |
| 106.1 | H | A10 (R$^5$ = CF$_3$) | | |
| 106.2 | H | A10 (R$^5$ = CHF$_2$) | | |
| 106.3 | H | A10 (R$^5$ = CH$_3$) | | |
| 106.4 | H | A10 (R$^5$ = C$_2$H$_5$) | | |
| 107.1 | CO$_2$CH$_3$ | A11 (R$^5$ = CF$_3$) | | |
| 107.2 | CO$_2$CH$_3$ | A11 (R$^5$ = CHF$_2$) | | |
| 107.3 | CO$_2$CH$_3$ | A11 (R$^5$ = CH$_3$) | | |
| 107.4 | CO$_2$CH$_3$ | A11 (R$^5$ = C$_2$H$_5$) | | |
| 108.1 | CO$_2$H | A11 (R$^5$ = CF$_3$) | | |
| 108.2 | CO$_2$H | A11 (R$^5$ = CHF$_2$) | | |
| 108.3 | CO$_2$H | A11 (R$^5$ = CH$_3$) | | |
| 108.4 | CO$_2$H | A11 (R$^5$ = C$_2$H$_5$) | | |
| 109.1 | H | A11 (R$^5$ = CF$_3$) | | |
| 109.2 | H | A11 (R$^5$ = CHF$_2$) | | |
| 109.3 | H | A11 (R$^5$ = CH$_3$) | | |
| 109.4 | H | A11 (R$^5$ = C$_2$H$_5$) | | |
| 110.1 | CO$_2$CH$_3$ | A12 (R$^5$ = CF$_3$) | | |
| 110.2 | CO$_2$CH$_3$ | A12 (R$^5$ = CHF$_2$) | | |
| 110.3 | CO$_2$CH$_3$ | A12 (R$^5$ = CH$_3$) | | |
| 110.4 | CO$_2$CH$_3$ | A12 (R$^5$ = C$_2$H$_5$) | | |
| 110.5 | CO$_2$CH$_3$ | A12 (R$^5$ = F) | | |

TABLE 1-continued

| Compound No. | $R^9$ | Ar | m.p. (° C.) | $^1$H—NMR(270 MHz) (CDCl$_3$, δ value, J:Hz) |
|---|---|---|---|---|
| 110.6 | $CO_2CH_3$ | A12 ($R^5$ = Cl) | | |
| 110.7 | $CO_2CH_3$ | A12 ($R^5$ = Br) | | |
| 110.8 | $CO_2CH_3$ | A12 ($R^5$ = I) | | |
| 111.1 | $CO_2H$ | A12 ($R^5$ = $CF_3$) | | |
| 111.2 | $CO_2H$ | A12 ($R^5$ = $CHF_2$) | | |
| 111.3 | $CO_2H$ | A12 ($R^5$ = $CH_3$) | | |
| 111.4 | $CO_2H$ | A12 ($R^5$ = $C_2H_5$) | | |
| 111.5 | $CO_2H$ | A12 ($R^5$ = F) | | |
| 111.6 | $CO_2H$ | A12 ($R^5$ = Cl) | | |
| 111.7 | $CO_2H$ | A12 ($R^5$ = Br) | | |
| 111.8 | $CO_2H$ | A12 ($R^5$ = I) | | |
| 112.1 | H | A12 ($R^5$ = $CF_3$) | | |
| 112.2 | H | A12 ($R^5$ = $CHF_2$) | | |
| 112.3 | H | A12 ($R^5$ = $CH_3$) | | |
| 112.4 | H | A12 ($R^5$ = $C_2H_5$) | | |
| 112.5 | H | A12 ($R^5$ = F) | | |
| 112.6 | H | A12 ($R^5$ = Cl) | | |
| 112.7 | H | A12 ($R^5$ = Br) | | |
| 112.8 | H | A12 ($R^5$ = I) | | |
| 113.1 | $CO_2C_2H_5$ | A1 ($R^5$ = $CF_3$, $R^7$ = H) | 144.8 ~ 146.2 | 1.40(3H, t, J=7.3), 4.02(3H, s), 4.36 (2H, q, J=7.3), 7.50(1H, d, J=5.6), 7.95(1H, s), 8.18(1H, d, J=5.6), 10.7(1H, brs) |
| 113.2 | $CO_2{}^iPr$ | A1 ($R^5$ = $CF_3$, $R^7$ = H) | 159.6 ~ 161.5 | 1.37(6H, d, J=6.2), 4.03(3H, s), 5.22 (1H, sept, J=6.2), 7.49(1H, d, J=5.0), 7.96(1H, s), 8.18(1H, d, J= 5.0), 10.8(1H, brs) |
| 113.3 | $CO_2C_2H_5$ | A2 ($R^5$ = $CH_3$, $R^6$ = $CH_3$) | | |
| 113.4 | $CO_2{}^nPr$ | A3 ($R^5$ = $CH_3$, $R^8$ = H) | | |
| 113.5 | $CO_2{}^nBu$ | A4 ($R^5$ = $CH_3$, $R^8$ = H) | | |
| 113.6 | $CO_2{}^sBu$ | A5 ($R^5$ = $CF^3$) | | |
| 113.7 | $CO_2{}^tBu$ | A6 ($R^5$ = Cl) | | |
| 113.8 | $CO_2{}^nPen$ | A7 | | |
| 113.9 | $CO_2{}^nHex$ | A8 ($R^5$ = $CH_3$) | | |
| 113.1 | $CO_2{}^cHex$ | A9 ($R^5$ = $CH_3$) | | |
| 113.11 | $CO_2{}^nPr$ | A10 ($R^5$ = $CH_3$) | | |
| 113.12 | $CO_2{}^cPr$ | A11 ($R^5$ = $CH_3$) | | |
| 113.13 | $CO_2C_2H_5$ | A12 ($R^5$ = Cl) | | |

Pr: propyl, Bu: butyl, Pent: pentyl, Hex: hexyl, i: iso, n: normal, s: secondary, t: tertially, c: cyclo Examples of a compound of the general formula (1b) which is an intermediate of the present invention are summarized in the following Table 2.

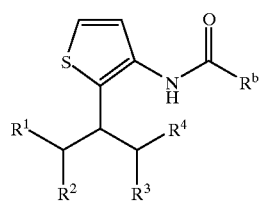

(1b)

TABLE 2

| Compound No. | R | $R^1$~$R^4$ | Physical property | $^1$H-NMR (270 MHz) (CDCl$_3$, δ value, J:Hz) |
|---|---|---|---|---|
| 114.1 | H | $R^1$ = $R^2$ = | | |
| 114.2 | $CH_3$ | $R^3$ = H, $R^4$ = i-$C_3H_7$ $R^1$ = $R^2$ = $R^3$ = H, $R^4$ = i-$C_3H_7$ | colorless crystal | 0.88(6H, d, J=6.9), 1.26(3H, d, J=6.9), 1.39–1.59(3H, m), 2.16(3H, s), 3.00–3.08(1H, m), 7.07(1H, d, J=5.3), 7.23(1H, d, J=5.3) |
| 114.3 | Ph | $R^1$ = $R^2$ = $R^3$ = H, $R^4$ = i-$C_3H_7$ | m.p. 105.2~ 105.8° C. | 0.88 (3H, d, J=6.3), 0.89(3H, d, J=6.3) 1.30(3H, d, J=6.3), 1.39–1.63(3H, m), 3.11(1H, sext, J=6.3), 7.14(1H, d, J=5.3), 7.42–7.59(5H, m), 7.86(2H, d, J=6.9) |
| 114.4 | $OC_2H_5$ | $R^1$ = $R^2$ = | | |

TABLE 2-continued

| Compound No. | R | $R^1 \sim R^4$ | Physical property | $^1$H-NMR (270 MHz) (CDCl$_3$, δ value, J:Hz) |
|---|---|---|---|---|
| 114.5 | i-OC$_3$H$_7$ | $R^1 = R^2 =$ $R^3 = H$, $R^4 = $ i-C$_3$H$_7$ | m.p. 57.8~ 59.9° C. | 0.87(3H, d, J=6.3), 0.88(3H, d, J=6.3), 1.23–1.30(9H, m), 1.38–1.58(3H, m), 3.04(1H, sext, J=6.3), 4.99(1H, sept, J=6.3), 6.13(1H, brs), 7.05 (1H, d, J=5.3) |
| 114.6 | OBz | $R^1 = R^2 =$ $R^3 = H$, $R^4 = $ i-C$_3$H$_7$ | colorless crystal | 0.85(6H, d, J=6.9), 1.22(3H, d, J=6.9), 1.38–1.55(3H, m), 3.02(1H, sext, J=6.9), 5.19(2H, s), 6.25(1H, brs), 7.07(1H, d, J= 5.3), 7.24–7.38 (6H, m) |

Examples of compounds of the general formulae (4a)' to (4d)' which are intermediates of the present invention are summarized in the following Table 3.

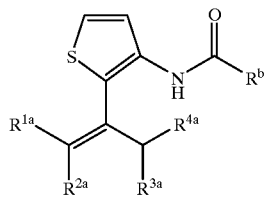
(4a)'

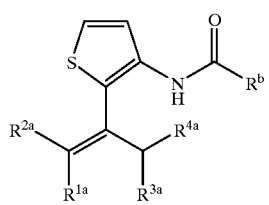
(4b)'

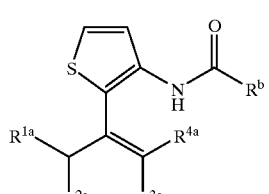
(4c)'

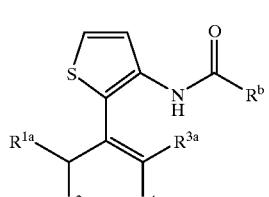
(4d)'

TABLE 3

| Compound No. | R | $R^1 \sim R^4$ | Physical property | $^1$H-NMR (270 MHz) (CDCl$_3$, δ value, J:Hz) |
|---|---|---|---|---|
| 115.1 | H | $R^{1a} = R^{2a} =$ $R^{3a} = H$, $R^{4a} = $ i-C$_3$H$_7$ | b.p. 123~ 130° C. /4 mm Hg | 0.89(6H, m), 1.94–2.01 (3H, m), 2.35(1H, m), 5.52(1H, m), 7.32(1H, m), 7.60(1H, m), 8.30 (1H, m), 5.26–5.43 (1/20×2H, exo-methylene protons) |
| 115.2 | CH$_3$ | $R^{1a} = R^{2a} =$ $R^{3a} = H$, $R^{4a} = $ i-C$_3$H$_7$ | b.p. 123~ 137° C. /2 mm Hg | 0.93–1.06(6H, m), 1.96–1.99(3H, m), 2.12(3H, s), 2.25–2.70 (1H, m), 5.47–5.55 (1H, m), 7.11–7.19(1H, d, J=5.3), 7.33(1H, brs), 7.65–7.74(1H, m), 5.19–5.28(1/10×2H, exo-methylene protons) |
| 115.3 | Ph | $R^{1a} = R^{2a} =$ $R^{3a} = H$, $R^{4a} = $ i-C$_3$H$_7$ | colorless crystal | 0.86–1.07(6H, m), 2.00–2.05(3H, m), 2.24–2.82(1H, m), 5.55–5.63(1H, m), 7.18–7.27(1H, m), 7.45–7.54(3H, m), 7.80–7.95(3H, m), 8.27(1H, brs), 5.27–5.36 (1/5×2H, exo-methylene protons) |
| 115.4 | OC$_2$C$_5$ | $R^{1a} = R^{2a} =$ $R^{3a} = H$, $R^{4a} = $ i-C$_3$H$_7$ | oil | 0.92–1.05(6H, m), 1.27(3H, m), 1.93–1.99(3H, m), 2.24–2.67 (1H, m), 4.21(2H, q, J=7.2), 5.47–5.50(1H, m), 7.09(1H, d, J=5.3), 7.18(1H, d, J=5.3), 5.19–5.27(1/10×2H, exo-methylene protons) |
| 115.5 | i-OC$_3$H$_7$ | $R^{1a} = R^{2a} =$ $R^{3a} = H$, $R^{4a} = $ i-C$_3$H$_7$ | colorless crystal | 0.91–1.05(6H, m), 1.23–1.30(6H, m), 1.94–1.98(3H, m), 2.12–2.74(1H, m), 4.94–5.04(1H, m), 5.44–5.53(1H, m), 6.38–6.57(1H, m), 7.08–7.17(1H, m), 7.49–7.57(1H, m), 5.18–5.26(1/6×2H, exo-methylene protons) |
| 115.6 | OBz | $R^{1a} = R^{2a} =$ $R^{3a} = H$, $R^{4a} = $ I-C$_3$H$_7$ | oil | 0.89–1.02(6H, m), 1.92–1.97(3H, m), 2.18–2.70(1H, m), 5.18–5.19(2H, m), 5.44–5.52(1H, m), 6.51–6.70(1H, m), 7.09–7.18(1H, m), 7.33–7.41(5H, m), 7.50–7.60(1H, m), 5.21–5.25(1/4×2H, exo-methylene protons) |

According to the present invention, a 2-alkyl-3-aminothiophene derivative having a secondary alkyl group represented by the formula (1) can be produced simply and at high yield by reacting a compound of the formula (2) with a compound of the formula (3) in the presence of an acid and reducing the resultant reaction mixture.

What is claimed is:
1. A 3-aminothiophene derivative represented by the formula (6a):

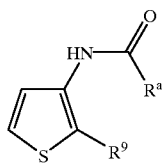

(6a)

wherein, $R^9$ represents a hydrogen atom, carboxyl group or alkoxycarbonyl group having 1 to 6 carbon atoms and $R^a$ represents a group represented by any of the following (A1) to (A12):

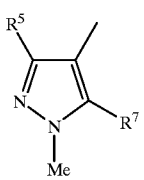

(A1)

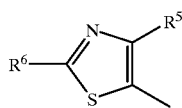

(A2)

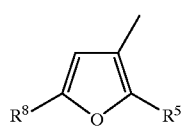

(A3)

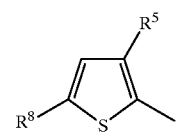

(A4)

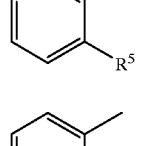

(A5)

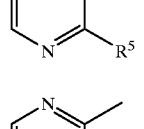

(A6)

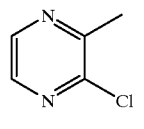

(A7)

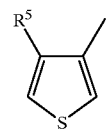

(A8)

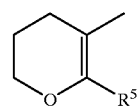

(A9)

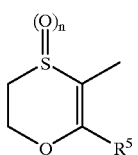

(A10)

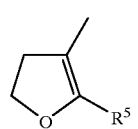

(A11)

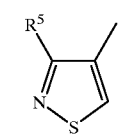

(A12)

wherein, $R^5$ represents a trifluoromethyl group, difluoromethyl group, methyl group, ethyl group or halogen atom, $R^6$ represents a hydrogen atom, methyl group, trifluoromethyl group, halogen atom, methoxy group or amino group, $R^7$ represents a hydrogen atom, halogen atom, methyl group or methoxy group, $R^8$ represents a hydrogen atom, methyl group, ethyl group or halogen atom, and n represents an integer from 0 to 2, and herein, in the case of (A9), (A10) or (A11), $R^5$ is not a halogen atom.

2. The 3-aminothiophene derivative according to claim 1 wherein $R^a$ represents (A1), (A2), (A3), (A4) or (A9).

3. The 3-aminothiophene derivative according to claim 2 wherein $R^a$ represents (A1), (A2), (A3) or (A4).

4. The 3-aminothiophene derivative according to claim 3 wherein $R^a$ represents (A1).

5. The 3-aminothiophene derivative according to claim 4 wherein $R^5$ represents a trifluoromethyl group and $R^7$ represents a hydrogen atom.

\* \* \* \* \*